US011464879B2

(12) United States Patent
Krol et al.

(10) Patent No.: US 11,464,879 B2
(45) Date of Patent: Oct. 11, 2022

(54) CELLULAR TARGETED ACTIVE INGREDIENT DELIVERY SYSTEM

(71) Applicant: CELLIS SP. Z O.O. [LTD.], Warsaw (PL)

(72) Inventors: Magdalena Krol, Warsaw (PL); Irene Benni, Rome (IT); Paola Baiocco, Rome (IT); Tomasz Rygiel, Warsaw (PL); Alberto Boffi, Rome (IT)

(73) Assignee: CELLIS AG

( * ) Notice: Subject to any disclaimer, the term of this patent is extended or adjusted under 35 U.S.C. 154(b) by 380 days.

(21) Appl. No.: 15/739,382

(22) PCT Filed: Jun. 22, 2016

(86) PCT No.: PCT/EP2016/064484
§ 371 (c)(1),
(2) Date: Dec. 22, 2017

(87) PCT Pub. No.: WO2016/207257
PCT Pub. Date: Dec. 29, 2016

(65) Prior Publication Data
US 2020/0030374 A1 Jan. 30, 2020

(30) Foreign Application Priority Data
Jun. 22, 2015 (PL) ......................................... 412787

(51) Int. Cl.
| | | |
|---|---|---|
| *A61K 35/15* | (2015.01) | |
| *A61K 51/12* | (2006.01) | |
| *A61K 47/68* | (2017.01) | |
| *A61K 47/64* | (2017.01) | |
| *A61K 47/69* | (2017.01) | |
| *A61K 35/17* | (2015.01) | |
| *A61K 45/06* | (2006.01) | |
| *A61K 49/00* | (2006.01) | |
| *A61K 49/18* | (2006.01) | |
| *A61K 51/04* | (2006.01) | |
| *C12N 5/0783* | (2010.01) | |
| *C12N 5/0787* | (2010.01) | |
| *C12N 5/0786* | (2010.01) | |

(52) U.S. Cl.
CPC .......... *A61K 51/1203* (2013.01); *A61K 35/15* (2013.01); *A61K 35/17* (2013.01); *A61K 45/06* (2013.01); *A61K 47/64* (2017.08); *A61K 47/644* (2017.08); *A61K 47/6445* (2017.08); *A61K 47/6811* (2017.08); *A61K 47/6901* (2017.08); *A61K 49/0056* (2013.01); *A61K 49/1896* (2013.01); *A61K 51/0497* (2013.01); *C12N 5/0636* (2013.01); *C12N 5/0642* (2013.01); *C12N 5/0645* (2013.01); *C12N 5/0646* (2013.01); *C12N 2501/15* (2013.01); *C12N 2501/21* (2013.01); *C12N 2501/231* (2013.01); *C12N 2501/2304* (2013.01); *C12N 2501/2313* (2013.01); *C12N 2501/24* (2013.01); *C12N 2501/25* (2013.01); *C12N 2501/90* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 7,608,268 B2 * | 10/2009 | Carter ..................... | A61K 39/12 424/134.1 |
| 8,951,561 B2 * | 2/2015 | Vo-Dinh ............ | A61K 41/0066 424/489 |
| 2015/0224211 A1 * | 8/2015 | Troyer ............... | A61K 49/0041 424/9.1 |

FOREIGN PATENT DOCUMENTS

| | | |
|---|---|---|
| RU | 2552609 | 5/2015 |
| WO | WO 2007/113572 | 10/2007 |
| WO | WO 2008/054509 | 5/2008 |
| WO | 2011/119881 | 9/2011 |
| WO | WO 2012/027376 | 3/2012 |
| WO | WO 2014/031727 | 2/2014 |
| WO | WO 2014/208100 | 12/2014 |
| WO | WO 2015/012315 | 1/2015 |
| WO | WO 2015135597 | * 9/2015 |
| WO | WO 2016/207257 | 12/2016 |

OTHER PUBLICATIONS

Gammella et al. "Macrophages: central regulators of iron balance." Metallomics 6.8 (2014): 1336-1345 (Year: 2014).*
Schonberg et al (J of Neuroscience (2012, 32, pp. 5374-5384).*
Mitchell et al ( Expert Opinion on Drug Delivery 2015, v.12.pp. 375-392.*
Pizzurro, et al., "dendritic cell-based vaccine efficacy: aiming for hot spots," Frontiers in Immunology, vol. 6 (91) Mar. 2015.
Han, Jae-A et al. "Fen-itin protein cage nanoparticles as versatile antigen delivery nanoplatforms for dendritic cell (DC)-based vaccine development" Nanomedicine: Nanothechnology, Biology, and Medicine (2014) vol. 10(3), pp. 561-569.
Xu, Feng et al. "Long-circulation of hemoglobin-loaded polymeric nanoparticles as oxygen carriers with modulated surface charges" International Journal of Pharmaceutical (2009) vol. 377(1-2), pp. 199-206.
Choi, Jinhyang et al., Use of macro phages to deliver therapeutic and imaging contrast agents to tumors' Biomaterials (2012) vol. 33(16), pp. 4195-4203.

(Continued)

*Primary Examiner* — Michail A Belyavskyi
(74) *Attorney, Agent, or Firm* — McDonnell Boehnen Hulbert & Berghoff LLP

(57) ABSTRACT

The present invention relates to an isolated cellular targeted delivery system comprising a CD45+ leukocyte cell comprising within said cell a complex of one or more iron binding proteins and an active ingredient as well as methods for producing such isolated cellular targeted delivery system and uses of such system for therapy, in particular for therapy of cancer.

9 Claims, 23 Drawing Sheets

Specification includes a Sequence Listing.

(56) References Cited

OTHER PUBLICATIONS

Daniels, Tracy R. et al., "The transferrin receptor and the targeted delivery of therapeutic agents against cancer" Biochimica et Biophysica Acta (2012) vol. 1820(3), pp. 219-317.
Yousefpour, Parisa et al. Co-opting biology to deliver drugs' Biotechnology and Bioengineering (2014) vol. 111 (9), pp. 1699-1716.
The International Search Report (ISR) for PCT/EP2016/064484 dated Sep. 22, 2016, pp. 1-4.
Written Opinion of the International Searching Authority for PCT/EP2016/064484 dated Sep. 22, 2016, pp. 1-7.
Liang et al., "H-ferritin-nanocaged doxorubicin nanoparticles specifically target and kill tumors with a single-dose injection." PNAS 111(41):14900-14905 (Sep. 2014).
Anselmo et al., "Cell-mediated delivery of nanoparticles: Taking advantage of circulatory cells to target nanoparticles" Journal of Controlled Release 190:531-41 (Sep. 2014).
Finke et al., "Coumarin 6 as a fluorescent model drug: How to identify properties of lipid colloidal drug delivery systems via fluorescence spectroscopy? Coumarin 6 in colloidal drug delivery systems" European Journal of Lipid Science and Technology, 116(9):1234-46 (Sep. 2014).
Li et al., "Peptide Vaccine: Progress and Challenges." Vaccines 2(3):515-36 (Jul. 2014).
Liu "It is possible that tumour-infiltrating granulocytes promote tumour progression." Oncology Reports 22 (1):29-33 (Jul. 2009). PMID: 19513501.
Ma et al., "Dendritic cells in the cancer microenvironment." Journal of Cancer 4(1):36-44 (2013).
Palmer et al., "Vaccine stimulated, Adoptively Transferred CD8+ T-Cells Traffic Indiscriminately and Ubiquitously while Mediating Specific Tumor Destruction," The Journal of Immunology, vol. 173, No. 12, pp. 7209-7216 (Dec. 2004).
Terashima et al., "Human ferritin cages for imaging vascular macrophages," Biomaterials vol. 32, No. 5, Feb. 2011, pp. 1430-1437.
DyLight Technology and Product Guide—accessed Dec. 17, 2020, 4 pages.
He et al., "Ferritin drug carrier (FDC) for tumor targeting therapy" Journal of Controlled Release 311-312:288-300 (Sep. 2019).
Nguyen et al., "Hepcidin expression an iron transport in alveolar macrophages" American Journal of Physiol. 293(3, Pt1):L417-L425 (2006).
Huang et all., "Active targeting of chemotherapy to disseminated tumors using nanoparticle-carrying T cells" Science Translational Medicine 7.291 (2015): 291ra94-291ra94 (Year: 2015).

Kim et al. "Anti proliferative action of IL 6R-targeted antibody tocilizumab for non-small cell lung cancer cells." Oncology Letters 9.5 (2015): 2283-2288. (Year: 2015).
Lin et al., "Preparation of human transferring adriamycin conjugate and cytotoxic effect of the conjugates in vitro" Tumor 20(4):263-65 (Jul. 2000). English abstract submitted.
O'Dwyer et al., "Uridinediphosphate glucuronosyltransferase (UGT) 1A1 and irinotecan: practical pharmacogenomics arrives in cancer therapy." Journal of Clinical Oncology 24.28 (2006): 4534-4538. (Year: 2006).
PubChem Database. National Center for Biotechnology Information "7-Ethyl-1 O-hydroxycamptothecin" Cl D=104842 https://pubchem.ncbi.nim.nih.gov/compound/7- ethyl-10-hydroxy-camptothecin (accessed on Jul. 15, 2020, created 2005) (Year: 2005).
Simoes et al., "Transfection of human macrophages by lipoplexes via the combined use of transferrin and pH-sensitive peptides" J Leukoc Biol. 65(2):270-79 (Feb. 1999).
Steinfeld et al., "T lymphocytes as potential therapeutic drug carrier for cancer treatment" International Journal of Pharmaceutics 311. 1-2 (2006): 229-236. (Year: 2006).
Trowbridge et al., "CD45: an emerging role as a protein tyrosine phosphatase required for lymphocyte activation and development" Annual Review of Immunology 12.1 (1994): 85-116. (Year: 1994).
Ueno et al., "SN-38 induces cell cycle arrest and apoptosis in human testicular cancer." European Urology 42.4 (2002): 390-397. (Year: 2002).
Klenkar et al., "Natural and synthetic coumarins as potential anticancer agents" Journal of Chemical and Pharmaceutical Research, 7(7):1223-38 (Jan. 2015).
Nielsen et al., "Tumor-infiltrating B cells and T cells: Working together to promote patient survival" OncoImmunology 1(9):1623-25 (Dec. 2012).
Sundararajan et al., "Photorelease of Carboxylic Acids, Amino Acids, and Phosphates from N-Alkylpicolinium Esters Using Photosensitization by High Wavelength Laser Dyes" Journal of the American Chemical Society 127 (22):8000-01 (Jun. 2005).
Gilboa, "DC-based cancer vaccines," J Clin Invest., 2007, 117(5):1195-1203.
Kim et al. "Double-chambered ferritin platform: dual-function payloads of cytotoxic peptides and fluorescent protein." Biomacromolecules 17.1 (published online Dec. 9, 2015): 12-19.
'Shi, Jiahai, et al. "Engineered red blood cells as carriers for systemic delivery of a wide array of functional probes." Proceedings of the National Academy of Sciences, 2014, 111(28): 10131-10136.

\* cited by examiner

Fig. 1

A) Mammalian ferritin H chain (SEQ ID NO: 1 to 7)

```
Ma min       ------------------SEAAXXRQINLELKASYVLSMSXYFDRDDVALRQNFAKYFLHQSHEEREMAEKLMKLQNQRGGRIXLKDIKKPXDWESGLNAMECALXLEKX
Ma_Fer_H     MTTASXSQVRQNYXQXSEAAXXRQINLELXASYVLSMSXYFDRDDVALRQNFAKYFLHQSHEEREHAEKLMKLQNQRGGRIXLKDIKKPDDWESGLNAMECALHLEKX
Mu min Fer H ------------------AEAAINRQINLELYASYVLSMSXYFDRDDVALRNFAKYFLHQSHEEREHAEKLMKLQNQRGGRIFLQDIKKPDRDDWESGLNAMECALHLEKS
Mu_Fer_H     MTTASPSQVRQNYHQDAEAAINRQINLELYASYVLSMSCYFDRDDVALRNFAKYFLHQSHEEREHAEKLMKLQNQRGGRIFLQDIKKPDDDWESGLNAMECALHLEKS
H min Fer H  ------------------SEAA NRQINLELYASYVLSMSYYFDRDDVALKNFAKYFLHQSHEEREHAEKLMKLQNQRGGRIFLQDIKKPDCDDWESGLNAMECALHLEKN
H Fer H      MTTASTSQVRQNYHQDSEAA NRQINLELYASYVLSMSYYFDRDDVALKNFAKYFLHQSHEEREHAEKLMKLQNQRGGRIFLQDIKKPDCDDWESGLNAMECALHLEKN
                                :.***     ..*****:********** *******:**************  ***************    ********: *****:****

Ma min       VNQSLLELHKLATDKNDPHLCDFIETXYLXEQVKXIKEL----------------       (SEQ ID NO: 1)
Ma_Fer_H     VNQSLLELMLKLATDKNDPHLCDFIETYXLKEQVKXIKELGDHVTNLRKMGAFEXGXAEYLFDKHTLGXSDXXX         (SEQ ID NO: 2)
Mu min Fer H VNQSLLELHKLATDKNDPHLCDFIETYLSEQVKSIKEL---------------      (SEQ ID NO: 3)
Mu_Fer_H     VNQSLLELHKLATDKNDPHLCDFIETYYLSEQVKSIKELGDHVTNLRKMGAFEACAFEAGMAEYLFDKHTLGHCDES         (SEQ ID NO: 4)
H min Fer H  VNQSLLELHKLATDKNDPHLCDFIETHYLNEQVKAIKEL---------------      (SEQ ID NO: 5)
H Fer H      VNQSLLELHKLATDKNDPHLCDFIETHYLNEQVKAKELGDHVTNLRKMGAPESCLAEYLFDKHTIGDSDNES         (SEQ ID NO: 6)
             *****:******** ********:** ******* ***
```

MTTASXSQVR QNYXQXSEAA XRQINLELX ASYVLSMSY YFDRDDVALK NFAKYFLHQS HEEREHAEKL MKLQNQRGGR IWLXDIKKPD CDDWESGLNA MECALXLEKNVN QSLLELHKLA TDKNDPHLCD FIETHYLNEQ VKXIKELGDH VTNLRKMGAP ESGLAEYLFD KHTLGDSDX XX (SEQ ID NO: 7)

B) Mammalian ferritin L chain (SEQ ID NO: 8 to 14)

```
Ma min       --------NYSTXVEAAVNXLVNLHLRASYTYLSLGXXFDRDDVALEGVXHFFRELAEEKREGKXERLLXXQNXRGGRALFQDMXXKPXXDEWGKTXXAMGXAXAXENXNLNQA
Ma_Fer_L     MTSQIRQNYSTXVEAAVNXLVNLHLRASYTYLSLGXXFDRDDVALEGVXHFFRELAEEKREGKERLLXXQNXRGGRALFQDXXXKFXXDEWGKTXXAMXAXAXEXKNLNQA
Mu_min Fer L ---------NYSTEVEAAVNRLVNLHLRASYTYLSLGFFFDRDDVALEGVGHFFRELAEEKREGAERLLEFQNDRGGRALFQDVQKFSQDEWGKTQEAMEPAALAMEKNLNQA
Mu_Fer_L     MTSQIRQNYSTEVEAAVNRLVNLHLRASYTYLSLGFFFDRDDVALEGVGHFFRELAEEKREGAERLLEFQNDRGGRALFQDVQKFSQDEWGKTQEAMEPAALAMEKNLNQA
H min Fer L  ---------NYSTDVEAAVNSLVNLYLQASVTYLSLGFYFDRDDVALEGVSHFFRELAEEKREGYERLLKMQNQRGGRALFQDIKKPAEDEWGKTPDAMKAAMALEKKLNQA
H Fer L      MSSQIRQNYSTDVEAAVNSLVNLYLQASVTYLSLGFYFDRDDVALEGVSHFFRELAEEKREGYERLLKMQNQRGGRALFQDIKKPAEDEWGKTPDAMKAAMALEKKLNQA
             *:.*****::**:**::*:**  *:***.***************.***************.**** ::*:*:** **** **      ***: *  : *:

Ma min       LLDLHALGSARKDFHXCDFLEXHXLDXEVKLIKKMGXHLTNLRXAG--------       (SEQ ID NO: 8)
Ma_Fer_L     LLDLHALGSARXDPHXCDFLEXHXLDXEVKLIKKMGXHLTNLRXAGPGPXQXGXVQXSLGEYLFERLTLKHD          (SEQ ID NO: 9)
Mu min Fer L LLDLHALGSARADPHLCDFLESHYLDKEVKLIKKMGMHLITNLRRVAG--------       (SEQ ID NO: 10)
Mu_Fer_L     LLDLHALGSARADPHLCDFLESHYLDKEVKLIKKMGNHLTNLRRVAGPQPAQTGAPQGSLGEYLFERLTLKHD          (SEQ ID NO: 11)
H min Fer L  LLDLHALGSARTDPHLCDFLETHFLDEVVKLIKKMGDHLITNLRLG---------      (SEQ ID NO: 12)
H Fer L      LLDLHALGSARTDPHLCDFLETHFLDEEVKLIKKMGDHLTNLHRLGGPE--------AGIGEYLFERLITLKHD          (SEQ ID NO: 13)
             *******.*:.**:***:***:*:*: *:****** ** **:   .                ****::**:*
```

MTSQIRQNYS TEVEAAVNRL VNLHLRASYT YLSLGXXFDR DDVALEGVGH FFRELAEEKR EGAERLLKLQ NQRGGRALFQ DVQKPAQDEW GKTXEAMEAA LALEKNLNQAL LDLHALGSAR TDPHXCDFLE NHFLDXEVKL IKKMGXHLTN LRRLAGPQPX QXGVXQXSLG EYLFERLTIK HD (SEQ ID NO: 14)

Fig. 1 continued

C) Mammalian haemoglobin alpha chains (SEQ ID NO: 15 to 18)

```
Ma_min_                ------------------VGAHXGEYXAEALEKMFLSFXXTKTYFPHFDLSHGSAXVKEHGKKVXHGKKVAXXLTNAVAHVDXXPNALSALXDLMAHKLXVDXVNFKLLSHCLXXTL
Ma_aHem                XXLSPADKTNVKAAWGKVGAHXGEYXAEALEKMFLSFXXTKTYFPHFDLSHGSAXVKEHGKKVAXXLTNAVAHVDXXPNALSALKDLHAHKLXVDXVNFKLLSHCLXXTL
H_min_aHem             ------------------VGAHXGEYGAEALERMPLSPTTKTYFPHFDLSHGSAQVKGHGKKVADALTNAVAHVDDMPNALSALSDLHAHKLRVDPVNFKLLSHCLLVTL
H_aHem                 MVLSPADKTNVKAAWGKVGAHAGEYGAEALERMFLSFTTKTYFPTTKTYFPHFDLSHGSAQVKGHGKKVADALTNAVAHVDDMPNALSALSDLHAHKLRVDPVNFKLLSHCLLVTL
                                         **** *** ****** ******* ***** ******** ** ****** ***** *** ************ ** ************  **

Ma_min_                XAHLPAEFXPAVHAXLDKFLASVX--------     (SEQ ID NO: 15)
Ma_aHem                XAHLPAEFXPAVHAXLDKFLASVXTVLTSNYX     (SEQ ID NO: 16)
H_min_aHem             AAHLPAEFTPAVHASLDKFLASVS--------     (SEQ ID NO: 17)
H_aHem                 AAHLPAEFTPAVHASLDKFLASVSTVLTSNYR     (SEQ ID NO: 18)
                       ******** ***** ********
```

D) Mammalian haemoglobin beta chains (SEQ ID NO: 19 to 22)

```
Ma_min_bHem            ------------GKVXXVDEVXXEXXAXLLVVYPWTQRFXESFGDLSXXDAVMGNPKVKAHXKKKLGAFSDGLAHLDNXKXXFAILSELHCDKLHVDPXNFRLLGNV
Ma_bHem                MVHLTPEEKAXVTAXWGKVXVDEVXXEXXAXLLVVYPWTQRFXESFGDLSXXDAVMGNPKVKAHXKKKLGAFSDGLAHLDNXKXXFAILSELHCDKLHVDPXNFRLLGNV
H_min_bHem             ------------GKVNVDEVGGEALGRLLVVYPWTQRFLESFGDLSTPDAVMGNPKVKAHGKKVLGAFSDGLAHLDNLKGTFATLSELHCDKLHVDPENFRLLGNV
H_bHem                 MVHLTPEEKSAVTALWGKVNVDEVGGEALGRLLVVYPWTQRFLESFGDLSTPDAVMGNPKVKAHGKKVLGAFSDGLAHLDNLKGTFATLSELHCDKLHVDPENFRLLGNV
                                   *** ****  *     *  *********** ********** **********   ***************  *   ******************

Ma_min_bHem            LVCVLAHHFGKEFTPPVQAAYQKVVAAXAN------     (SEQ ID NO: 19)
Ma_bHem                LVCVLAHHFGKEFTPPVQAAYQKVVAAXANALAHKYX     (SEQ ID NO: 20)
H_min_bHem             LVCVLAHHFGKEFTPPVQAAYQKVVAGVAN------     (SEQ ID NO: 21)
H_bHem                 LVCVLAHHFGKEFTPPVQAAYQKVVAGVANALAHKYH     (SEQ ID NO: 22)
                       **********************     **
```

E) Mammalian transferrins (SEQ ID NO: 23 to 28)

```
Ma_Transferrin_N       MXLAVGALXXCAVLXICLAVPDKXXRWCAVXXHEATKCQSFXDHMKKVIPSDGPSVACXKRASKXDCIRAXANEAXKVT---------------------------
Ma_Transferrin_C       ---------------------------------------------------------------------------------------------------------
Ma_Transferrin         MXLAVGALXXCAVLXLCAVLXLCLAVPDKXXRWCAVXXRWCAVXXHEATKCQSFXDHMKKVIPSDGPSVACXKRASKXDCIRAXANEAXKVTLDAXLVXXAYLAPXNLKVVAEFXGSHXDPCTFYXXVAVV
H_min_Transferrin_N    MRLAVGALLVCAVLGLCLAVPDKTVRWCAVSEHEATKCQSFRDHMKSVIFSDGPSVACVVKKASYLDCIRAIAANEADAVT--------------------------
H_Transferrin_C        ---------------------------------------------------------------------------------------------------------
H_Transferrin          MRLAVGALLVCAVLGLCLAVPDKTVRWCAVSEHEATKCQSFRDHMKSVIFSDGPSVACVVKKASYLDCIRAIAANEADAVTLDACLVYDAVLAFNNLKPVVAEFYGSKEDPQTFYYAVAVV Ma_Transferrin_N       -----------
Ma_Transferrin_C       -----------
```

Fig. 1 continued

```
Ma Transferrin       XKDXGFQMKQLRGKKSCHTGLGRSAXWNIPIXXLYCDLPEXRKPLEKAVANFFSGSCAXCADGTDFFKLCQLCPGCGCSTLNQXPFGYSGAFKCLXDGAGDVAFXKHSTIFENLANKAXPD
H  Transferrin N     ----------------------------------------------------------------------------------------------------------------------
H  Transferrin C     ----------------------------------------------------------------------------------------------------------------------
H  Transferrin       KKDSGFQMNQLRGKKSCHTGLGRSACWNIPICLLYCDLPEPRKPLEKAVANFFSGSCAPCADGTDFPQLCQLCPGCGCCSTLNQYFGYSGAFKCLRDCAGDVAFVKHSTIFENLANKADRD Ma Transferrin N     QYELXCLDNTRKPVXEYXDCHLAQVFSXTVVARSXXGKREDLIWEXXNQAQEHXGKDKSNEFQLFSSPXXXDLLFKDSAHGFLKVFXXMDAKMYLGYXVTAIRNLREGTCPEAPTDXCKP
Ma Transferrin C     ----------------------------------------------------------------------------------------------------------------------
H  Transferrin N     ----------------------------------------------------------------------------------------------------------------------
H  Transferrin C     ----------------------------------------------------------------------------------------------------------------------
H  Transferrin       QYELLCLDNTRKFVDEYKDCHLAQVPSHTVVARSMGGKREDLIWELLNQAQEHPGKDKSKEFQLFSSPHGKDLLFKDSAHGFLKVFPRMDAKMYLGYEVTAIRNLREGTCPEAPTDECKP Ma Transferrin N     --------ETXEDCIAKIMNGEAXAXXLDGXFXYIKGXCGLVPVLAENYNKSDNCEDTPEAGYFAVAVXKKSASDLTWDNLKXKKXCHTAVGRTAGWN
Ma Transferrin C     VKWCALSHHERLKCDEWSVNXVGKIFCVSAETXEDCIAKIMNGEAXAXXLDGXFXYIXGXCGLVPVLAENYNKSDNCEDTPEAGYFAVAVXXKSASDLTWDNLKIKKXCHTAVGRTAGWN
H  Transferrin N     ---------FITEDCIAKIMNGEADAMSLDGGFVYIAGKCGLVPVLAENYNKSDNCEDTPEAGYFAVAVVKKSASDLTWDNLKGKKSCHTAVGRTAGWN
H  Transferrin C     VKWCALSHHERLKCDEWSVNSVGKIFCVSAETTEDCIAKIMNGEACAMSLDGGFVYIAGKCGLVPVLAENYNKSDNCEDTPEAGYFAVAVVKKSASDLTWDNLKGKKSCHTAVGRTAGWN Ma Transferrin N     IPMGLXXNKINHCPXDFFXEGCA-------------------------------------
Ma Transferrin C     IPMGLXXMNKINHCRXDXFFXEGCAXGSKXDSSICKLCMSGLNLCEPNXKEGYYGXTGAFRCLVEKGDVAFVMQTVXXNTGKXNPDFWAKNLNENDVELLCLDGXRKPVEXYANCHLAR
H  Transferrin N     IPMGLLYNKINHCRPDEFFSEGCA-------------------------------------
H  Transferrin C     IPMGLLYNRKINHCRFDEFFSEGCAPGSKKDSSICKLCMCSGLNLCEPNNKEGYYGYTGAFRCIVEKGDVAFVKHQTVPQNTGGKNPDFWAKNLNEKDYELLCLDGTRKPVEEYANCHLAR Ma Transferrin N     ---------------------------------------------                 (SEQ ID NO: 23)
Ma Transferrin C     ---------------------------------------------                 (SEQ ID NO: 24)
Ma Transferrin       APXHAVXTRKDKEACVHKILRXQQHLFGSNVTDCXGNFCLFRSETNDXLFRXDTVCLAKLHDRNTYERYLGEEVVKAXGNLRKCSTSSLLEXCTFXPX----  (SEQ ID NO: 25)
H  Transferrin N     ---------------------------------------------                 (SEQ ID NO: 26)
H  Transferrin C     ---------------------------------------------                 (SEQ ID NO: 27)
H  Transferrin       APNHAVVTRKDKEACVHKILRQQQHLFGSNVTDCSGNFCLFRSETKDLLFRDDTVCLAKLHDRNTYEKYLGEEYVKAVGNLRKCSTSSLLEACTFRRP      (SEQ ID NO: 28)
```

Fig. 8
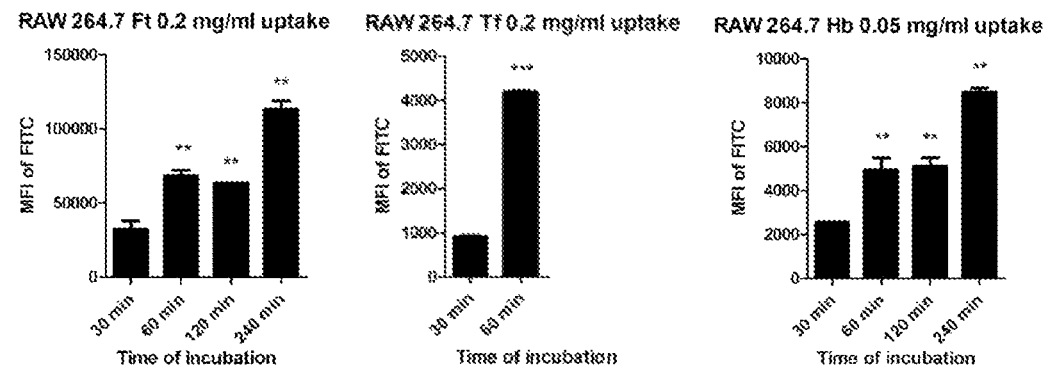
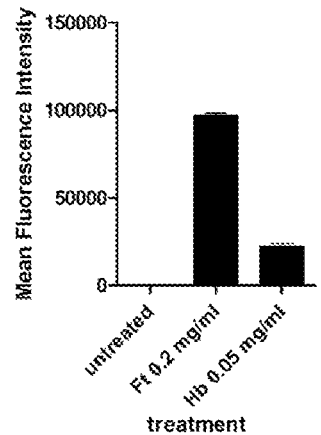
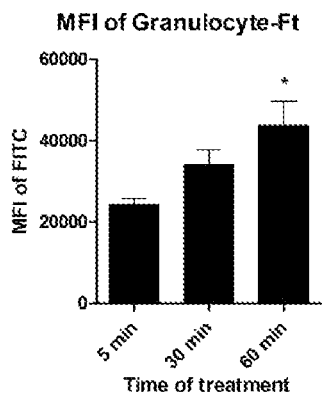 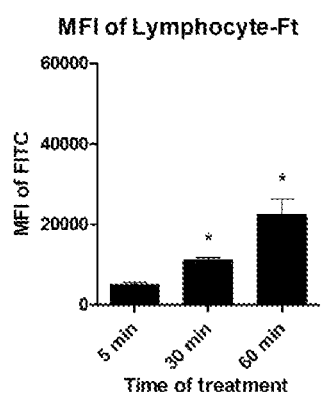

Fig. 9
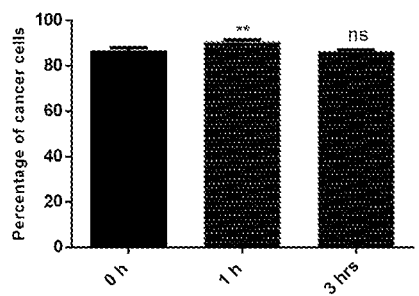
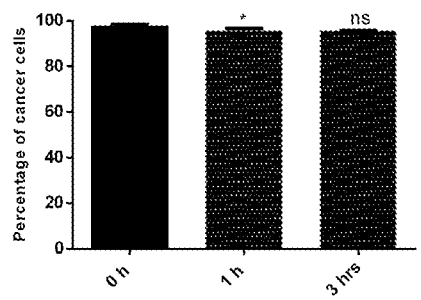
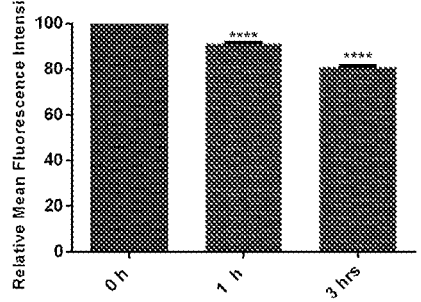
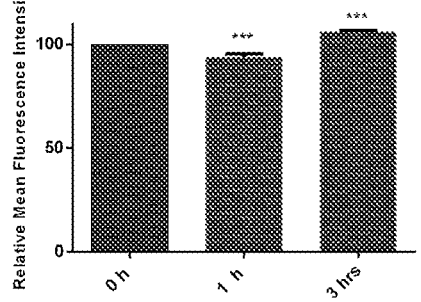

Fig. 12
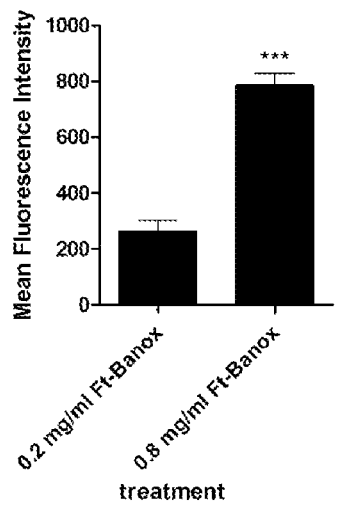
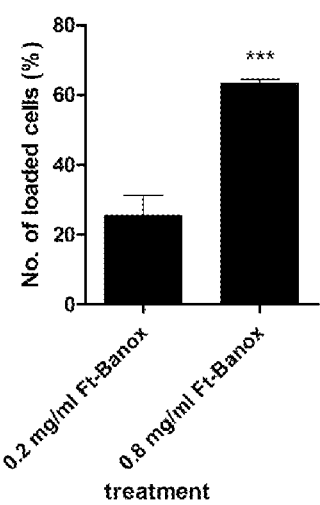

CELLULAR TARGETED ACTIVE INGREDIENT DELIVERY SYSTEM

CROSS-REFERENCE TO RELATED APPLICATION

This application is a U.S. national phase of International Patent Application No. PCT/EP2016/064484 filed Jun. 22, 2016, which claims priority to Poland Patent Application No. 412787 filed Jun. 22, 2015, both of which are hereby incorporated by reference in their entirety.

The present invention relates to an isolated cellular targeted delivery system comprising a $CD45^+$ leukocyte cell comprising within said cell a complex of one or more iron binding proteins and an active ingredient as well as methods for producing such isolated cellular targeted delivery system and uses of such system for therapy, in particular for therapy of cancer.

BACKGROUND OF THE INVENTION

Current imaging tools are capable of detecting large metastases (larger than 0.5-1 cm in size). However, they rarely detect the early spread of metastatic tumour cells. Human metastases smaller than 0.5 cm are avascular so without proper blood and oxygen supply. It means that the delivery of contrast agents through the blood circulation for the purpose of labelling these metastases and imaging them is not possible. The presence of hypoxia is a common characteristic of micrometastases where hypoxic fraction may be as high as 90% with little or no blood perfusion (Li, et al. 2012, Journal of Solid Tumours, 2(2): 28-33). Thus, severe hypoxia is considered as a general feature of micrometastases.

The targeting of one or more micrometastases hidden within a large population of normal cells presents a unique challenge since access to the micrometastases is impeded by several bio-barriers, poor blood supply, further obstacles are presented by small size of the micrometastases and their dispersion to organs.

For the same reason micrometastases are often refractory to therapy. While the solid tumours from which the micrometastases have originated often respond well to conventional therapy there is often regrowth at the site of the primary tumour or at sites of metastasis. This constitutes a serious problem in clinical oncology (Muthana, et al. 2012, Cancer Res; 73(2); 490-495). It is related to characteristics of the microenvironment of solid tumours that limit drug penetration, thereby exposing the tumour to lower than efficacious concentrations of drugs (Hobbs, et al. 1998, Proc Natl Acad Sci USA: 4607-4612). This is caused by inadequate vasculature resulting in: high heterogeneity of cancer cells, low oxygen tension (hypoxia), low pH and low glucose concentration within the mass (Kizaka-Kondoh, et al., 2003, Cancer Sci 94(12):1021-1028). Additionally, rapid tumour cell proliferation in some areas might outpace the rate of new blood vessel growth, promoting formation of hypoxic area (Lewis and Murdoch, 2005, Am J Pathol 167(3):627-635). This abnormal vessel architecture and, subsequently, their impaired function resulting in tumour hypoxia is associated with a more malignant phenotype and poor survival in patients suffering from solid tumours and results in both treatment failure due to decreased drug uptake and hypoxia-inducible changes in cancer cells (Sun, et al., 2012, Clin Cancer Res 18(3):758-770; Sullivan, et al., 2008 Mol Cancer Ther 7(7):1961-1973; Kizaka-Kondoh, et al., 2003, Cancer Sci 94(12):1021-1028). Moreover, chemotherapy or radiotherapy causes additional formation of large areas of tumour hypoxia thus making the treatment of tumour even more difficult. The fact that the efficacy of anticancer therapy is limited by the presence of hypoxic tumour cells has resulted in the introduction of variety of therapeutic approaches aimed at overcoming this problem.

The present inventors have discovered that $CD45^+$ leukocyte cells, in particular activated macrophages, can uptake active ingredients complexed with one or more iron binding proteins in vitro and deliver these complexes to or into cells, preferably to or into tumour cells in vivo. Based on this observation the present inventors have overcome one or more of the above stated problems of the prior art. Thus, the targeted delivery system of the present invention provides inta alia one or more of the following advantages: (i) specific delivery of one or more active ingredients to tissues that attract above mentioned $CD45^+$ leukocytes, preferably into diseased cells, (ii) protection of active ingredients from inactivation in the blood circulation or clearance from the body, (iii) delivery of active ingredients to, preferably into cells of poorly or non-vascularized areas of disease, e.g. metastases, hypoxic areas within larger tumours, rheumatic lesions, avascular wounds, skin, (iv) reduced toxicity of active ingredient, (v) delivery of active ingredients with poor pharmacokinetics, (vi) reduced side effects of the drugs due to their targeted delivery, (vii) higher treatment efficacy with lower doses of the drugs due to targeted delivery; and/or (viii) lower risk of local tissue injury at the site of drug administration due to administration of the drug linked with iron-binding protein, which is loaded inside the $CD45^+$ leukocyte (Pérez-Herrero E, Fernindez-Medarde A. 2015, Eur J Pharm Biopharm 93:52-79).

SUMMARY OF THE INVENTION

In a first aspect the present invention relates to an isolated targeted delivery system comprising a $CD45^+$ leukocyte cell, which is preferably capable of internalizing an iron binding protein comprising within said cell a complex of one or more iron binding proteins and one or more active ingredients.

In a second aspect the present invention relates to a method of preparation of the isolated targeted delivery system of the first aspect of the invention comprising steps of:
  a) providing, preferably purified, iron binding protein;
  b) covalently or non-covalently linking an active ingredient to and/or encapsulating an active ingredient in an iron binding protein;
  c) providing a $CD45^+$ leukocyte cell; and
  d) incubating the $CD45^+$ leukocyte cell in the presence of the complex of the iron binding protein and the active ingredient produced in step b) until the $CD45^+$ leukocyte cell is at least partially loaded with the complex of the iron binding protein and the active ingredient produced in step b).

In a third aspect the present invention relates to an isolated targeted delivery system of the first aspect of the invention for use as a medicament.

In a fourth aspect the present invention relates to a pharmaceutical composition comprising the isolated targeted delivery system of the present invention and a pharmaceutically acceptable carrier and/or suitable excipient(s).

In a fifth aspect the present invention relates to an isolated targeted delivery system of the first aspect of the present invention for use in preventing/treating tumours, preferably a solid tumour, preferably breast cancer, pancreatic cancer, bladder cancer, lung cancer, colon cancer, or a tumour having hypoxic areas, inflammatory disease or ischemic areas, in particular in skin wounds or after organ infarctus (heart) or ischemic retina.

DETAILED DESCRIPTION OF PREFERRED EMBODIMENTS

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

The term "targeted drug delivery" refers to the delivery of an active ingredient to a patient which results in an increased concentration of the active ingredient in a particular region of the body when compared to other regions of the body of that patient. Preferably, the relative concentrations are compared between the diseased region(s) of the body and other regions of the body having similar access to the blood circulation. In preferred embodiments the concentration of the active ingredient in a given number of cells or a given biopsy volume from the diseased region is at least 10% higher, if compared to the identical number of cells or biopsy volume from a non-diseased region after administration of the targeted delivery system of the present invention, preferably after 2-24 hrs. More preferably, the concentration of the active ingredient in the diseased region of the body of a patient is at least 20%, at least 30%, at least 40%, at least 50%, at least 60%, at least 70% at least 80%, at least 90%, at least 100%, at least 150%, at least 200%, at least 250%, at least 300%, at least 350%, at least 400%, at least 450%, at least 500%, more preferably at least 1000% higher than in a non-diseased region of the body after administration of the targeted delivery system of the present invention, preferably after 2-24 hrs. When assessed on the basis of total body distribution it is preferred that at least 5% of the active ingredient administered to a patient is delivered to the diseased region of the body, preferably at least 10%, more preferably at least 15%. The targeted delivery of the active ingredient limits the potential deleterious effects of an active ingredient to the diseased region of the body.

The terms "targeted drug delivery system" or "targeted delivery system" are used synonymously in the present application and refer to a system that is capable of delivering an active ingredient to the targeted region, i.e. of capable of targeted delivery, preferably within the body of a patient.

The terms "active ingredient" or "drug" are used synonymously in the context of the present invention and refer to any compound that modifies or modulates cell activity or is capable of being activated, i.e. a prodrug, to modify or modulate cell activity, preferably in the body of a patient. Examples of such active ingredients include so called "small molecules" and peptides. The term "small molecule" is used in the context of the present invention to refer to a hydrocarbon with a molecular mass of below 1.500 g/mol or to pharmaceutically active radioactive isotopes. Preferred, drugs that can be used comprise anticancer drugs, pharmaceutically active radioactive isotopes or ferrihydrite.

The term "prodrug" as used in the context of the present invention refers to any active ingredient that, after administration, is metabolized or otherwise converted to a biologically active or more active ingredient (or drug) with respect to at least one property. In comparison to the drug, a prodrug is modified chemically in a manner that makes it, relative to the drug, less active or inactive, but the chemical modification is such that the corresponding drug is generated by metabolic or other biological processes after the prodrug is administered to the patient. A prodrug may for example have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

The terms "polynucleotide" and "nucleic acid" are used interchangeably herein and are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as e.g. RNA-DNA hybrids. The nucleic acids, can e.g. be synthesized chemically, e.g. in accordance with the phosphotriester method (see, for example, Uhlmann, E. & Peyman, A. (1990) Chemical Reviews, 90, 543-584). "Aptamers" are nucleic acids which bind with high affinity to a polypeptide. Aptamers can be isolated by selection methods such as SELEmir146-a (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability.

The term "peptide" or "polypeptide" is used interchangeably in the context of the present invention to refer to a chain of at least two amino acids linked by peptide bonds. Thus, the term "peptide" in the context of the present invention is also used to refer to amino acid chains with more than 50, more than 100 or more than 150 amino acids.

The term "antibody" as used in the context of the present invention refers to a glycoprotein belonging to the immunoglobulin superfamily; the terms antibody and immunoglobulin are often used interchangeably. An antibody refers to a protein molecule produced by plasma cells and is used by the immune system to identify and neutralize foreign objects such as bacteria and viruses. The antibody recognizes a unique part of the foreign target, its antigen.

The term "antibody fragment" as used herein, refers to one or more fragments of an antibody that retain the ability to specifically bind to an antigen. Examples of binding fragments encompassed within the term "antibody fragment" include a fragment antigen binding (Fab) fragment, a Fab' fragment, a F(ab')$_2$ fragment, a heavy chain antibody, a single-domain antibody (sdAb), a single-chain fragment variable (scFv), a fragment variable (Fv), a V$_H$ domain, a V$_L$ domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, an alternative scaffold protein, and a fusion protein thereof.

The term "diabody" as used within this specification refers to a fusion protein or a bivalent antibody which can bind different antigens. A diabody is composed of two single protein chains which comprise fragments of an antibody, namely variable fragments. Diabodies comprise a heavy chain variable domain (V$_H$) connected to a light-chain variable domain (V$_L$) on the same polypeptide chain (V$_H$-V$_L$, or V$_L$-V$_H$). By using a short peptide connecting the two variable domains, the domains are forced to pair with the complementary domain of another chain and thus, create two antigen-binding sites. Diabodies can target the same (monospecific) or different antigens (bispecific).

A "single domain antibody", refers to antibody fragments consisting of a single, monomeric variable domain of an antibody. Simply, they only comprise the monomeric heavy chain variable regions of heavy chain antibodies produced by camelids or cartilaginous fish. Due to their different origins they are also referred to VHH or VNAR (variable new antigen receptor)-fragments. Alternatively, single-domain antibodies can be obtained by monomerization of variable domains of conventional mouse or human antibodies by the use of genetic engineering. They show a molecular mass of approximately 12-15 kDa and thus, are the smallest antibody fragments capable of antigen recognition. Further examples include nanobodies or nanoantibodies.

The term "antibody mimetic" as used within the context of the present specification refers to compounds which can specifically bind antigens, similar to an antibody, but are not structurally related to antibodies. Usually, antibody mimetics are artificial peptides or proteins with a molar mass of about 3 to 20 kDa which comprise one, two or more exposed domains specifically binding to an antigen. Examples include inter alia the LACI-D1 (lipoprotein-associated coagulation inhibitor); affilins, e.g. human-γ B crystalline or human ubiquitin; cystatin; Sac7D from *Sulfolobus acidocaldarius*; lipocalin and anticalins derived from lipocalins; DARPins (designed ankyrin repeat domains); SH3 domain of Fyn; Kunits domain of protease inhibitors; monobodies, e.g. the 10$^{th}$ type III domain of fibronectin; adnectins: knottins (cysteine knot miniproteins); atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric or trimeric human C-type lectin domain; microbodies, e.g. trypsin-inhibitor-II; affilins; armadillo repeat proteins. Nucleic acids and small molecules are sometimes considered antibody mimetics as well (aptamers), but not artificial antibodies, antibody fragments and fusion proteins composed from these. Common advantages over antibodies are better solubility, tissue penetration, stability towards heat and enzymes, and comparatively low production costs.

The term "sequence identity" is used throughout the specification with regard to polypeptide and nucleotide sequence comparisons. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a polypeptide sequence consisting of 200 amino acids compared to a reference 300 amino acid long polypeptide sequence may exhibit a maximum percentage of sequence identity of 66.6% (200/300) while a sequence with a length of 150 amino acids may exhibit a maximum percentage of sequence identity of 50% (150/300). If 15 out of those 150 amino acids are different from the respective amino acids of the 300 amino acid long reference sequence, the level of sequence identity decreases to 45%. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl-?page=/NPSA/npsaclustalw.html. Preferred parameters used are the default parameters as they are set on http://www.ebi-.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). BLAST protein searches are performed with the BLASTP program, score=50, word length=3. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. Structure based alignments for multiple protein sequences and/or structures using information from sequence database searches, available homologs with 3D structures and user-defined constraints may also be used (Pei J, Grishin N V: PROMALS: towards accurate multiple sequence alignments of distantly related proteins. Bioinformatics 2007, 23:802-808; 3DCoffee@igs: a web server for combining sequences and structures into a multiple sequence alignment. Poirot O, Suhre K, Abergel C, O'Toole E, Notredame C. Nucleic Acids Res. 2004 Jul. 1; 32:W37-40). When percentages of sequence identity are referred to in the present application, these percentages are calculated in relation to the full length of the longer sequence, if not specifically indicated otherwise.

The term "leukocyte" is used in the context of the present invention to refer to cells of the immune system that are involved in protecting the body against both infectious disease and foreign invaders. All leukocytes are produced and derived from multipotent cells in the bone marrow known as a hematopoietic stem cells. Leukocytes are found throughout the body, including the blood and lymphatic system. All leukocytes have nuclei, which distinguishes them from the other blood cells, the anucleated red blood cells (RBCs) and platelets. Types of leukocyte can be classified in standard ways. Two pairs of the broadest categories classify them either by structure (granulocytes or agranulocytes) or by cell division lineage (myeloid cells or lymphoid cells). These broadest categories can be further divided into the five main types: neutrophils, eosinophils, basophils, lymphocytes, and monocytes. These types are distinguished by their physical and functional characteristics. Monocytes and neutrophils are phagocytic. Further subtypes can be classified; for example, among lymphocytes, there are B cells, T cells, and NK cells. Granulocytes are distinguished from agranulocytes by their nucleus shape (lobed versus round, that is, polymorphonuclear versus mononuclear) and by their cytoplasm granules (present or absent, or more precisely, visible on light microscopy or not thus visible). The other dichotomy is by lineage: Myeloid cells (neutrophils, monocytes, eosinophils and basophils) are distinguished from lymphoid cells (lymphocytes) by hematopoietic lineage (cellular differentiation lineage).

The present inventors have observed that $CD45^+$ expression is characteristic of leukocyte cells that are suitable to be used in the context of the targeted delivery system of the present invention, in particular since $CD45^+$ leukocyte cells are attracted to particular tissues and cells within the body and are capable of delivering complexes of one or more iron binding proteins and one or more active ingredients to or into cells. It is understood by the skilled person that $CD45^+$ leukocyte cells unless of clonal origin are a mixed population of different leukocytes which share the common property of expressing $CD45^+$ surface antigen. Accordingly, subpopulations of cells within the diverse group of $CD45^+$ leukocytes are characterized throughout the specification by further functional and/or structural characteristics. The term "$CD45^+$" indicates that the majority of cells within a population of cells or essentially all cells express the $CD45^+$ surface antigen. In this context and also with reference to other cellular surface antigens, the term "expresses" indicates that the surface antigen is produced within the cell and detectably exposed on the surface of a cell. The level of expression and, thus the number of surface antigens detectably exposed on the surface of a cell can vary greatly among different leukocytes. Generally, a cell is considered to be positive, i.e. is indicated to be "+", for a cellular surface antigen, if at least 5, preferably at least 10 copies of the surface antigen are detectably exposed on the surface of the cell. The skilled person is well aware of how to detect, quantify and select for cells, which are positive (or negative) for a given cellular surface antigen. Preferred methods include Fluorescence Activated Cell Sorting (FACS). In this technology fluorescently labelled antibodies are used to bind to cellular surface antigens of a population of cells, the cells are subsequently isolated into single cells and based on fluorescence intensity measured for the single cell, characterized as being positive or negative for the given cellular surface antigen. In some embodiments of the present invention it is indicated that the expression of a given protein is high or low. This means that the protein is detectably expressed in both instances, i.e. is "+", however, at different levels. High and low expression, respectively, will mean different absolute numbers of proteins per cell for different proteins. Thus, a given protein may be considered to be expressed at high levels if there are more than 500 detectable copies of that protein per cell and to be expressed at low levels if there are between 1 to 50 detectable copies of that protein per cell. However, another protein may be considered to be expressed at high levels, if there are more than 5000 detectable copies and expressed at low levels, if there are between 1 to 500 detectable copies per cell. It is well known in the art how to quantify the number of proteins expressed or produced in a cell using flow cytometry and Becton Dickinson Quantibrite™ bead method (see e.g. Pannu, K. K., 2001, Cytometry. 2001 Dec. 1; 45(4):250-8) or mass spectrometry (see, e.g. Milo, R., 2013, Bioessays, 35(12): 1050-1055). For the purpose of the present invention the term "high expression" of a given protein refers to detectable expression of that protein that is at least 70% of the highest expression level found, i.e. number of copies per cell, in a population of healthy $CD45^+$ leukocytes. The term "low expression" of a given protein refers to detectable expression of that protein that is 30% or less of the highest expression level found, i.e. number of copies of that protein per cell, in a population of healthy $CD45^+$ leukocytes. Preferably, the "highest expression level" is determined as the average of the highest expression levels found in healthy $CD45^+$ leukocytes of different subjects. In some embodiments preferred subpopulations of cells are characterized as "producing" a given protein. This is understood to mean that the protein is not necessarily detectable on the surface of the cell but may only be present inside the cell. The skilled person is well aware how to detect and/or quantify production of a protein inside a cell and/or select cells producing such proteins.

The term "differentiated monocyte" is used in the context of the present invention to refer to a monocyte differentiated from the committed precursor termed macrophage-DC precursor (MDP) mainly resident in bone marrow (but could be also in the spleen) and differentiate into either dendritic cells or macrophages. In mice they consist of two main subpopulations: (i) $CD11b^+$ cell with high expression of CX3CR1, low expression of CCR2 and $Ly6C^-$ and (ii) $CD11b^+$ cell with low expression of CX3CR1, high expression of CCR2 and Ly6C$^+$. After leaving the bone marrow, mouse Ly6C$^+$ monocytes differentiate into Ly6C$^-$ monocytes in circulation. Similarly, in human monocyte differentiation, it is accepted that CD14$^{++}$ classical monocytes leave bone marrow and differentiate into CD14$^{++}$ CD16$^+$ intermediate monocytes and sequentially to CD14$^+$ CD16$^{++}$ non-classical monocytes in peripheral blood circulation (Yang et al. 2014; Biomark Res 2(1) doi. 10.1186/2050-7771-2-1).

Macrophages are tissue-resident professional phagocytes and antigen-presenting cells (APC), which differentiate from circulating peripheral blood monocytes (PBMs). The term "activated macrophage" is used in the context of the present invention to refer to any macrophage that is polarized. Macrophage activation is in general achieved by incubation with interleukins, cytokines and/or growth factors. In particular IL-4 and M-CSF can be used as activating agents. Activated macrophages of different phenotypes are classified into M1-macrophages, classically activated macrophages (CAM) and M2-macrophages, alternatively activated macrophages (AAM). The classically activated M1-macrophages comprise immune effector cells with an acute inflammatory phenotype. These are highly aggressive against bacteria and produce large amounts of lymphokines (Murray, and Wynn, 2011, J Leukoc Biol, 89(4):557-63). The alternatively activated, anti-inflammatory M2-macrophages can be separated into at least three subgroups. These subtypes have various different functions, including regulation of immunity, maintenance of tolerance and tissue repair/wound healing. The term "M1 inducer" is used in the context of the present invention to refer to a compound that directs differentiation of PBMs to macrophages of the M1 type. The term "M2 inducer" is used in the context of the present invention to refer to a compound that directs differentiation of PBMs to macrophages of the M2 type. The skilled person is aware of a large number of ways to promote differentiation into either M1 or M2 macrophages.

The term "phagocytosis by macrophages" is the process by which a macrophage engulfs a solid particle to form an internal vesicle known as a phagosome.

The term "iron binding protein" as used refers to a protein that non-covalently binds an iron ion. Examples of such proteins comprise ferritin, haemoglobin, transferrin; and lactoferrin. Iron binding proteins are bound by cellular surface receptors which facilitate the internalization of these proteins into cells.

In a first aspect the present invention relates to an isolated targeted delivery system comprising a CD45$^+$ leukocyte cell, preferably capable of internalizing an iron binding protein, comprising within said cell a complex of one or more iron binding proteins and one or more active ingredients.

The ability of a given CD45$^+$ leukocyte cell or cell population to internalize iron binding proteins depends on the expression of receptors involved in this internalization process. Receptors that lead to internalization of ferritin comprise, e.g. TfR, CXCR4, CD163, and TIM-2. The skilled person is well aware how to measure the amount of uptake of an iron binding protein and preferred method of measuring the uptake are described in the Example Section below. The present inventors also noted that subpopulations of CD45$^+$ leukocyte cells have a certain propensity to internalize one iron binding protein over another iron binding protein and, thus can attain higher complex concentrations and/or show less leakage of the complex from the cells. Such CD45$^+$ leukocyte subpopulations are described in more detail below.

The phrase "complex of one or more iron binding proteins and an active ingredient" as used in the context of the present invention refers to a composition in which one or more molecules of the active ingredient are covalently or non-covalently bound to one or more iron binding proteins. The covalent or non-covalent binding between the one or more iron binding proteins and the one more active ingredient can be direct or indirect. In the latter case the active ingredient is linked to the iron binding protein via a linker or spacer. Linker or spacers are known to the skilled artisan, such as polyalanine, polyglycin, carbohydrates, $(CH_2)n$ groups or polypeptide linkers. The skilled artisan will, thus, be able to select the respective suitable linker(s) or spacer(s) depending on the respective application. If the iron binding proteins form cages like, e.g. ferritin, than the term "complex" also encompasses the enclosure of active ingredients within the cage even in the absence of a covalent or non-covalent bond between the protein(s) and the active compound(s). The formation of the complex allows the transport of the active ingredient into the cell when the cell is internalizing the iron binding protein. Thus, it is preferred that the active ingredients are bound to the iron binding protein in a way that does not interfere with the transport mechanism. This can be easily tested by the skilled person using uptake assays known in the art and described in the Example Section below. It is preferred that the complex is sufficiently stable to survive the transport within the cell to the target region within the body. Thus, it is preferred that the complex rather than the active ingredient alone is delivered to the cells or into the cells in the target region. This property also reduces possible deleterious effects, e.g. cytotoxicity, of the active ingredient to the CD45$^+$ leukocyte. If active ingredients are covalently coupled to the iron binding proteins such coupling is preferably through amino acids residues known to be located in surface areas that are not involved in binding to the cellular receptors required for cellular uptake of the iron binding proteins. Iron binding proteins used in the context of the present invention can form stable non-covalently bound complexes with a wide variety of active ingredients.

The CD45$^+$ leukocyte originate from the patient to be treated in such case the cell loaded with the complex would be autologous to the patient. It is also envisioned that patients are MHC typed prior to treatment with the targeted delivery of the present invention and that the leukocyte cell type used for a given patient is MHC matched to the patient. In these two preferred embodiments the CD45$^+$ leukocyte is a primary cell or derived by a low number of differentiation steps from a primary cell. Alternatively, the CD45$^+$ leukocyte may be from an immortalized but preferably non-transformed CD45$^+$ leukocyte cell line. Thus the blood used for CD45$^+$ leukocyte, preferably macrophage isolation is preferably obtained from the patient to be treated or healthy donor. Alternatively the blood can be obtained from the blood bank. Use of umbilical cord blood is also considered herein.

The present inventors noted that a subpopulation of CD45$^+$ leukocytes, which are producible from a CD34$^+$ hematopoietic precursor cell are particular suitable for target specific delivery of the active ingredient. Accordingly, it is preferred that the leukocytes used to produce the target delivery system are derived from CD34$^+$ hematopoietic precursor cells. The skilled person is well aware how to select CD34$^+$ hematopoietic precursor cells and how to differentiate such cells into leukocytes.

Preferably, the CD45$^+$ leukocyte is selected from the group consisting of a monocyte, a differentiated monocyte, lymphocyte and a granulocyte. Preferred subpopulations in these general categories of leukocytes are defined in the following by structural parameters, e.g. presence or absence of a given protein, functional properties and/or method of their production/differentiation. As outlined above, the targeted delivery system of the present invention still provides the advantages outlined above, if in a population of cells not every cell has a particular property in as long as the majority of cells within that population has that property. Thus, in the following the property of one preferred cell of the targeted delivery system of the present invention is described. It is appreciated by the skilled person that a pharmaceutical composition of the present invention will comprises millions of cells and that not every cell within the population will have the functional and/or structural properties outlined herein but that the pharmaceutical composition can nevertheless be used to treat a disease, if the majority of cells share the respective functional and/or structural properties.

The present inventors have recognized that subpopulations of CD45$^+$ leukocytes have particular advantageous properties including among others efficiency and/or amount of complex uptake in general, ability to retain the complex within the cell, i.e. to avoid leakage and of target release of the active ingredient, efficiency of uptake of a particular iron binding protein and/or targeting to particular tissues or cells and, thus suitability to treat or ameliorate a particular disease. The present inventors have, e.g. observed that CD45$^+$ leukocytes, which express one or more of the following antigens: CD204, CD206, CD200R, CCR2 have a preference for ferritin uptake over the uptake of other iron binding proteins. Thus, if the iron binding protein in the complex is ferritin it is preferred to select CD45$^+$ leukocytes that express one or more of the following antigens: CD204, CD206, CD200R, CCR2.

Accordingly, in a preferred embodiment of the present invention (i) the monocyte is a CD11b$^+$ monocyte, preferably selected from the group consisting of a CD11b$^+$ CD14$^+$ monocyte, a CD11b$^+$ CD16$^+$ monocyte, a CD11b$^+$ CD14$^+$ CD16$^+$ monocyte, a CD11b$^+$ CD14$^+$ MHCII$^+$ monocyte, a CD11b$^+$ CD14$^+$ CD115$^+$ monocyte, CD11b$^+$ CD114$^+$ monocyte, CD11b$^+$ CD116$^+$ monocyte, CD11b$^+$ CCR1$^+$ monocyte, CD11b$^+$ CCR2$^+$ monocyte, CD11b$^+$ CX3CR$^+$ monocyte, CD11b$^+$ CXR4$^+$ monocyte, CD11b$^+$ CXR6$^+$ monocyte and a CD11b$^+$ CD14$^+$ CD33$^+$ monocyte;

(ii) the differentiated monocyte is selected from the group consisting of a macrophage, an activated macrophage, preferably a CD11b$^+$ macrophage, more preferably a CD11b$^+$ CD16$^+$ macrophage, CD11b$^+$ CD32$^+$ macrophage, CD11b$^+$ CD64$^+$ macrophage, CD11b CD68$^+$ macrophage, preferably a CD11b$^+$ CD86$^+$ M1 macrophage, preferably producing inducible nitric oxide synthetase (iNOS) and/or secreting interleukin 12 (IL-12) or preferably CD11b$^+$ CCR2$^+$ M2 macrophage, CD11b$^+$ CD204$^+$ M2 macrophage, CD11b$^+$ CD206$^+$ M2 macrophage, CD11b$^+$ CD204$^+$ CD206$^+$ M2 macrophage, CD11b$^+$ Mayor Histocompatibility Complex II$^+$ (MHCII$^+$) (low or hi expression) M2 macrophage, CD11b$^+$ CD200R$^+$ M2 macrophage, CD11b$^+$ CD163$^+$ M2 macrophage or activated macrophage producing and/or secreting Arginase-1 and/or interleukin 10 (IL-10); or a dendritic cell, preferably with expression of CD11b CD11c, CD11b CD80, CD11c CD80, CD11c CD86, CD11c MHCII and CD11c CD123, preferably the differentiated monocyte is not a foam cell expressing Lectin-like oxidized low-density lipoprotein receptor-1 (Lox1$^+$), C-X-C chemokine receptor type 7 (CXCR$^+$) and Nuclear factor (erythroid-derived 2)-like 2 (NRF2$^+$). A foam cell is a type of macrophage that localize to fatty deposits on blood vessel walls, where they ingest low-density lipoproteins and become loaded with lipids giving them a foamy appearance. These cells secrete various substances involved in plaque growth and their death promotes inflammation, thereby contributing to cardiovascular disease;

(iii) monocyte or activated monocyte expressing of at least one chemokine receptor, preferably selected from the group consisting of CCR1, CCR2, CXR4, and CXR6, or at least one growth factor receptor, preferably selected from the group consisting of macrophage colony stimulating factor Receptor (CD115), granulocyte colony stimulating factor Receptor (CD114), and granulocyte-macrophage colony stimulating factor Receptor (consisting of CD116 and CD131); monocytes of these characteristics are particular suitable to treat inflammatory conditions and cancer;

(iv) the lymphocyte is selected from the group consisting of a CD3$^+$ and CD4$^+$ or CD8$^+$ T lymphocyte, or a CD19$^+$, CD20$^+$, CD21$^+$, CD19$^+$ CD20$^+$, CD19$^+$ CD21$^+$, CD20$^+$ CD21$^+$, or CD19$^+$ CD20$^+$ CD21$^+$ B lymphocyte; or (v) the granulocyte is selected from the group consisting of a neutrophil, preferably a CD66b$^+$ neutrophil, an eosinophil and a basophil, preferably a CD193$^+$ eosinophil.

In a preferred embodiment of the targeted delivery system of the present invention the activated macrophage:

(i) is producible by in vitro incubation of a monocyte or macrophage or their precursors with a factor capable of altering expression markers on macrophages, preferably
  (a) with at least one M1 inducer,
  (b) with at least one M2 inducer,
  (c) or with a factor capable of altering the macrophages ability to secrete cytokines, preferably IL-10 and IL-12, chemokines and/or to produce iNOS, arginase or other immunomodulating enzymes; examples of such factors are: activated platelets, IL-4, IL-10, IL-13, immune complex of an antigen and antibody, IgG, heat activated gamma-globulin, glucocorticosteroid, tumour growth factor-β (TGF-β), IL-1R, CC-chemokine ligand 2 (CCL-2), IL-6, Macrophage colony-stimulating factor (M-CSF), peroxisome proliferator-activated receptor γ (PPARγ) agonist, leukocyte inhibitory factor (LIF), adenosine, helminth and fungal infection, lipopolysaccharide (LPS), interferon γ (INF-γ), granulocyte macrophage colony stimulating factor (GM-CSF) and viral and bacterial infection; in this respect it was observed that activation of a monocyte with a M1 inducer, particularly LPS will cause cell to express iNOS, that activation of a monocyte with a M1 inducer, particularly LPS will cause cell not to express Arginase-1, that activation of a monocyte with a M2 inducer, particularly IL-4 will cause cell to express Arginase-1, and that activation of a monocyte with a M2 inducer, particularly IL-4 will cause cell not to express iNOS, (ii) is characterized by expression of at least one of following antigens: CD64, CD86, CD16, CD32, high expression of MHCII, and/or production of iNOS and/or IL-12;

(iii) is producible by in vitro incubation of a monocyte or macrophage with a factor capable of inducing the ability of the macrophage to phagocytose, e.g. IL-18, opsonins (for example complement-derived proteins such as iC3b, immunoglobulin G), calcitonin gene-related peptide (CGRP), lipopolysaccharide (LPS), interferon γ (INF-γ), granulocyte macrophage colony stimulating factor (GM-CSF), viral infection and/or bacterial infection;

(iv) is characterized by expression of at least one of following antigens: CD204, CD206, CD200R; CCR2, transferrin receptor (TfR), CXC-motive chemokine receptor 4

(CXCR4), CD163, and/or T cell immunoglobulin-domain and mucin-domain 2 (TIM-2), and/or show low expression of MHCII; activated macrophages having these properties are particularly suitable for complexes comprising ferritin as the iron binding protein;
(v) has the ability to phagocytose; and/or
(vi) is capable of cytokine secretion, preferably of IL-12, or IL-10, or production of inducible nitric oxide synthetase (iNOS) (or other pro-inflammatory compounds), arginase or other immunosuppressive/anti-inflammatory compounds.

In a preferred embodiment of the targeted delivery system of the present invention the M1 inducer for differentiating macrophages into M1 macrophages is selected from the group consisting of lipopolysaccharide (LPS), interferon γ (INF-γ), granulocyte macrophage colony stimulating factor (GM-CSF) and viral and bacterial infection and the M2 inducer for differentiating macrophages into M2 macrophages is selected from the group consisting of IL-4, IL-10, IL-13, immune complex of an antigen and antibody, IgG, heat activated gamma-globulin, glucocorticosteroid, tumour growth factor-β (TGF-β), IL-1R, CC-chemokine ligand 2 (CCL-2), IL-6, Macrophage colony-stimulating factor (M-CSF), peroxisome proliferator-activated receptor γ (PPARγ) agonist, leukocyte inhibitory factor (LIF), adenosine, helminth and fungal infection.

It has been surprisingly found by the present inventors that both complex loaded M1 macrophages and M2 macrophages are suitable for targeted active agent delivery into hypoxic tissues, preferably a tumour or its metastasis. In general we observed that 3 to 5% of the administered M1 macrophages localized at the tumour site while about 35% of the M2 macrophages showed tumour specific targeting. However, this general advantage of M2 macrophages were offset when using a complex comprising haemoglobin and drug, since significantly larger amounts of this complex could be loaded into M1 macrophages than into M2 macrophages. Generally this specific tropisms makes M2 macrophages more suitable for treating tumour and diseases characterized by hypoxic tissue.

In a preferred embodiment of the targeted delivery system of the present invention the monocyte:
(i) is producible from a $CD34^+$ hematopoietic precursor cell;
(ii) is producible by in vitro incubation of monocytes with at least one inducer, preferably M1 or M2 inducer, more preferably at least one M2 inducer;
(iii) is characterized by expression of at least one of the following antigens: TfR, CD163, TIM-2, CD14, CD16, CD33, and/or CD115;
(iv) is characterized by expression of at least one of the following antigens: TfR, CD163, TIM-2, CXCR4, CD14, and/or CD16; and/or
(v) has the ability to phagocytose.

In this embodiment of the targeted delivery system of the present invention the M1 inducer for differentiating monocytes is selected from the group consisting of LPS, INF-γ, GM-CSF or viral or bacterial infection or the M2 inducer for differentiating monocytes is selected from the group consisting of IL-4, IL-10, IL-13, immune complex of an antigen and antibody, IgG, heat activated gamma-globulins, Glucocorticosteroids, TGF-β, IL-1R, CCL-2, IL-6, M-CSF, PPARγ agonist, Leukocyte inhibitory factor (LIF), cancer-conditioned medium, cancer cells, adenosine and helminth or fungal infection.

It has been surprisingly found by the present inventors that monocytes are suitable for targeted active agent delivery into hypoxic tissues, preferably the tumour or its metastasis while monocytes treated with M2 activators are more suitable for targeted active agent delivery into hypoxic tissues, preferably the tumour or its metastasis. This specific tropisms make monocytes treated with M2 activators more suitable to treating tumour and hypoxic sites.

In a preferred embodiment of the targeted delivery system of the present invention the lymphocyte:
(i) is obtainable from blood, spleen, or bone marrow or is producible from a $CD34^+$ precursor cell as known to the skilled person and also described in the, e.g. Lefort and Kim, 2010, J Vis Exp 40: 2017; Tassone and Fidler, 2012, Methods in Molecular Biology 882: 351-357; Kouro et al. 2005, Current Protocols in Immunology, 66:F22F.1: 22F.1.1-22F.1.9;
(ii) is an immunologically competent lymphocyte;
(iii) expresses antigen specific T cell receptors; and/or
(iv) is characterized by expression of at least one of the following antigens: (a) CD3 and CD4 or CD8 or (b): CD19, CD20, CD21, CD19 CD20, CD19 CD21, CD20 CD21, or CD19 CD20 CD21 antigen, and is preferably capable of producing immunoglobulins.

In a preferred embodiment of the targeted delivery system of the present invention the granulocyte:
(i) is obtainable from blood, spleen or bone marrow or producible from a $CD34^+$ precursor cell as described, e.g. in Kuhs et al. 2015, Curr Protoc Immunol 111:7.23-1-7.23.16; Coquery et al. 2012, Cytometry A 81(9): 806-814; Swemydas and Lionakis 2013, J Vis Exp 77: 50586;
(ii) is characterized by expression of at least one of the following CD66b and/or CD193;
(iii) is a polymorphonuclear leukocyte characterized by the presence of granules in its cytoplasm; and/or
(iii) is characterized by expression of at least one of the following: TfR, CD163, TIM-2, and/or CXCR4.

In a preferred embodiment of the targeted delivery system of the present invention the iron binding protein is selected from the group consisting of ferritin, preferably heavy (H) type ferritin, light (L) ferritin and/or mitochondrial ferritin; haemoglobin, preferably haemoglobin A, haemoglobin AS, haemoglobin SC, haemoglobin C, haemoglobin D, haemoglobin E, haemoglobin F, haemoglobin H; haemoglobin-haptoglobin complex, haemopexin, transferrin; and lactoferrin. The terms ferritin; haemoglobin, preferably haemoglobin A, haemoglobin AS, haemoglobin SC, haemoglobin C, haemoglobin D, haemoglobin E, haemoglobin F, haemoglobin H; haemoglobin-haptoglobin complex, hemopexin, transferrin; and lactoferrin encompass structural variants of the naturally occurring proteins and, thus relates to proteins that have at least 70%, preferably at least 75%, more preferably at least 80%, more preferably at least 85%, more preferably at least 90%, more preferably at least 95% more preferably at least 100% of the ability of the respective wild-type protein to bind iron ion(s). The iron binding proteins used in the context of the present invention are preferably of mammalian, more preferably mouse, rat, dog, ape, in particular, chimpanzee, or human, most preferably of human origin. Consensus sequences of the preferred iron binding proteins used in the context of the present invention are shown in FIG. 1 below. Preferred structural variants are based on the sequences indicated in FIG. 1. The residues marked with X vary among different mammalian ferritins, transferrins, and haemoglobins. The alteration of these residues is not crucial for the ability of the proteins to bind to iron ions. Accordingly, it is preferred that amino acid mutations or deletions effect one or more of the residues marked with an X.

Plasma proteins have always been privileged carriers for the delivery of active pharma ingredients in cancer therapy. Thus, albumin, the most abundant plasma protein, is currently used in therapeutic protocols for the delivery of taxane molecules and doxorubicin derivatives (Larsen M T et al. 2016, Mol Cell Ther 27; 4:3).

Human transferrin and ferritin proteins have been considered as effective carriers for the delivery of small molecules or toxin-conjugates to specifically target cancer cells. To date, in spite of considerable efforts, no successful transferrin or ferritin drug complexes have however reached the clinic (Luck A N et al. 2013, Adv Drug Deliv Rev 65(8):1012-9).

Ferritin has a cage architecture and capability of iron-binding which could be used to encapsulate drugs inside its cavity. Ferritins are not abundant in plasma, but can be readily produced in high yield as recombinant proteins in common protein expression vectors such as *Escherichia coli* cells. Ferritins H- or L-chains are encoded as small protein monomer (21 kDa and 19 KDa for H and L chains, respectively) capable of a 24-mer assembly into a cage-like structure, delimiting a 8 nm diameter cavity. The present inventors noted in the context of working on the present invention that H-ferritin homopolymers, represent a preferred protein construct in order to specifically deliver encapsulated drugs to CD45$^+$ leukocyte cells expressing TfR. Furthermore H-ferritin targets complex active ingredients to the cell nucleus (and therefore directly delivers DNA-binding proteins into the nucleus.

Purified transferrin can be efficiently conjugated to some anticancer drugs through covalent linkers that are appropriately released inside the cells (Beyer U et al. 1998, J Med Chem 41(15):2701-2708). In case of transferrin, only lysine groups on the protein surface are ready available for covalent attachment.

Haemoglobin has been considered in the past as a possible drug carrier, due to its versatility in chemical conjugation with drugs, its abundance and relative stability in the blood (Somatogen, 1993, WO1993008842 A1). Nevertheless, the lack of receptor targeting properties did not foster biomedical applications other than blood substitutes or antisickling agent. As a matter of fact, Hb can only be recognized by CD163 (haptoglobin/haemoglobin receptor) epitopes on the leukocytes, especially monocyte-macrophage origin. The CD45$^+$ leukocyte, in particular macrophage based protein delivery, described in this application moved haemoglobin center stage as a target specific drug carrier. Haemoglobin can be readily covalently linked to appropriate drug conjugates, host hydrophobic drug molecules within the heme binding pocket or even transport small cytotoxic molecules linked to the heme iron. Hb can be easily modified by selective attachment of the appropriate drug conjugate to the beta93 cysteine residue, the only titratable cystein on the protein surface. Maleimido functionalized drugs, such as the tubuline inhibitor MonomethylAuristatin (MMAE) or the DNA crosslinking drug Pyrrolobenzodiazepine dimer (PBD) are most notable examples of extremely potent cytotoxics that can be readily and specifically attached to the relevant cys beta93 residue.

Alternatively, lysine residues on the Hb surface (at least 10 titratable lysine residues per Hb tetramer) may be easily amenable to drug conjugation through cleavable succinimide linkers. Haemoglobin also offers a unique capability of releasing non covalently bound heme group at acidic pH values. Apo-haemoglobin thus obtained is capable of hosting several hydrophobic molecules within the empty heme pocket, as shown in the case of paclitaxel (Meng Z et al. 2015 J Pharm Sci 104(3):1045-55).

Whatever the conjugationladsorption/binding method, haemoglobin (Hb), transferrin (Tf) and ferritins were shown by the present inventions to be privileged drug carriers, once loaded into appropriate cell systems with tumour targeting properties, e.g. activated macrophages. The easy, fast, cheap and safe purification procedure of these protein also provide a tremendous added value.

Based on sequences of mammalian H-type ferritins, L-type ferritins, haemoglobin alpha chains, haemoglobin beta chains and transferrins a consensus sequence was determined for each of these proteins. These are shown in FIG. 1 in SEQ ID NO: 2, 7, 9, 14, 16, 20, and 25, respectively). On this basis but also on the basis of deletion and structural analysis disclosed in the prior art a minimal fragment was determined for H-type ferritins, L-type ferritins, haemoglobin alpha chains, and haemoglobin beta chains sufficient for uptake by CD45$^+$ leukocytes. These are shown in SEQ ID NO: 1, 3, 5 (H-type ferritin); 8, 10 12 (L-type ferritin), 15 and 17 (haemoglobin alpha chain) and 19 and 21 (haemoglobin beta chain. Transferrin comprises a N-terminally located domain and a C-terminally located domain that are necessary for binding iron and uptake by CD45$^+$ leukocytes, if comprised in one polypeptide and positioned between 100 to 450 amino acids apart, preferably between 150 to 400, more preferably between 200 to 350 amino acids and more preferably 250 to 320 amino acids apart. The N-terminal domain comprises amino acids 1 to 82 of full length consensus transferrin (SEQ ID NO: 25) or full length human transferrin (SEQ ID NO: 28). The C-terminal domain comprises amino acids 396 to 510 of full length consensus transferrin (SEQ ID NO: 25) or full length human transferrin (SEQ ID NO: 28). In each case an X is indicated in the consensus sequence it independently stands for any amino acid and characterizes an amino acid not or only poorly conserved among mammalian H-type ferritins, which can be mutated without or little detriment to the iron binding properties of the respective iron binding protein. It is preferred that X in each case takes on the meaning of the amino acid of the respective human iron binding protein aligning with X. This information can be taken, e.g. from FIG. 1, which shows alignments of the consensus sequences with human an in some instances mouse proteins.

Preferred H-type ferritins comprise or consist of the amino acid sequence indicated in SEQ ID NO: 1 and variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a H-type ferritin consisting of the amino acid sequence according to SEQ ID NO: 1 to be taken up by CD45$^+$ leukocytes, preferably M2 leukocytes. Within SEQ ID NO: 1 X at position 5 may be present or absent, if present it means any amino acid, preferably Ile, X at position 6 means any amino acid, preferably Asn, X at position 14 means any amino acid, preferably Tyr, X at position 24 means any amino acid, preferably Tyr or Cys, X at position 66 means any amino acid, preferably Phe, X at position 68 means any amino acid, preferably Gln, X at position 75 means any amino acid, preferably Arg or Cys, X at position 90 means any amino acid, preferably His, X at position 94 means any amino acid, preferably Ser or Asn, X at position 120 may be present or absent, if present it means any amino acid, preferably His or Tyr, more preferably His, X at position 123 means any amino acid, preferably Asn or Ser, more preferably Asn, X at position 128 means any amino acid, preferably Ala or Ser, more preferably Ala.

In a preferred embodiment the H-type ferritin comprises or consists of murine ferritin according to SEQ ID NO: 3. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a H-type ferritin consisting of the amino acid sequence according to SEQ ID NO: 3 to be taken up by CD45$^+$ leukocytes, preferably M2 macrophages.

In a preferred embodiment the H-type ferritin comprises or consists of human ferritin according to SEQ ID NO: 5. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a H-type ferritin consisting of the amino acid sequence according to SEQ ID NO: 5 to be taken up by CD45$^+$ leukocytes, preferably M2 macrophages.

In a preferred embodiment the H-type ferritin comprises or consists of a mammalian consensus sequence derived from aligning full length H-type ferritins according to SEQ ID NO: 2 or 7, with 2 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a H-type ferritin consisting of the amino acid sequence according to SEQ ID NO: 2 or 7, with 2 being preferred to be taken up by CD45$^+$ leukocytes, preferably M2 macrophages. In SEQ ID NO: 2 X at position 6 can be any naturally occurring amino acid, preferably Pro, X at position 14 can be any naturally occurring amino acid, preferably His, X at position 16 can be any naturally occurring amino acid, preferably Asp, X at position 21 may be present or absent, if present it means any amino acid, preferably Ile, X at position 22 means any amino acid, preferably Asn, X at position 30 can be any naturally occurring amino acid, preferably Tyr, X at position 40 can be any naturally occurring amino acid, preferably Tyr or Cys, more preferably Tyr, X at position 82 can be any naturally occurring amino acid, preferably Phe, X at position 84 can be any naturally occurring amino acid, preferably Gln, X at position 91 can be any naturally occurring amino acid, preferably Arg or Cys, more preferably Cys, X at position 106 can be any naturally occurring amino acid, preferably His, X at position 110 can be any naturally occurring amino acid, preferably Asn or Ser, more preferably Asn, X at position 137 can be any naturally occurring amino acid, preferably His or Tyr, more preferably His, X at position 140 can be any naturally occurring amino acid, preferably Asn or Ser, more preferably Asn, X at position 145 can be any naturally occurring amino acid, preferably Ala or Ser, more preferably Ala, X at position 164 can be any naturally occurring amino acid, preferably Ala or Ser, more preferably Ser, X at position 166 can be any naturally occurring amino acid, preferably Met or Leu, preferably Leu, X at position 178 can be any naturally occurring amino acid, preferably Asp or His, more preferably Asp, X at position 181 is absent or any naturally occurring amino acid, preferably Asn, X at position 182 is absent or any naturally occurring amino acid, preferably Glu, X at position 183 is absent or any naturally occurring amino acid, preferably Ser. In SEQ ID NO: 7 X at position 6 can be any naturally occurring amino acid, preferably Pro X at position 14 can be any naturally occurring amino acid, preferably His, X at position 16 can be any naturally occurring amino acid, preferably Asp, X at position 21 may be present or absent, if present it means any amino acid, preferably Ile, X at position 29 can be any naturally occurring amino acid, preferably Tyr, X at position 81 can be any naturally occurring amino acid, preferably Phe, X at position 83 can be any naturally occurring amino acid, preferably Gln, X at position 105 can be any naturally occurring amino acid, preferably His, X at position 144 can be any naturally occurring amino acid, preferably Ala or Ser, more preferably Ala, X at position 180 is absent or any naturally occurring amino acid, preferably Asn, X at position 181 is absent or any naturally occurring amino acid, preferably Glu, X at position 182 is absent or any naturally occurring amino acid, preferably Ser.

In a preferred embodiment the H-type ferritin comprises or consists of murine full length ferritin according to SEQ ID NO: 4 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a murine H-type ferritin consisting of the amino acid sequence according to SEQ ID NO: 4 to be taken up by CD45$^+$ leukocytes, preferably M2 macrophages.

In a preferred embodiment the H-type ferritin comprises or consists of human full length ferritin according to SEQ ID NO: 6 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a human H-type ferritin consisting of the amino acid sequence according to SEQ ID NO: 6 to be taken up by CD45$^+$ leukocytes, preferably M2 macrophages.

Preferred L-type ferritins comprise or consist of the amino acid sequence indicated in SEQ ID NO: 8 and variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a L-type ferritin consisting of the amino acid sequence according to SEQ ID NO: 8 to be taken up by CD45$^+$ leukocytes, preferably M2 leukocytes. In SEQ ID NO: 8 X at position at position 5 can be any naturally occurring amino acid, preferably Asp or Glu, more preferably Asp, X at position 12 can be any naturally occurring amino acid, preferably Arg or Ser, more preferably Ser, X at position 17 can be any naturally occurring amino acid, preferably Ser or Arg, more preferably Ser, X at position 19 can be any naturally occurring amino acid, preferably Arg or Gln, more preferably Gln, X at position 29 can be any naturally occurring amino acid, preferably Phe, X at position 30 can be any naturally occurring amino acid, preferably Tyr or Phe, more preferably Tyr, X at position 42 can be any naturally occurring amino acid, preferably Ser or Gly, more preferably Ser, X at position 56 can be any naturally occurring amino acid, preferably Ala or Tyr, more preferably Tyr, X at position 61 can be any naturally occurring amino acid, preferably Glu or Lys, more preferably Lys, X at position 62 can be any naturally occurring amino acid, preferably Met or Phe, more preferably Met, X at position 65 can be any naturally occurring amino acid, preferably Asp or Gln, more preferably Gln, X at position 75 can be any naturally occurring amino acid, preferably Ile or Val, more preferably Ile, X at position 76 can be any naturally occurring amino acid, preferably Lys or Gln, more preferably Lys, X at position 79 can be any naturally occurring amino acid, preferably Ala or Ser, more preferably Ala, X at position 80 can be any naturally occurring amino acid, preferably Glu or Gln, more preferably Gln, X at position 87 can be any naturally occurring amino acid, preferably Pro or Gln, more preferably Pro, X at position 88 can be any naturally occurring amino acid, preferably Glu or Asp, more preferably Asp, X at position 91 can be any naturally occurring amino acid, preferably Glu or Lys, more preferably Lys, X at position 94 can be any naturally occurring amino acid, preferably Met or Leu, more preferably Leu, X at position 96 can be any naturally occurring amino acid, preferably Met or Leu, more preferably Met, X at position 99 can be any naturally occurring amino acid, preferably Lys or Asn, preferably Lys, X at position 115 can be any naturally occurring amino acid, preferably Thr or Ala, more preferably Thr, X at position 119 can be any naturally occurring amino acid, preferably Leu, X at position 125 can be any naturally occurring amino acid, preferably Ser or Thr, more preferably Thr, X at position 127 can be any naturally occurring amino acid, preferably Tyr or Phe, more preferably Phe, X at position 130 can be any naturally occurring amino acid, preferably Lys or Glu, more preferably Glu, X at position 140 can be any naturally occurring amino acid, preferably Asp or Asn, more preferably Asp, X at position 146 can be any naturally occurring amino acid, preferably Arg or His, more preferably His, and X at position 148 can be any naturally occurring amino acid, preferably Leu or Val, more preferably Leu.

In a preferred embodiment the L-type ferritin comprises or consists of murine L-type ferritin according to SEQ ID NO: 10. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a L-type ferritin consisting of the amino acid sequence according to SEQ ID NO: 10 to be taken up by CD45+ leukocytes, preferably M2 macrophages.

In a preferred embodiment the L-type ferritin comprises or consists of human ferritin according to SEQ ID NO: 12. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a L-type ferritin consisting of the amino acid sequence according to SEQ ID NO: 12 to be taken up by CD45+ leukocytes, preferably M2 macrophages.

In a preferred embodiment the L-type ferritin comprises or consists of a mammalian consensus sequence derived from aligning full length H-type ferritins according to SEQ ID NO: 9 or 14, with 9 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a L-type ferritin consisting of the amino acid sequence according to SEQ ID NO: 9 or 14, with 9 being preferred to be taken up by CD45+ leukocytes, preferably M2 macrophages. In SEQ ID NO: 9 X at position 12 X at position 12 can be any naturally occurring amino acid, preferably Asp or Glu, more preferably Asp, X at position 19 can be any naturally occurring amino acid, preferably Ser or Arg, more preferably Ser, X at position 24 can be any naturally occurring amino acid, preferably Ser or Arg, more preferably Ser, X at position 26 can be any naturally occurring amino acid, preferably Arg or Gln, more preferably Gln, X at position 36 can be any naturally occurring amino acid, preferably Phe, X at position 37 can be any naturally occurring amino acid, preferably Tyr or Phe, more preferably Tyr, X at position 47 can be any naturally occurring amino acid, preferably Ser or Gly, more preferably Ser, X at position 63 can be any naturally occurring amino acid, preferably Ala or Tyr, more preferably Tyr, X at position 68 can be any naturally occurring amino acid, preferably Glu or Lys, more preferably Lys, X at position 69 can be any naturally occurring amino acid, preferably Met or Phe, more preferably Met, X at position 72 can be any naturally occurring amino acid, preferably Asp or Gln, more preferably Gln, X at position 82 can be any naturally occurring amino acid, preferably Ile or Val, more preferably Ile, X at position 83 can be any naturally occurring amino acid, preferably Lys or Gln, more preferably Lys, X at position 86 can be any naturally occurring amino acid, preferably Ala or Ser, more preferably Ala, X at position 87 can be any naturally occurring amino acid, preferably Glu or Gln, more preferably Gln, X at position 94 can be any naturally occurring amino acid, preferably Pro or Gln, more preferably Pro, X at position 95 can be any naturally occurring amino acid, preferably Glu or Asp, more preferably Asp, X at position 98 can be any naturally occurring amino acid, preferably Glu or Lys, more preferably Lys, X at position 101 can be any naturally occurring amino acid, preferably Met or Leu, more preferably Leu, X at position 103 can be any naturally occurring amino acid, preferably Met or Leu, more preferably Met, X at position 106 can be any naturally occurring amino acid, preferably Lys or Asn, preferably Lys, X can be any naturally occurring amino acid, X at position 126 can be any naturally occurring amino acid, preferably Leu, X at position 132 can be any naturally occurring amino acid, preferably Ser or Thr, more preferably Thr, X at position 134 can be any naturally occurring amino acid, preferably Tyr or Phe, more preferably Phe, X at position 137 can be any naturally occurring amino acid, preferably Lys or Glu, more preferably Glu, X at position 147 can be any naturally occurring amino acid, preferably Asp or Asn, more preferably Asp, X at position 153 can be any naturally occurring amino acid, preferably Arg or His, more preferably His, X at position 155 can be any naturally occurring amino acid, preferably Leu or Val, more preferably Leu, X at position 161 can be absent or any naturally occurring amino acid, preferably Ala, X at position 163 can be absent or any naturally occurring amino acid, preferably Thr, X at position 166 can be absent or any naturally occurring amino acid, preferably Pro, and X at position 168 can be any naturally occurring amino acid, preferably Gly or Ala, more preferably Ala. In SEQ ID NO: 14 X at position 36 can be any naturally occurring amino acid, preferably Phe, X at position 37 can be any naturally occurring amino acid, preferably Tyr or Phe, more preferably Tyr, X at position 94 can be any naturally occurring amino acid, preferably Pro or Gln, more preferably Pro, X at position 126 can be any naturally occurring amino acid, preferably Leu, X at position 137 can be any naturally occurring amino acid, preferably Lys or Glu, more preferably Glu, X at position 147 can be any naturally occurring amino acid, preferably Asp or Asn, more preferably Asp, X can be any naturally occurring amino acid, X at position 163 can be absent or any naturally occurring amino acid, preferably Thr, X at position 166 can be absent or any naturally occurring amino acid, preferably Pro, X at position 168 can be any naturally occurring amino acid, preferably Gly or Ala, more preferably Ala.

In a preferred embodiment the L-type ferritin comprises or consists of murine full length ferritin according to SEQ ID NO: 11 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a murine L-type ferritin consisting of the amino acid sequence according to SEQ ID NO: 11 to be taken up by $CD45^+$ leukocytes, preferably M2 macrophages.

In a preferred embodiment the L-type ferritin comprises or consists of human full length ferritin according to SEQ ID NO: 13 being preferred. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a human L-type ferritin consisting of the amino acid sequence according to SEQ ID NO: 13 to be taken up by $CD45^+$ leukocytes, preferably M2 macrophages.

In a preferred embodiment the alpha haemoglobin comprises or consists of a minimal mammalian consensus sequence derived from aligning full length alpha haemoglobins according to SEQ ID NO: 15 Preferred comprise or consist of the amino acid sequence indicated in SEQ ID NO: 15 and variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of an alpha haemoglobin consisting of the amino acid sequence according to SEQ ID NO: 15 to be taken up by $CD45^+$ leukocytes, preferably M1 macrophages.

In a preferred embodiment the alpha haemoglobin comprises or consists of a minimal human amino acid sequence derived of human alpha haemoglobin according to SEQ ID NO: 17. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of an alpha haemoglobin consisting of the amino acid sequence according to SEQ ID NO: 17 to be taken up by $CD45^+$ leukocytes, preferably M1 macrophages.

In a preferred embodiment the alpha haemoglobin comprises or consists of a mammalian consensus sequence derived from aligning full length alpha haemoglobins according to SEQ ID NO: 16. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of an alpha haemoglobins consisting of the amino acid sequence according to SEQ ID NO: 16 to be taken up by $CD45^+$ leukocytes, preferably M2 macrophages.

In a preferred embodiment the alpha haemoglobin comprises or consists of human full length alpha haemoglobin according to SEQ ID NO: 18. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a human full length alpha haemoglobin consisting of the amino acid sequence according to SEQ ID NO: 18 to be taken up by $CD45^+$ leukocytes, preferably M2 macrophages.

In a preferred embodiment the alpha haemoglobin comprises or consists of a minimal mammalian consensus sequence derived from aligning full length beta haemoglobins according to SEQ ID NO: 19 and variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a beta haemoglobin consisting of the amino acid sequence according to SEQ ID NO: 19 to be taken up by $CD45^+$ leukocytes, preferably M1 macrophages.

In a preferred embodiment the alpha haemoglobin comprises or consists of a minimal human amino acid sequence derived of human beta haemoglobin according to SEQ ID NO: 21. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a beta haemoglobin consisting of the amino acid sequence according to SEQ ID NO: 21 to be taken up by $CD45^+$ leukocytes, preferably M1 macrophages.

In a preferred embodiment the beta haemoglobin comprises or consists of a mammalian consensus sequence derived from aligning full length beta haemoglobins according to SEQ ID NO: 20. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of an beta haemoglobins consisting of the amino acid sequence according to SEQ ID NO: 20 to be taken up by $CD45^+$ leukocytes, preferably M2 macrophages.

In a preferred embodiment the beta haemoglobin comprises or consists of human full length beta haemoglobin according to SEQ ID NO: 22. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a human full length beta haemoglobin consisting of the amino acid sequence according to SEQ ID NO: 22 to be taken up by CD45+ leukocytes, preferably M2 macrophages.

In a preferred embodiment the transferrin comprises or consists of a mammalian consensus sequence derived from aligning full length alpha haemoglobins according to SEQ ID NO: 25. Thus, particularly, preferred transferrins comprise or consist of the amino acid sequence indicated in SEQ ID NO: 25 and of variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a transferrin consisting of the amino acid sequence according to SEQ ID NO: 25 to be taken up by CD45+ leukocytes preferably M1 macrophages.

In a preferred embodiment the transferrin comprises or consists of human transferrin according to SEQ ID NO: 28. Accordingly, preferred structural variants have at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a transferrin consisting of the amino acid sequence according to SEQ ID NO: 28 to be taken up by CD45+ leukocytes, preferably M1 macrophages.

The iron binding properties of transferrins are dependent on a N-terminally and C-terminally located domain. Thus, in a preferred embodiment the transferrin used in the present invention comprises at least the N-terminal domain according to SEQ ID NO: 23 and the C-terminal domain according to SEQ ID NO: 24. Preferred transferrin comprise proteins that comprise the amino acid sequence indicated in SEQ ID NO: 23 and 24 as well as variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a transferrin consisting of the amino acid sequence according to SEQ ID NO: 23 and 24 to be taken up by CD45+ leukocytes, preferably M1 macrophages. SEQ ID NO: 23 or 24 indicates a consensus sequence of mammalian transferrins.

Thus, in a preferred embodiment the transferrin used in the present invention comprises at least the N-terminal domain according to SEQ ID NO: 26 and the C-terminal domain according to SEQ ID NO: 27. Preferred transferrin comprise proteins that comprise the amino acid sequence indicated in SEQ ID NO: 26 and 27 as well as variants thereof having at least 70% amino acid identity, more preferably at least 75% amino acid identity, more preferably at least 80% amino acid identity, more preferably at least 85% amino acid identity, more preferably at least 90% amino acid identity, more preferably at least 95% amino acid identity and in each case at least 70% of the ability of a transferrin consisting of the amino acid sequence according to SEQ ID NO: 26 and 27, respectively, to be taken up by CD45+ leukocytes, preferably M1 macrophages.

Preferred ferritins, also comprise proteins that, irrespective of the given amino acid sequence, conform to the 24-mer subunit assembly of a four helix bundle protein module, falling within given sequence alignments of distantly related proteins as defined by 3D structure based alignments.

It is a surprising observation of the present inventors that lymphocytes and M2 macrophages are better in uptake of complexes comprising one or more ferritin and one or more active ingredient, that M1 macrophages are better in uptake of complexes comprising one or more haemoglobin and one or more active ingredient and that macrophages are better in uptake of complexes comprising one or more transferrin and one or more active ingredient. Accordingly, based on the tissue and cellular tropism of CD45+ leukocytes: monocytes, M1 and M2 macrophages, granulocytes and lymphocytes, described above complexes comprising one or more ferritin and one or more active ingredient are used to load M2 macrophages, lymphocytes or monocytes if the tropism of M2 macrophages, lymphocytes or monocytes is desired and complexes comprising one or more haemoglobin and one or more active ingredient are used to load M1 macrophages, if the tropism of M1 macrophages is desired.

In a preferred embodiment of the targeted delivery system of the present invention the active ingredient is selected from the group consisting of a protein, a nucleic acid, a chemical non-protein non-nucleic acid compound with a molecular weight of less than 1.5 kD, more preferably less than 1 kD, preferably an anticancer drug, in particular a cytostatic drug, cytotoxic drug and prodrugs thereof; an anti arteriosclerotic drug; and anti-inflammatory drug; and photosensitizing compound; a virus, in particular oncolytic virus; and a α or β radiation emitting radioisotope, which also emit a cell damaging amount of γ radiation, preferably selected from the group consisting of lutetium-177, ytterbium-90, iodine-131, samarium-153, phosphorus-32, caesium-131, palladium-103, radium-233, iodine-125, and boron-10 or a cell damaging amount of a radiation, preferably selected from the group consisting of actinium-225, bismuth-213, lead-212, and polonium-212.

Preferred anticancer drugs are selected from an apoptosis/autophagy or necrosis-inducing drug. An apoptosis/autophagy or necrosis-inducing drug can be any drug that is able to induce apoptosis/autophagy or necrosis effectively even in cells having an abnormality in cell proliferation. These drugs are preferably used in complexes with one or more ferritins.

Preferred anticancer drugs are selected from the group consisting of an apoptosis-inducing drug, an alkylating substance, anti-metabolites, antibiotics, epothilones, nuclear receptor agonists and antagonists, an anti-androgene, an anti-estrogen, a platinum compound, a hormone, a antihormone, an interferon, an inhibitor of cell cycle-dependent protein kinases (CDKs), an inhibitor of cyclooxygenases and/or lipoxygenases, a biogeneic fatty acid, a biogenic fatty acid derivative, including prostanoids and leukotrienes, an inhibitor of protein kinases, an inhibitor of protein phosphatases, an inhibitor of lipid kinases, a platinum coordination complex, an ethyleneimine, a methylmelamine, a triazine, a *vinca* alkaloid, a pyrimidine analog, a purine analog, an alkylsulfonate, a folic acid analog, an anthracendione, a substituted urea, and a methylhydrazin derivative, an enediyne antibiotic, a tubulin polymerization inhibitor such as a maytansinoid or an auristatine derivate, immune checkpoint inhibitor, and an inhibitor of tumour-specific protein or marker, preferably a Rho-GDP-dissociation inhibitor, more preferably Grp94.

Other preferred anticancer drugs are selected from the group consisting of acediasulfone, aclarubicine, ambazone, aminoglutethimide, L-asparaginase, azathioprine, banoxantrone, bendamustine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethylstilbestrole, docetaxel, doxorubicin, enediynes, epirubicin, epothilone B, epothilone D, estramucin phosphate, estrogen, ethinylestradiole, etoposide, flavopiridol, floxuridine, fludarabine, fluorouracil, fluoxymesterone, flutamide fosfestrol, furazolidone, gemcitabine, gonadotropin releasing hormone analog, hexamethylmelamine, hydroxycarbamide, hydroxymethylnitrofurantoin, hydroxyprogesteronecaproat, hydroxyurea, idarubicin, idoxuridine, ifosfamide, interferon α, irinotecan, leuprolide, lomustine, lurtotecan, mafenide sulfate olamide, mechlorethamine, medroxyprogesterone acetate, megastrolacetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, scriflavinium chloride, semustine streptozocine, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxazole, co-trimoxazole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosteronpropionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin, preferably selected from the group consisting of auristatin, banoxantrone, bendamustine, chlorambucil, chaliceamycin, cyclophosphamide dynemycin A, maytansine, melphalan, mertansine, and neocazinostatin, most preferably banoxantrone, bendamustine, chlorambucil, cyclophosphamide, pyrrolobenzodiazepine and melphalan.

It is particularly preferred that the anticancer drug is a proliferation inhibiting protein, preferably a cell cycle inhibitor or an antibody or antibody mimetic that specifically binds to a target on or within a cell in the targeted tissue that modulates the disease status of the cell, preferably a proliferation promoting protein, or a nucleic acid, preferably encoding a proliferation inhibiting protein or an antibody or antibody mimetic that specifically binds to a target on or within a cell in the targeted tissue that modulates the disease status of the cell, preferably a proliferation promoting protein or a siRNA or DNAzyme.

Preferred examples of antibodies to be used in the context of the present invention are single chain antibodies, antibody fragments, nanobodies, light or heavy chains, variable light or variable heavy chains, or diabodies. Preferred antibody fragments comprise a fragment antigen binding (Fab) fragment, a Fab' fragment, a F(ab')2 fragment, a heavy chain antibody, a single-domain antibody (sdAb), a single-chain fragment variable (scFv), a fragment variable (Fv), a VH domain, a VL domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, and a fusion protein thereof.

If the active ingredient is a nucleic acid it is preferred that it is a miRNA, siRNA, DNAzyme or a nucleic acid encoding a pharmaceutically active protein, e.g. an antibody, an antibody mimetic, a cytokine, a prodrug-converting enzyme or the like.

As has been outlined above, the targeted delivery system of the present invention has particular suitability to deliver active ingredients to hypoxic areas. The use of active ingredients which are activated under hypoxic conditions adds a further specificity to the targeting and/or further reduces adverse effects of the active ingredients. Thus, in particularly preferred embodiments the active ingredient is a hypoxia-activated prodrug. The backbone of all the hypoxia-activated prodrugs is the presence of one of five different chemical moieties (nitro groups, quinines, aromatic and aliphatic N-oxides and transition metals) that are enzymatically reduced under hypoxic conditions in tissue. Hypoxia-activated prodrugs are any prodrug that is less active or inactive, relative to the corresponding drug, and comprises the drug and one or more bioreducible groups. Such hypoxia-activated prodrugs include all prodrugs activated by a variety of reducing agents and reducing enzymes, including without limitation single electron transferring enzymes (such as cytochrome P450 reductases) and two electron transferring (or hydride transferring) enzymes. According to preferred embodiment of the invention hypoxia-activated prodrug is TH-302. Methods of synthesizing TH-302 are described in PCT application WO 07/002931 and WO 08/083101. Preferably examples of such prodrugs are selected from the class I group consisting of: benzotriazine N-oxides, apaziquone (E09), tirapazamine (TPN) and SN30000; or class II group consisting of: nitro compounds PR-104A, TH-302, TH-4000, and AQ4N.

In a preferred embodiment of the isolated targeted delivery system of the present invention the bond(s) between the iron binding protein(s) and the active ingredient comprised in the complex are covalent and/or non-covalent; and/or the active ingredient comprised in the complex is entrapped/encapsulated by the iron binding protein, preferably ferritin or multimers thereof. In one embodiment the covalent and/or non-covalent coupling is indirect through a linker or spacer. If the formation of covalent bonds is desired, relevant thiol, amino or carboxyl groups of the iron binding proteins are used to covalently couple active ingredients directly or indirectly to the one or more iron binding protein. It is also envisioned that different active ingredients are comprised in the complex. For example, one type of active ingredient may be bound to an iron binding protein (non-covalently bound), while another type is encapsulated. This approach utilizes different release rates of the active ingredients from the iron binding protein once delivered to the targeted tissue and/or cells. For example, drug derivatives acting as active ingredient can be covalently attached to ferritin molecule either on the surface of the 24-mer or within the internal cavity by exploiting the reactivity of relevant thiol, amino or carboxyl groups. The types of such useful reactions are well known in the art and can be adopted by the person skilled in the art to the concrete active ingredient without any additional work. Examples of such reactions are described in Behrens C R, Liu B. Methods for site-specific drug conjugation to antibodies. MAbs. 2014 January-February; 6(1):46-53.

In a further aspect the present invention relates to a method of preparation of the isolated targeted delivery system of the present invention comprising the steps of a) providing purified iron binding protein as defined above;
b) covalently or non-covalently linking an active ingredient to and/or encapsulating an active ingredient in an iron binding protein;
c) providing a CD45+ leukocyte cell as defined above; and
d) incubating the CD45+ leukocyte cell in the presence of the complex of the iron binding protein and the active ingredient produced in step b) until the CD45+ leukocyte cell is at least partially, preferably fully loaded with the complex of the iron binding protein and the active ingredient produced in step b).

The formation of the adduct between the protein and the drug moiety may be a non-covalent drug molecule binding to the target protein and can be described as follows: In the case of ferritin, drugs can be typically encapsulated within the internal cavity (physical confinement) by exploiting the association dissociation properties of the ferritin macromolecule itself. Drug molecules are held in place by non-covalent interactions with aminoacid residues within the cavity internal surface. Haemoglobin macromolecules also offer the possibility of non-covalent binding of selected drug molecules that may be hosted within the heme binding pocket of haemoglobin itself. The heme can be displaced by the pocket and be replaced by drugs with appropriate hydrophobicity profile. In a further aspect, all proteins considered in the present invention may be covalently attached to drug molecules modified by specific active linker moieties reactive towards thiol or amino groups of the protein itself. As such, ferritins or haemoglobin may be linked to cysteine thiol reactive drugs bearing a peptide based cleavable linker (e.g. cathepsin sensitive valine-citrulline sequence and para-aminobenzylcarbamate spacer). As a notable example, the antimitotic agent monomethyl auristatin E (MMAE) has been used. The peptide-based linker binds the protein to the cytotoxic compound in a stable manner so the drug is not easily released from the protein under physiologic conditions and help prevent toxicity to healthy cells and ensure dosage efficiency. The protein drug adduct thus generated is capable of attaching to the selected receptor types, i.e. CD163 for haemoglobin and TfR for ferritin or transferrin, respectively. Once bound the protein drug adduct is internalised by endocytosis and thus selectively taken up by targeted cells. The vesicle containing the drug is fused with lysosomes and lysosomal cysteine proteases, particularly cathepsin B start to break down valine-citrulline linker and MMAE is no longer bound to the antibody and is released directly into the tumour environment.

Alternatively, DM1-SMCC is and efficient mertansine derivative bearing a linker that specifically bind to lysine residues generating a covalent complex with ferritin, haemoglobin or transferrin in a reaction that has been successfully described for antibodies. In particular, haemoglobin, ferritin or transferrin can be reacted with DM1-SMCC thus providing a covalent protein-drug adduct that can be cleaved inside cells and releases the active drug in a time-dependent manner. The suppression of microtubule dynamics by DM1 induces mitotic arrest and cell death.

The term "full load" is used in the context of the present invention to refer to the maximum amount of iron binding protein, preferably ferritin, complexed with an active ingredient that can be taken up by the CD45+ leukocyte cell, preferably macrophage more preferably activated macrophage.

In a third aspect the present invention relates to the isolated targeted delivery system of the present invention for use as a medicament.

In a fourth aspect the present invention relates to a pharmaceutical composition comprising the isolated targeted delivery system of the present invention and a pharmaceutically acceptable carrier and/or suitable excipient(s). Since the isolated targeted delivery system comprises living cells, it is preferred that carriers and excipients are chosen in such to keep the cells alive.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-10, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

In a fifth aspect the present invention relates to the isolated targeted delivery system of the present invention for use in preventing/treating tumours, preferably a solid tumour, preferably breast cancer, pancreatic cancer, bladder cancer, lung cancer, colon cancer, or a tumour having hypoxic areas, inflammatory disease or ischemic areas in skin wounds, other wounds, or after organ infarctus (heart) or ischemic retina.

The term "treatment" as used herein includes all types of preventive and/or therapeutic interventions medically allowed for the purpose of cure, temporary remission, prevention, etc. for different purposes including delaying or stopping the progress of a disease, making a lesion regress or disappear, preventing onset, or inhibiting recurrence.

The targeted delivery system according to the present invention enables tumour delivery of the active ingredients, which normally would not be able to reach the tumour (for example, due to solubility problems). It also enables the delivery of active ingredients to the hypoxic tumours or to the hypoxic areas of the tumour. This system also provides for delivery of a active ingredient to any area within an organism subjected to hypoxic conditions, for example during ischaemic incidents, or undergoing an inflammatory process.

As mentioned above the present invention provides also the method for targeted drug delivery into the tumour mass. This method comprises preparation of CD45$^+$ leukocytes, preferably activated macrophages which enables highly efficient iron-binding protein (ferritin, haemoglobin and/or transferring) uptake by the macrophages, wherein said ferritin, haemoglobin and/or transferrin carry an active ingredient (for example a drug/prodrug), tumour targeting and iron-binding protein transfer to the cancer cell, where the active ingredient is released.

The present invention exploits CD45$^+$ leukocytes, preferably activated macrophages loaded with iron-binding proteins linked with a drug/prodrug as a delivery system to target the tumour. Unsatisfactory response of the tumours to chemotherapy or difficulties in their detection using imaging methods are mainly related to an altered penetration of the anticancer drugs to the hypoxic areas due to poor vasculature. However, these avascular regions attract CD45$^+$ leukocytes, preferably activated macrophages to migrate even in areas far away from blood vessels. Therefore, they constitute a delivery system of particles to the tumour mass. A promising example of such particles is iron-binding protein. However, when used as single agents they do not reach hypoxic regions, similarly to other compounds and accumulate in other organs.

The present inventors linked anticancer drugs, hypoxia activated prodrugs (for treatment purposes) or isotopes to haemoglobin or transferrin using chemical methods and loaded it into CD45$^+$ leukocytes (monocytes, macrophages, lymphocytes and/or granulocytes), preferably activated macrophages treating cells with iron-binding protein solution as it is described in examples. The inventors observed that upon administration to the animal, loaded CD45$^+$ leukocytes, preferably activated macrophages migrate to the tumour hypoxic sites and release iron-binding protein with encapsulated active ingredients into the cancer cells. This method allows precise administration of the active ingredients to the tumour site (especially to the hypoxic regions), avoiding their accumulation in other organs.

BRIEF DESCRIPTION OF DRAWINGS

FIG. 1: Panel (A) shows a minimal active fragment of a consensus amino acid sequence among mammalian ferritin H chains and two full length consensus sequences based on several mammalian ferritin H chains (see SEQ ID NO: 1, 2 and 7, respectively) as well as a minimal and full length amino acid sequence of mouse (SEQ ID NO: 3 and 4) and human (SEQ ID NO: 5 and 6) ferritin H chain. Panel (B) shows a minimal active fragment of a consensus amino acid sequence among mammalian ferritin L chains and two full length consensus sequences based on several mammalian ferritin L chains (see SEQ ID NO: 8, 9 and 14, respectively) as well as a minimal and full length amino acid sequence of mouse (SEQ ID NO: 10 and 11) and human (SEQ ID NO: 12 and 13) ferritin L chain. Panel (C) shows a minimal active fragment of a consensus amino acid sequence among mammalian haemoglobin alpha chains and one full length consensus sequences based on several mammalian haemoglobin alpha chain (see SEQ ID NO: 15 and 16, respectively) as well as a minimal and full length amino acid sequence of human (SEQ ID NO: 17 and 18) haemoglobin alpha chain. Panel (D) shows a minimal active fragment of a consensus amino acid sequence among mammalian haemoglobin beta chains and a full length consensus sequences based on several mammalian haemoglobin beta chain (see SEQ ID NO: 19 and 20, respectively) as well as a minimal and full length amino acid sequence of human (SEQ ID NO: 21 and 22) haemoglobin beta chain. Panel (E) shows a N- and C-terminal minimal active fragment of a consensus amino acid sequence among mammalian transferrins (SEQ ID NO: 23 and 24) and a full length consensus sequences based on several mammalian transferrins (SEQ ID NO: 25) as well as a N- and C-terminal minimal active fragment of a human transferrin (SEQ ID NO: 26 and 27) and full length amino acid sequence of human transferrin (SEQ ID NO: 28). In the consensus sequences X indicates a position that is variable and stands for any natural amino acid. Preferably, in each case X in dependently of other X stands for the amino acid present in the human protein.

FIG. 8: Shows ferritin, haemoglobin and transferrin uptake by macrophages, ferritin and haemoglobin uptake by monocytes and ferritin uptake by lymphocytes and granulocytes.

FIG. 9: Shows the stability of the ferritin storage by macrophages.

FIG. 12: Shows the transfer of ferritin encapsulated with hypoxia activated prodrug from macrophage to cancer cells.

EXAMPLE SECTION

Example 1—Activation of Macrophages

Figure 2:
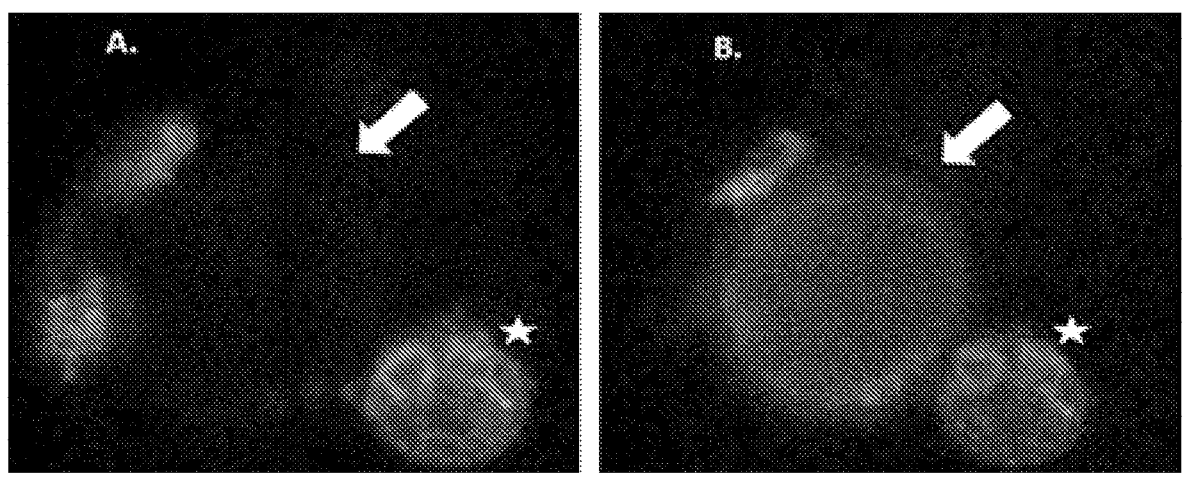
FIG. 2: Shows macrophage inside the mouse tumour mass (TRITC stained before injection, loaded with FITC-decorated ferritin).

Macrophages for use according to the present invention were obtained, differentiated and activated as follows. In order to activate macrophages, they are obtained firstly from bone marrow precursors (for example see paper: Weischenfeld and Porse, 2008, CSH Protoc, doi. 10.1101/pdb.prot.5080) or blood monocytes. Alternatively, they can be obtained from peritoneum. The methods of macrophage isolation, culture, differentiation and polarization/activation are well known for those skilled in the art. For example, they have been described in details by Murray et al. (Immunity, 2014, 41(1):14-20).

In this practical realization of the invention bone marrow derived macrophages were obtained from BALB/c or C57Bl/6 mouse, however canine blood-monocyte-derived macrophages or commercially available macrophage cell lines (monocyte-macrophage lineage mouse cells: RAW 264.7, J744, human: THP-1, U937, or canine DH82 cell line).

Shortly, such bone marrow derived macrophages are seeded in plastic Petri dish in 5 ml medium (3 ml cells per plate): DMEM:F12+ glutamine/glutamax+10% FBS+Penicillin/Streptomycin and 20% of L929 conditioned medium or M-CSF (50 ng/ml). In the next five days the medium is supplemented in growth factor and one of the activating compounds or their combinations as one cytokine cocktail.

Alternatively, macrophages have been cultured in "M1/M2 Macrophage Generation Medium" (Promocell) or equivalent commercially available or self-made medium containing all the necessary cytokines and interleukins to consider them as activated.

In order to obtain macrophages from blood monocytes, fresh blood (not older than 12 hours) is spin down using Histopaque system 1077 or equivalent and white blood cells (or alternatively, only white blood cells collected from the blood bank) in an appropriate amount of pre-warmed Monocyte Attachment Medium (or equivalent, e.g. DMEM/RPMI supplemented with M-CSF), e.g. 15 ml Medium per T-75 flask. A seeding density should be of 1-2 million/cm2 for mononuclear cells with a monocyte content of >25% and 1.5-3 million/cm$^2$ for a monocyte content of <25%. Then, cells are incubated for 1-1.5 hours at 5% $CO_2$ and 37° C. in the incubator without any further manipulation.

After cell attachment, they are washed at least twice, and then an appropriate amount of complete "M1- or M2-Macrophage Generation Medium DXF" is added to the cells (e.g. 20 ml per T-75 flask) and cells are incubated for 6 days at 37° C. and 5% $CO_2$ without medium change. In order to activate macrophages, the whole medium should be replaced with medium supplemented by activating compound.

Activating compounds used in this invention (for bone-marrow derived cells or to activate cells from monocyte-macrophage cell lines) are as follows: IL-4 (20 ng/ml), IFN-γ (at least 20 ng/ml), LPS (at least 10 ng/ml), IL-13 (at least 20 ng/ml), IL-10 (at least 20 ng/ml), dexamethason (at least 20 μg/ml), oxLDL (at least 20 ng/ml), TNF-α (20 ng/ml), TGF-β (20 ng/ml), cortisol (150-300 ng/ml) or their combinations as one cytokine cocktail. In order to obtain unactivated macrophages, the activating compound has not been added.

Reverse of the polarization/activation of macrophages (from classically activated to alternatively activated) can be reached for example by culture of macrophages in appropriate cytokines listed above for at least 48 hrs.

Example 2—Monocyte Isolation

In order to obtain monocytes in this practical realization of the invention bone marrow derived or spleen-derived monocytes were obtained from BALB/c or C57Bl/6 mouse, however canine blood monocyte or commercially available monocyte cell lines were used (monocyte-macrophage lineage mouse cells: RAW 264.7, J744, human: THP-1, U937, or canine DH82 cell line).

To obtain blood monocytes, fresh blood (not older than 12 hours) is spin down using Histopaque system 1077 or equivalent and white blood cells are seeded in an appropriate amount of pre-warmed Monocyte Attachment Medium (or equivalent, e.g. DMEM/RPMI supplemented with 20 ng/ml M-CSF), e.g. 15 ml Medium per T-75 flask. Alternatively, only white blood cells collected from the blood bank (buffy coat) may be used. A seeding density should be of 1-2 million/cm2 for mononuclear cells with a monocyte content of >25% and 1.5-3 million/cm2 for a monocyte content of <25%. Then, cells are incubated for 1-1.5 hours at 5% $CO_2$ and 37° C. in the incubator without any further manipulation. After cell attachment, they are washed at least twice, and adherent cells are considered as monocytes.

In order to obtain bone-marrow derived monocytes, in this practical realization of the invention bone marrow derived macrophages were obtained from BALB/c or C57Bl/6 mouse. Shortly, such bone marrow derived precursors are seeded in plastic Petri dish in 5 ml medium (3 ml cells per plate): DMEM:F12+ glutamine/glutamax+10% FBS+Penicillin/Streptomycin and 20% of L929 conditioned medium or 20 ng/ml M-CSF. Two days later 5 ml of standard medium is added. Then, after two days 0.5 ml/plate L929 conditioned medium is added. Adherent cells are considered as monocytes.

In order to obtain spleen derived monocytes, in this practical realization of the invention, the spleen has been mechanically dissociated to obtain single cell suspension and passed through the 70 μm cell strainer. Cells were centrifuged and supernatant was removed. After erythrocyte lysis the monocytes were isolated using magnetic bead purification e.g. EasySep Mouse Monocyte Enrichment Kit protocol and appropriate magnet.

To obtain better effects of their protein loads and migration before use they may be pre-treated with macrophage activation stimuli: IL-4 (20 ng/ml), IFN-γ (at least 20 ng/ml), LPS (at least 10 ng/ml), IL-13 (at least 20 ng/ml), IL-10 (at least 20 ng/ml), dexamethason (at least 20 μg/ml), oxLDL (at least 20 ng/ml), TNF-α (20 ng/ml), TGF-β (20 ng/ml), cortisol (150-300 ng/ml) or their combinations as one cytokine cocktail.

Example 3—Granulocyte Isolation

To obtain granulocyte cells from blood, 9 parts of blood were diluted with 1 part of ACD buffer (containing 0.17 M d-glucose, 0.10 M citric acid, 0.11 M trisodium citrate). Blood from this step was further diluted with PBS at the 1:1 ratio and centrifuged. After removing plasma and buffy coat, remaining cells were mixed with PBS to 80% of the original volume from the first step (ACD-blood) and then diluted with cold distilled water at the ratio of 4:12. Then, 6 parts of 2.7% of NaCl solution were added and centrifuged. After removal of supernatant cells were resuspended in RPMI-1640 medium. These cell were considered as granulocytes.

Example 4—Lymphocyte Isolation

In order to obtain spleen derived lymphocytes, in this practical realization of the invention, the spleen has been mechanically dissociated to obtain single cell suspension and passed through the 70 μm cell strainer. Cell were centrifuged and supernatant was removed. After erythrocyte lysis the lymphocytes were isolated using magnetic bead purification e.g. EasySep Mouse CD4$^+$ Enrichment Kit protocol and appropriate magnet.

Example 5—Preparation of Ferritin Complexes

In order to incorporate ferritins with the anticancer drug (e.g. classic drugs like cyclophosphamide, chlorambucil, melphalan, bendamustine, banoxantrone or hypoxia-activated prodrug like TH-302) ferritins have to be prepared before macrophage treatment.

Shortly, recombinant mouse proteins according to SEQ ID NO: 4 (FIG. 1) are obtained as follows. The expression vector pET-22b containing a synthetic gene encoding ferritin protein of SEQ ID NO: 4 was transformed into E. coli BL21 (DE3). E. coli culture was grown at 37° C. to OD600 0.6 in 1 L of Luria-Bertani broth (LB) added with ampicillin (100 mg/L). Protein expression was induced by addition of 1 mM isopropyl thio-b-D-galactoside (IPTG) and the culture was incubated overnight. Cells were harvested by centrifugation (15000 g for 15 min) and suspended in 20 mM Hepes (pH 7.5), 150 mM NaCl, 0.1 mg/mL DNase, 10 mM $MgCl_2$ and disrupted by sonication. The lysate was centrifuged at 15000 g for 30 min and the supernatant was treated 10 min at 50° C., centrifuged to remove denatured proteins and then at 70° C. for 10 min and centrifuged again. The supernatant was added with 30% $(NH_4)_2SO_4$ at 4° C. stirring for 1 h and centrifuged at 15000 g for 30 min. The supernatant was added with 70% $(NH_4)_2SO_4$ at 4° C. stirring for 1 h and centrifuged at 15000 g for 30 min. The pellet was resuspended in 20 mM Hepes (pH 7.5), 150 mM NaCl and dialysed overnight at 4° C. against the same buffer. The protein was loaded on a HILOAD 26/600 SUPERDEX 200 gel-filtration column (GE-Healthcare) and then sterile filtered and stored at 4° C. (FIG. 9) Protein concentration was determined spectrophotometrically at 280 nm using a molar extinction coefficient of 21000 $M^{-1}$ $m^{-1}$ and by Bradford assay measuring the absorbance at 595 nm.

Said ferritins include recombinant mammalian ferritin proteins H and/or L homopolymers.

Ferritins, obtained as previously described, are purified by standard methods in order to obtain an endotoxin free, pre-clinical grade product (see, for example: Ceci et al. 2011, Extremophiles 15(3):431-439; Vanucci et al. 2012, Int J Nanomed 7:1489-1509). Shortly, the ferritin conserved sterile in a storage solution containing 20 mM Hepes pH 7.5 is diluted to a final concentration of 4 uM in 24-mer in acidic solution (final pH<3.0) or, alternatively, at highly basic pH values (pH>9.5) (see for example Pontillo et al., 2016), thus allowing the dissociation of multimer. Drugs are dissolved at very high concentrations in the appropriate solvent and then a small volume is added to the ferritin solution with a 200 molar excess. PH is then brought to neutrality by addition of appropriate amounts of NaOH/HCl solutions in order to allow multimer reconstitution. Current experimental methods indicate that three/four washings using PBS (concentration steps) in 100 kDa cut off concentrators allows rapid and complete elimination both the co-solvents as well as non-encapsulated drugs and full recovery of drug loaded ferritin nanocages. The ferritin-drug complex thus obtained was then flash freezed in liquid nitrogen and lyophilised.

Depending on the choice of co-solvent and on the intrinsic chemical properties of the drug molecule, it can be estimated that up to 150-180 drug molecules can be entrapped/adsorbed within the 24-mer ferritin cage.

Drugs may also be covalently coupled to ferritin amino-acid side chains (lysines or cysteines) by appropriate choice of phenylhydrazone, succinimide or maleimide activated drugs. Accordingly, i) phenylhydrazone derivative may breaks and liberates the drug from the ferritin surface, ii) lysine bound derivatives may become active after full protein degradation into aminoacids or iii) cysteine bound derivative may be liberated within the cell through reductive hydrolysis of the maleimede thioether link.

Example 6—Preparation of Haemoglobin-Compound Complex

Human haemoglobin is prepared from fresh red cells as described in Rossi-Fanelli et al. (Archives of biochemistry and biophysics 77:478-492, 1958). Shortly, the heparinized blood, obtained from healthy donors, was centrifuged at 1600 rpm for 30 minutes (4° C.) to sediment the RBCs. Buffy coat was accurately removed by needle aspiration on the surface of the pellet. The plasma supernatant was discarded and the RBC pellet was washed three times by resuspending the RBCs in isotonic 0.9% saline solution and centrifuging at 1600 rpm for 30 minutes at 4° C. After the final saline wash and centrifugation step, the RBC pellet was resuspended in distilled water buffered at pH 7.2 with 5 mM potassium phosphate buffer (PB, pH=7.2) and allowed to lyse at 4° C. overnight under gentle stirring. Dialyzed RBC lysate was subsequently centrifuged at 13.000 rpm for 30 min at 4° C. and supernatant was directly loaded on an AKTA Explorer system equipped with an XK 26/40 column packed with Q-sepharose XL resin (GE Healthcare) at room temperature. Columns were equilibrated with buffer A (20 mM Tris-HCl, pH=8.2) at a flow rate of 12 mL/min and washed three times with the same buffer. A linear gradient elution was generated by changing from 100% buffer A to 75% buffer B (20 mM Tris-Cl, plus 0.2 M NaCl pH8.20) followed by a step gradient of 100% buffer B. Upon elution, a fraction collector was used to collect protein fractions. Protein thus obtained was analyzed by SDS page and stored frozen at −80° C.

Human Haemoglobin (SEQ ID NO: 18 or 22, see FIG. 1) can be readily covalently linked to appropriate drug conjugates, host hydrophobic drug molecules within the heme binding pocket or even transport small cytotoxic molecules linked to the heme iron. Hb can be easily modified by selective attachment of the appropriate drug conjugate to the cysteine residue in position 93 of the beta chains, the only titratable cystein on the protein surface. Maleimido functionalized drugs, such as the tubuline inhibitor MonomethylAuristatin (MMAE) or the succinimide functionalized mertansine analogue (DM1-SMCC) are most notable examples of extremely potent cytotoxics that can be readily and specifically attached to the relevant cys beta93 residue (for maleimido functionalized drugs) or to one or more lysine residues (succinimide functionalized drug), respectively. These drugs have been conveniently conjugated to human haemoglobin according to the following procedures:

The auristatin E analogue, maleimidocaproyl-valine-citrulline-p-aminobenzoyloxycarbonyl-monomethyl auristatin E (vcMMAE) was obtained from MedChem Express (Princeton, N.J.). The Haemoglobin vcMMAE adduct was prepared as follows. Human haemoglobin solution was adjusted to a concentration of 120 µM heme with reaction buffer (50 mM phosphate buffer pH 6.8, containing 0.1 mM EDTA) and conjugated with 10-fold molar excess of vcMMAE in the presence of 20% v/v acetonitrile solution at 4° C. overnight. Maleimide groups react efficiently and specifically with free (reduced) sulfhydryls at pH 6.5-7.5 to form stable thioether bonds. The excess vcMMAE was purified and buffer-exchanged with D-PBS using PM 100 ultrafiltration concentrator. The yield of conjugation was approximately 80% of the total cysteines. Formation of vcMMAE conjugate was confirmed by LC-MS analysis and by titration of residual free thiol group with p-chloromercuribenzoate. The concentrations of Hb-vcMMAE conjugates were determined by UV-vis spectroscopy analysis.

The mertansin analogue DM1 SMCC (Alb Technology Ltd, Hederson, Nev., USA), functionalized for lysine covalent attachment, was prepared as follows. Human haemoglobin solution was adjusted to a concentration of 400 µM heme with reaction buffer (0.1 mM phosphate buffer pH 7.4, containing 0.5 mM EDTA) and conjugated with 20-fold molar excess of DM1-SMCC in the presence of 10% v/v DMSO solution at 4° C. for 16 hours. The amine-reactive succinimidyl ester couples to amines thus yielding a covalent adduct with lysine groups on the surface of the protein. The excess DM1-SMCC was eliminated and buffer-exchanged with D-PBS using PM 100 ultrafiltration concentrator. The yield of conjugation was approximately 2.4 mertansine molecules per haemoglobin tetramer. Formation of DM1-SMCC conjugate was confirmed by LC-MS analysis. The concentrations of Hb-DM1-SMCC conjugates were determined by UV-vis spectroscopy analysis.

Example 7—Preparation of Transferrin-Compound Complex

The serum was obtained from healthy donor and excess iron was added in the presence of citrate ions as a chelator and bicarbonate, which is facilitates for iron binding to transferrin. The reaction mixture contained 6.5 mg sodium bicarbonate and 153.16 ferric citrate in pH=8, 4° C., 1 h per 100 mL of serum. Albumin was subsequently precipitated by Rivanol (4%) by adding the alcohol solution to the serum sample in a 3.5 V/V ratio at 4° C., and pH=9.4 for 2 h. Then, the solution was centrifuged at 3000 rpm for 20 min and finally filtered by filter on a 0.8 mm syringe filter. Excess Rivanol was subsequently removed by gel-filtration on a Sephadex G-25 column in ammonium sulfate 0.025 M. A first precipitation of by saturated ammonium sulfate 50% at pH=6.5 was subsequently carried out followed by centrifugation at 3000 rpm for 10 min (immunoglobulin removal). A second precipitation at 80% saturated ammonium sulfate was then carried out thus allowing recovery of transferrin the precipitate. Solid precipitate was then dissolved in buffer of 0.06 M Tris HCl buffer, pH=8, containing 1 M NaCl. The solution was dialyzed in the same buffer to allow full removal of ammonium sulfate. Protein solution was then concentrated with a centricon PM50 centrifugal concentrator up to 10-15 mg/ml (as estimated by Bradford method) and loaded on a Sephadex G-100 gel-filtration column (2.4×80 cm) equilibrated in 1M NaCl, flow rate of 15 ml/h. Transferrin thus obtained was estimated to be 88-90% pure by SDS page. Ion-exchange chromatography by anion exchanger DEAE Sephadex A-50 was then used as a final polishing step. The transferrin sample was loaded in the column equilibrated with 0.06 M Tris HCl at pH=8 and eluted by a linear concentration gradient with elution buffer, 0.3 M Tris HCl, pH=8. Protein purity was higher than 98% with a yield of about 150 mg per 100 mL of serum.

Human Holo-transferrin, (SEQ ID NO: 28, FIG. 1) similarly to haemoglobin can be readily covalently linked to appropriate drug conjugates, although there is only availability for lysine modifications, due to the absence of freely titratable cysteine groups. Thus the succinimide functionalized mertansine analogue (DM1-SMCC) has been used to covalently attach to one or more lysine residues (succinimide functionalized drug). The drug has been conveniently conjugated to transferrin according to the following procedure:

The mertansin analogue DM1 SMCC (Alb Technology Ltd, Hederson, Nev., USA), functionalized for lysine covalent attachment, was prepared as follows. Taansferrin solution was adjusted to a concentration of 100 µM heme with reaction buffer (0.1 mM phosphate buffer pH 7.4, no EDTA in this case due to possible iron chelation effects) and conjugated with 20-fold molar excess of DM1-SMCC in the presence of 8% v/v DMSO solution at 4° C. for 16 hours. The amine-reactive succinimidyl ester couples to amines thus yielding a covalent adduct with lysine groups on the surface of the protein. The excess DM1-SMCC was eliminated and buffer-exchanged with D-PBS using PM 100 ultrafiltration concentrator. The yield of conjugation was approximately 1.5 mertansine molecule per transferring dimer. Formation of DM1-SMCC conjugate was confirmed by LC-MS analysis. The concentrations of Transferrin-DM1-SMCC conjugates were determined by UV-vis spectroscopy analysis.

Example 8—Obtaining Ferritin Loaded Cells

Obtained cells are incubated in ferritin solution for a time and at the concentration sufficient to ensure proper ratio of ferritin/cell for their full load and also to ensure proper drug content to obtain therapeutic effect). The time and concentration may vary depending on the number of molecules encapsulated/adsorbed into the ferritin cage, status of cell activation, condition and number of their intended administration.

For example, to ensure proper load with ferritins, cells are incubated for 1-4 hrs in ferritin solution 0.2 mg/ml in standard culture conditions. The frame of ferritin concentration may vary at least between 0.01 and 4 mg/ml as well as incubation time (5 min-6 hrs or more). Adjusting time and concentration of ferritin load to cells, the influence of ferritin and treatment conditions on cell viability should be minded. Cells obtained as stated above very easily uptake ferritins in a relatively short time (in minutes; FIG. 8). Once they absorb ferritins, they do not release it to the culture medium (FIG. 9).

Nevertheless, the person skilled in the art is able to re-adjust the above conditions and optimize the protocol for the own purposes in the own laboratory.

Example 9—Obtaining Haemoglobin Loaded Cells

Obtained cells are incubated in haemoglobin solution for a time and at the concentration sufficient to ensure proper ratio of haemoglobin/cell for their full load and also to ensure proper drug content to obtain therapeutic effect). The time and concentration may vary depending on the number of molecules linked with the haemoglobin molecule, status of cell activation, condition and number of their intended administration.

For example, to ensure proper load with haemoglobins, cells are incubated for 1-4 hrs in haemoglobin solution 0.1 mg/ml in standard culture conditions. The frame of haemoglobin concentration may vary at least between 0.01 and 0.2 mg/ml as well as incubation time (5 min-4 hrs or more). Adjusting time and concentration of haemoglobin load to cells, the influence of ferritin and treatment conditions on cell viability should be minded. Cells obtained as stated above very easily uptake haemoglobins in a relatively short time (in minutes; FIG. 8).

Nevertheless, the person skilled in the art is able to re-adjust the above conditions and optimize the protocol for the own purposes in the own laboratory.

Example 10—Obtaining Transferrin Loaded Cells

Obtained cells are incubated in transferrin solution for a time and at the concentration sufficient to ensure proper ratio of transferrin/cell for their full load and also to ensure proper drug content to obtain therapeutic effect). The time and concentration may vary depending on the number of molecules linked with the transferrin molecule, status of cell activation, condition and number of their intended administration.

For example, to ensure proper load with transferrins, cells are incubated for 1-4 hrs in transferrin solution 0.1 mg/ml in standard culture conditions. The frame of transferrin concentration may vary at least between 0.01 and 0.2 mg/ml as well as incubation time (5 min-4 hrs or more). Adjusting time and concentration of transferrin load to cells, the influence of transferrin and treatment conditions on cell viability should be minded. Cells obtained as stated above very easily uptake transferrin in a relatively short time (in minutes; FIG. 8).

Nevertheless, the person skilled in the art is able to re-adjust the above conditions and optimize the protocol for the own purposes in the own laboratory.

Figure 4:
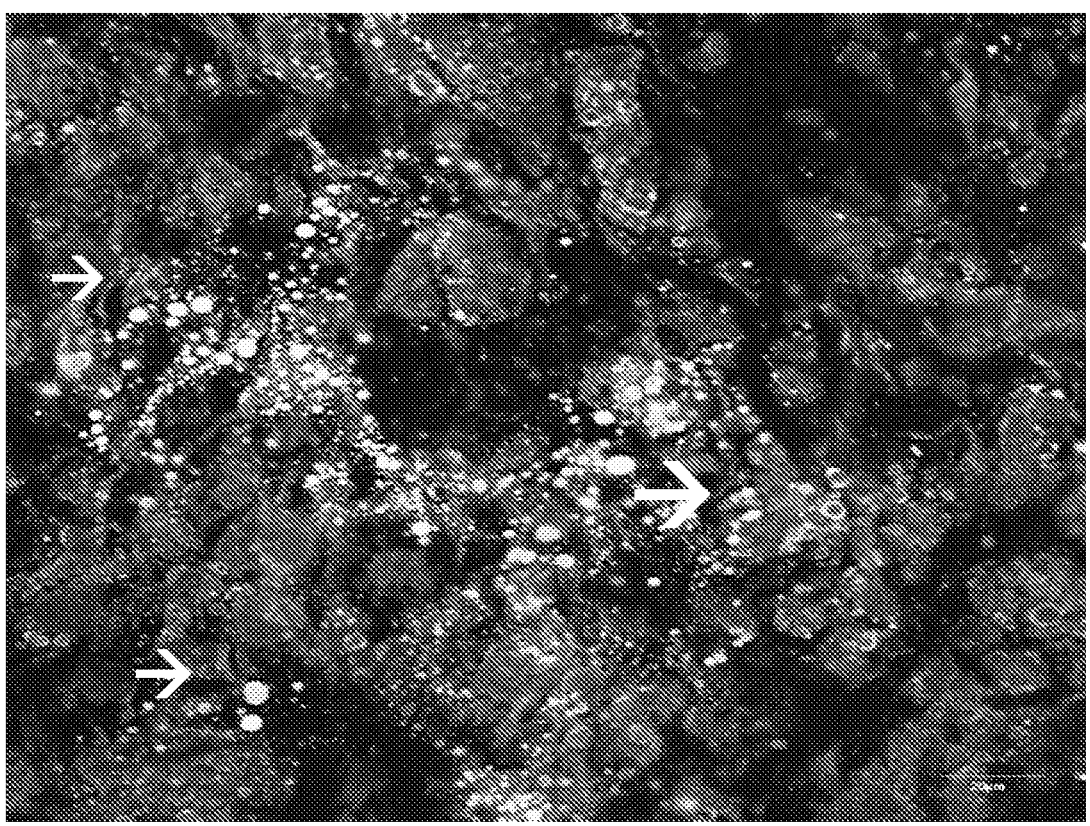
FIG. 4: Shows snapshots of one channel (in original green channel converted to the grey-scale picture) recording using confocal microscopy of macrophages (indicated with *; loaded with FITC-ferritin) and cancer cell (indicated with arrow; stained with red label and therefore not observed in green channel before ferritin uptake) in vitro taken at the starting time point (A) and after time long enough to fill cancer cell with ferritin (B). FITC-ferritin was dynamically transported to the cancer cell (accumulating firstly in the vesicles; then spreading to the whole cytoplasm as seen at this image (the cell appeared in green channel).
Figure 10:
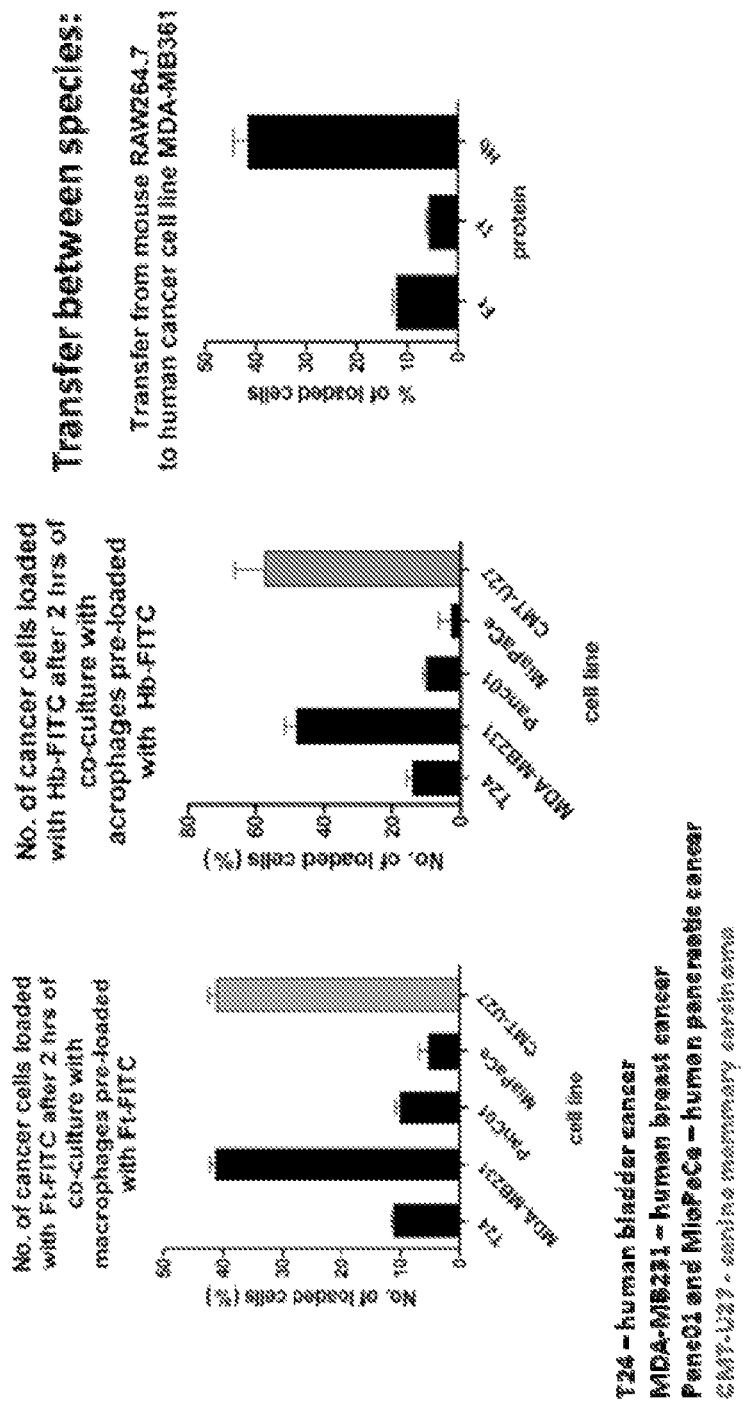
FIG. 10: Shows transfer of ferritin, haemoglobin and transferrin from macrophage to various cancer cells.
Figure 11:
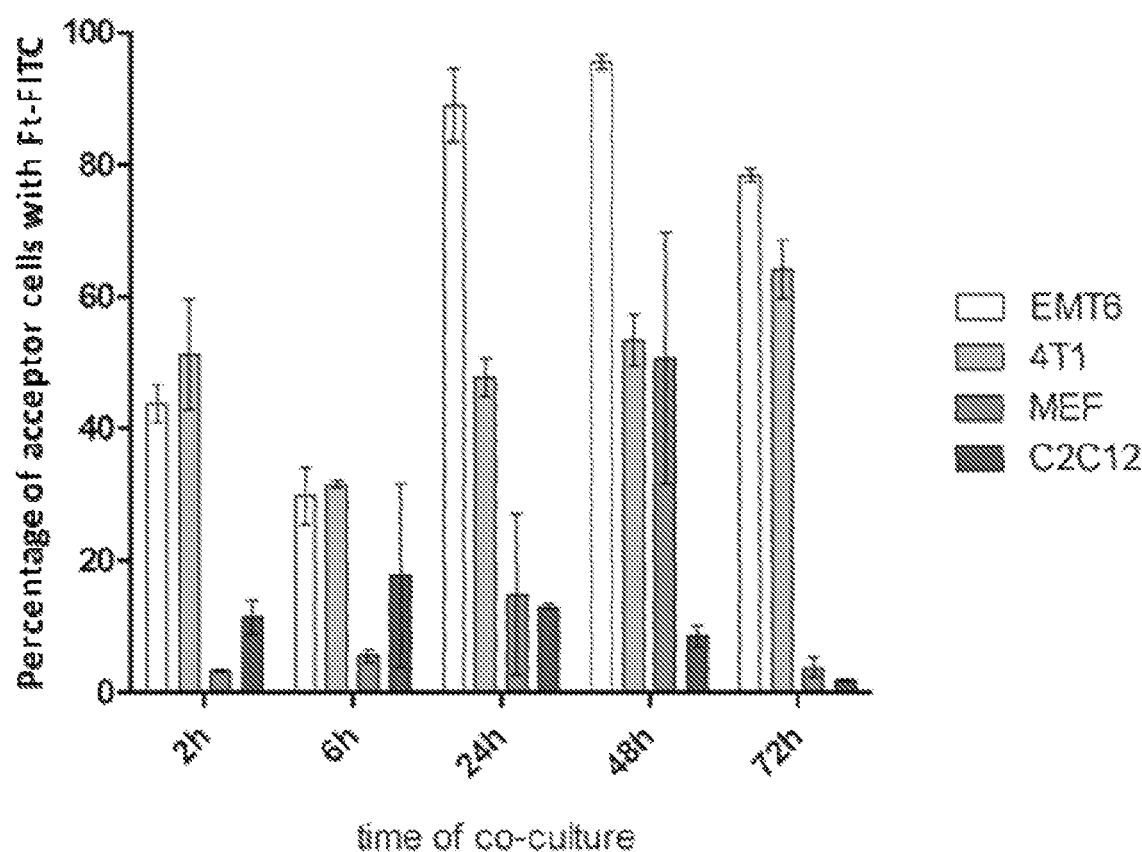
FIG. 11: Shows the transfer of ferritin from macrophage to cancer and non-cancer cells.
Figure 13:
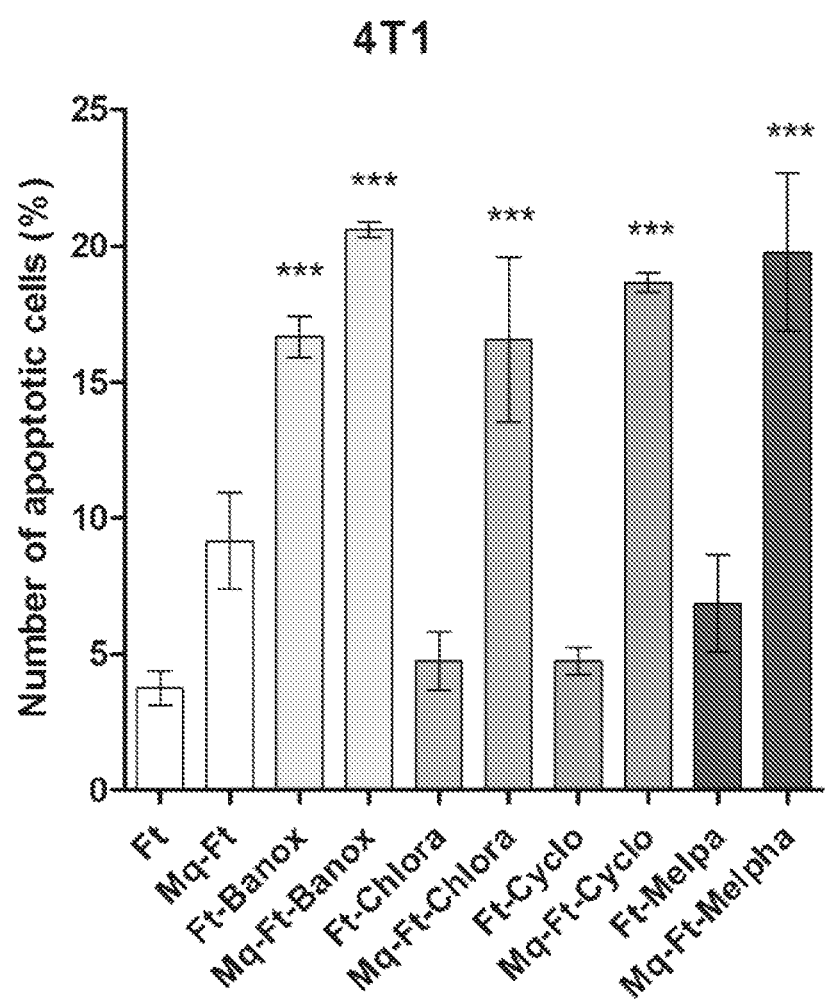
FIG. 13: Shows the apoptosis in cancer cells that received ferritin with encapsulated various anticancer agents from co-cultured macrophages or soluble ferritin with the same agents.

Example 11—Ferritin/Haemoglobin/Transferrin-Macrophage Complex as Useful Delivery Tool to Cancer Cells The macrophages from Example 1 prepared as described in Examples 8, 9 and 10, very easily transport ferritins, haemoglobins, transferrins to the cancer cells: mouse mammary cancer, colon cancer, canine mammary cancer, human breast, pancreatic, and bladder cancer (FIGS. 4, 10). Moreover, this transfer is much more specific to cancer cells than to non-cancer cells (FIG. 11). However, in case of cancer cells the ratio of both cell types is crucial. The more macrophages the better and faster the transport is. The most efficient transfer to the cancer cells was observed when ratio of macrophages to cancer cells was 1:1 or more.

Figure 6:
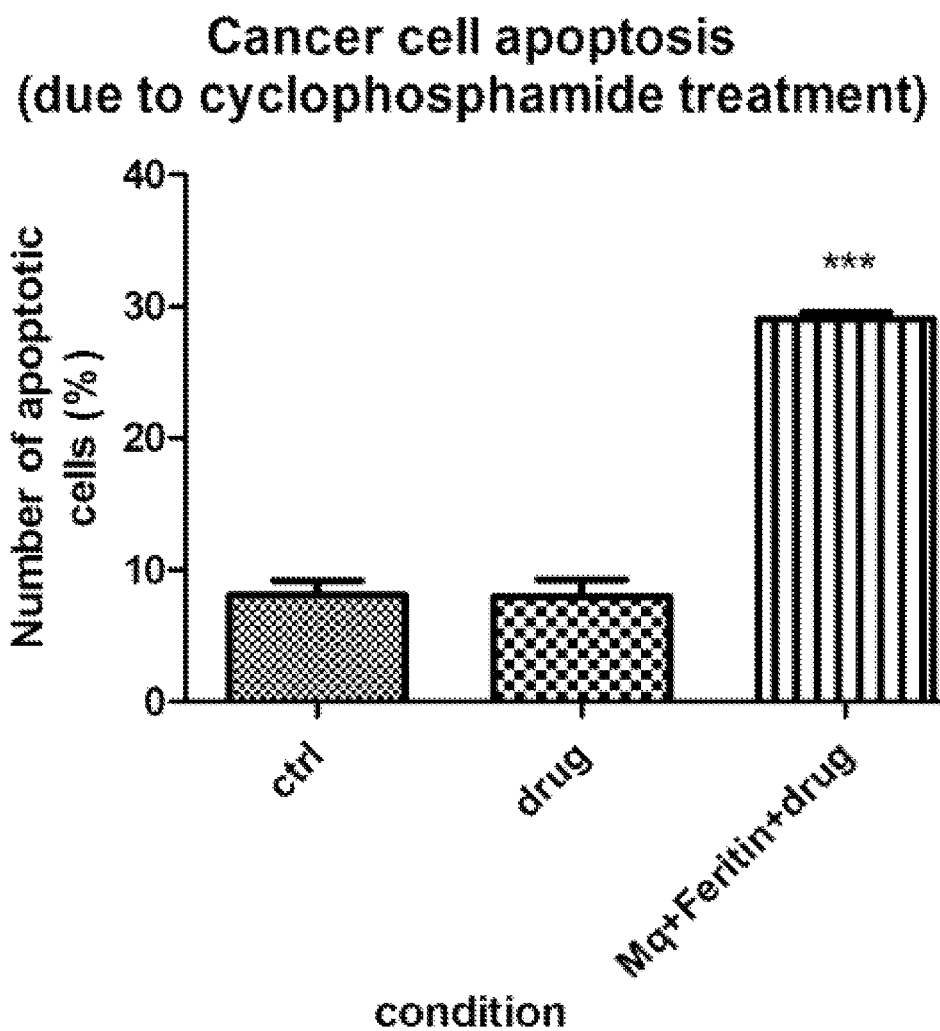
FIG. 6: Shows tumour cells apoptosis caused by treatment with cyclophosphamide and cyclophosphamide encapsulated in ferritins loaded to macrophages (given at the same doses).

This transfer occurred not only when the protein carriers are conjugated with fluorescent label (e.g. FITC or Alexa610), but also when they were conjugated/encapsulated with other compounds, e.g. anticancer drugs (FIG. 12 shows this transfer of ferritin encapsulated with fluorescent hypoxia activated prodrug—banoxantrone). This transfer of compounds conjugated with anticancer drugs made the effect inducing apoptosis in cancer cells (FIG. 6, 13).

Figure 14:
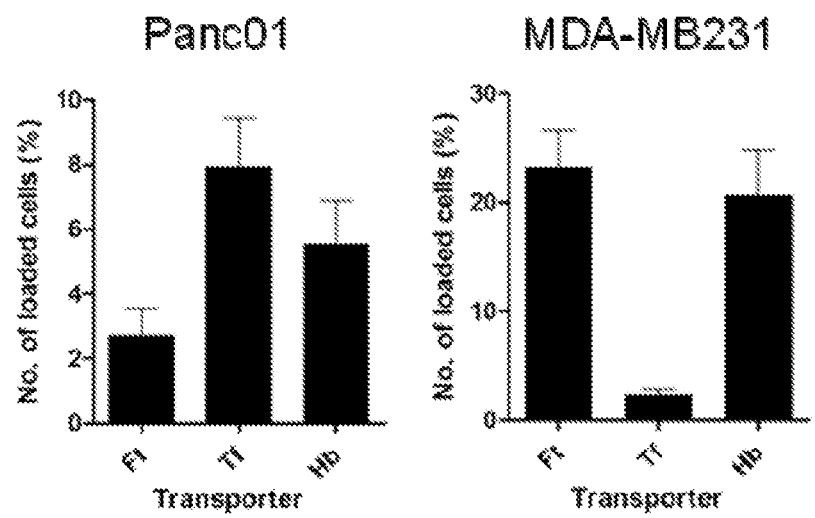
FIG. 14: Shows the transfer of ferritin, haemoglobin and transferrin from monocyte to various cancer cells.

Example 12—Ferritin/Haemoglobin/Transferrin-Monocyte Complex as Useful Delivery Tool to Cancer Cells The monocytes from Example 2 prepared as described in Examples 8, 9 and 10, very easily transport ferritins, haemoglobins, transferrins to the cancer cells (FIG. 14). However, the ratio of both cell types is crucial. The more monocytes the better and faster the transport is. The most efficient transfer to the cancer cells was observed when ratio of monocytes to cancer cells was 1:1 or more.

Figure 15:
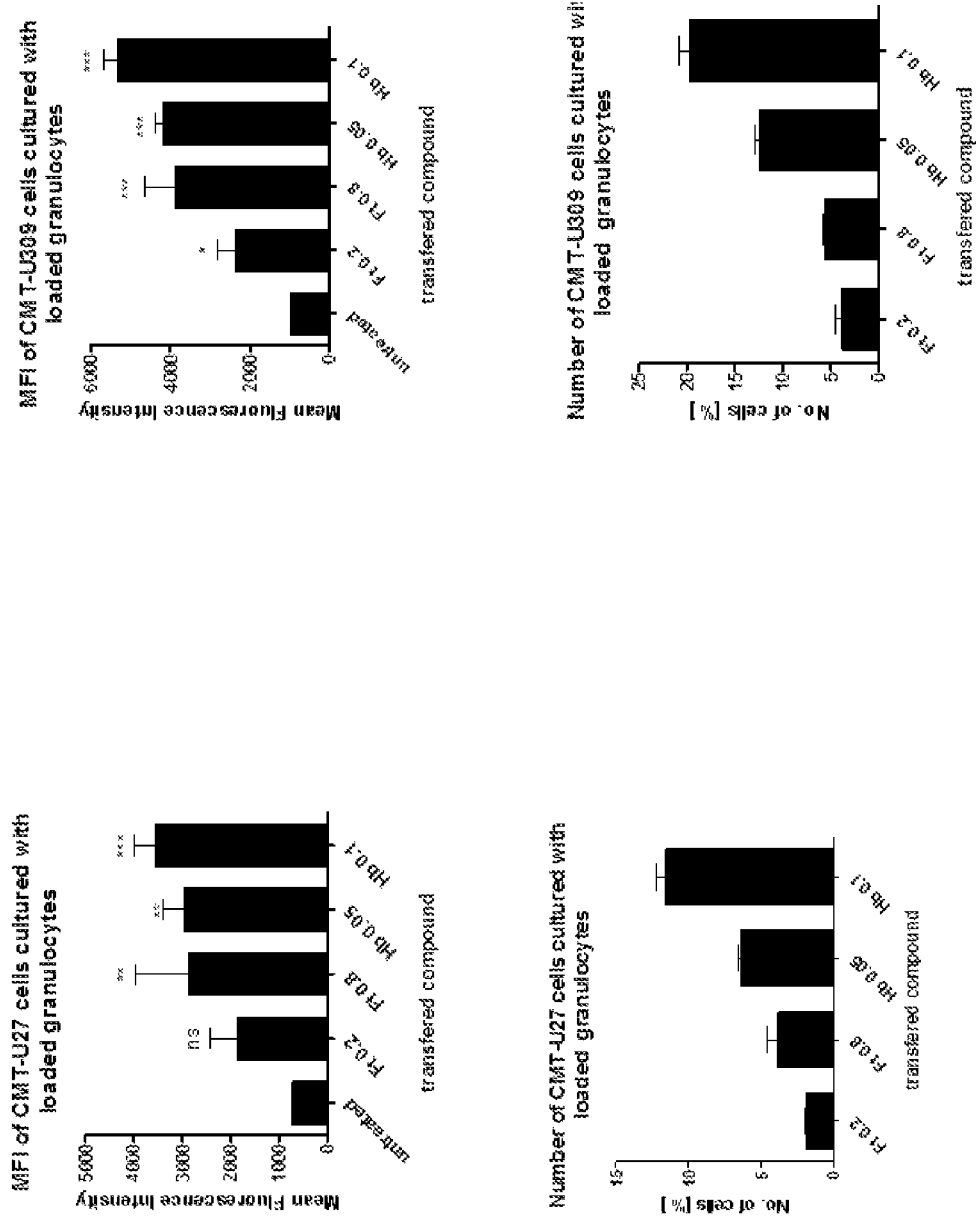
FIG. 15: Shows the transfer of ferritin and haemoglobin from granulocyte to various cancer cells.

Example 13—Ferritin/Haemoglobin/Transferrin-Granulocyte Complex as Useful Delivery Tool to Cancer Cells The granulocytes from Example 3 prepared as described in Examples 8, 9 and 10, very easily transport ferritins, haemoglobins, transferrins to the cancer cells (FIG. 15). However, the ratio of both cell types is crucial. The more granulocytes the better and faster the transport is. The most efficient transfer to the cancer cells was observed when ratio of granulocytes to cancer cells was 1:1 or more.

Figure 16:
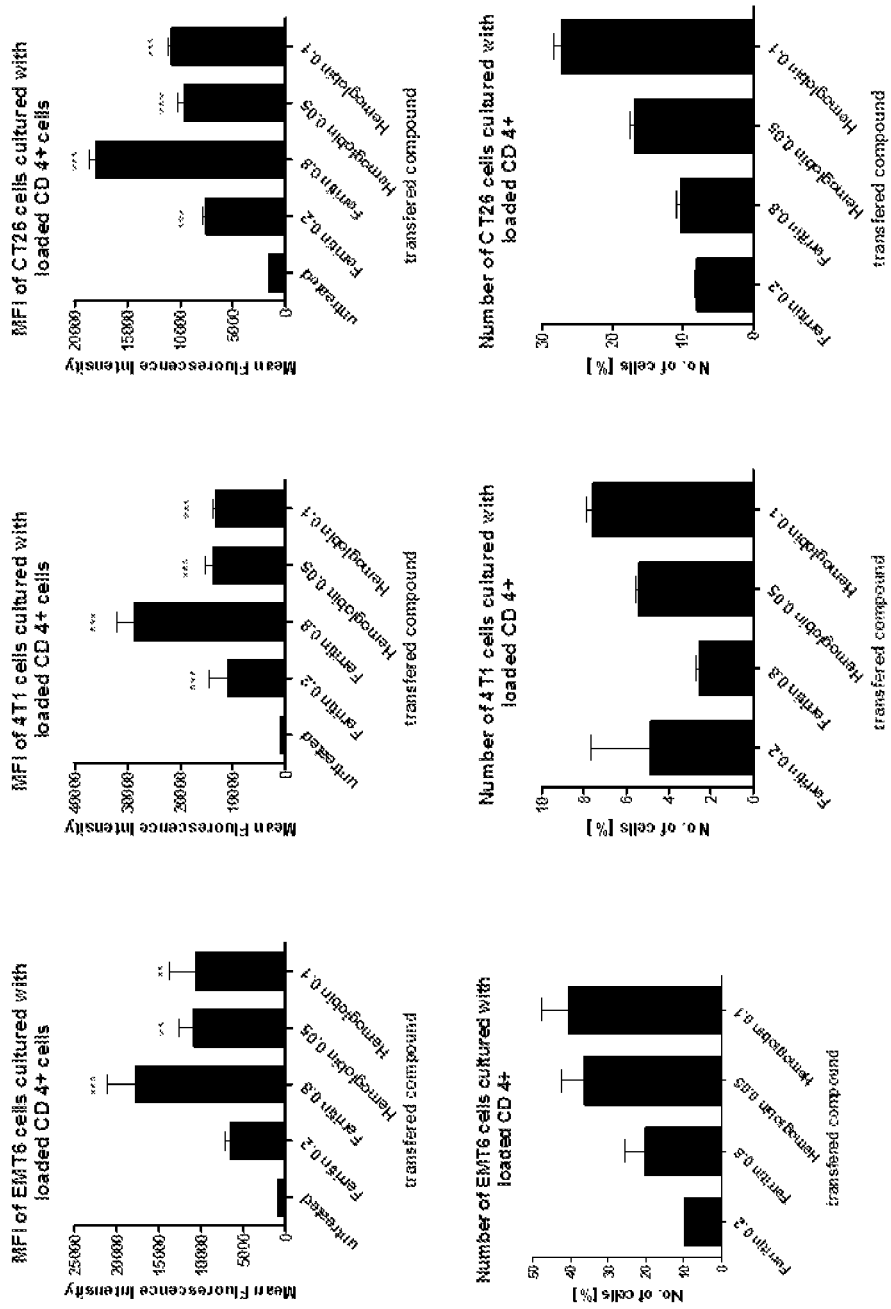
FIG. 16: Shows the transfer of ferritin and haemoglobin from lymphocyte to various cancer cells.

Example 14—Ferritin/Haemoglobin/Transferrin-Lymphocyte Complex as Useful Delivery Tool to Cancer Cells The lymphocytes from Example 4 prepared as described in Examples 8, 9 and 10, very easily transport ferritins, haemoglobins, transferrins to the cancer cells (FIG. 16). However, the ratio of both cell types is crucial. The more lymphocytes the better and faster the transport is. The most efficient transfer to the cancer cells was observed when ratio of lymphocytes to cancer cells was 1:1 or more.

Figure 3:
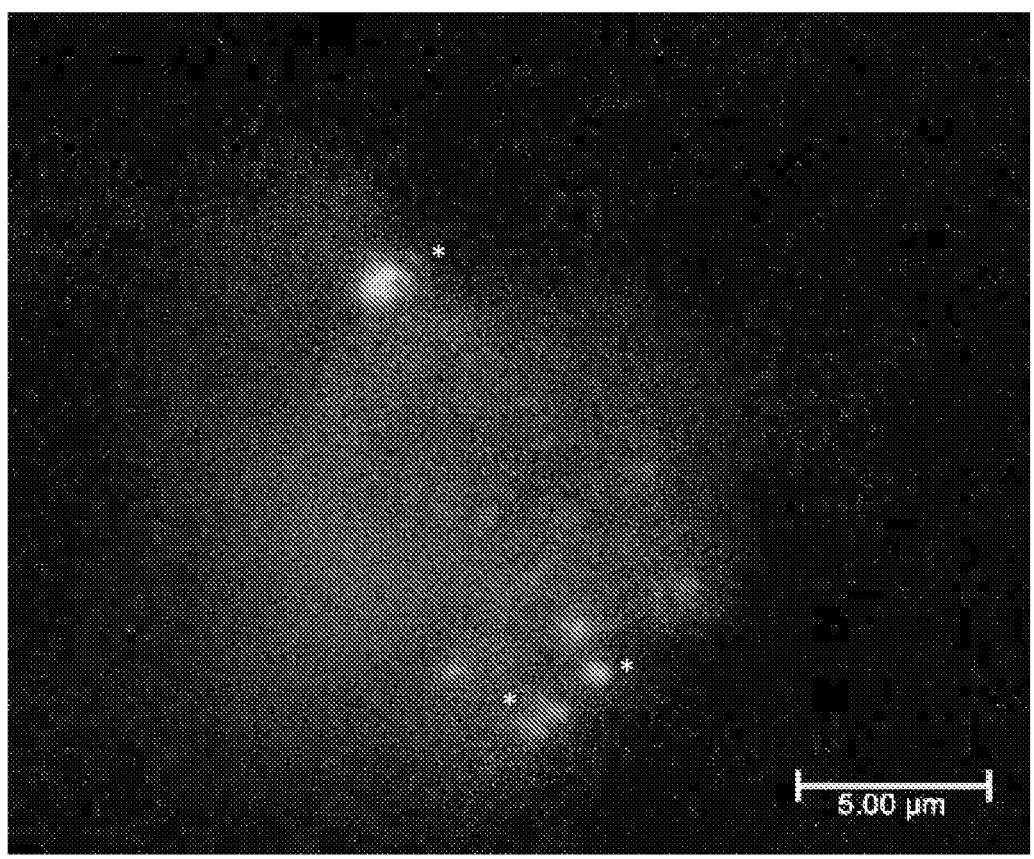
FIG. 3: Shows confocal microscopy image of tumour tissue mouse injected with mammary cancer cells and given i.v. macrophages loaded with FITC-ferritin (asterix)—it is clearly observed, not only in macrophages but also in cancer cells, that ferritin-FITC spread within all tumour mass.
Figure 17:
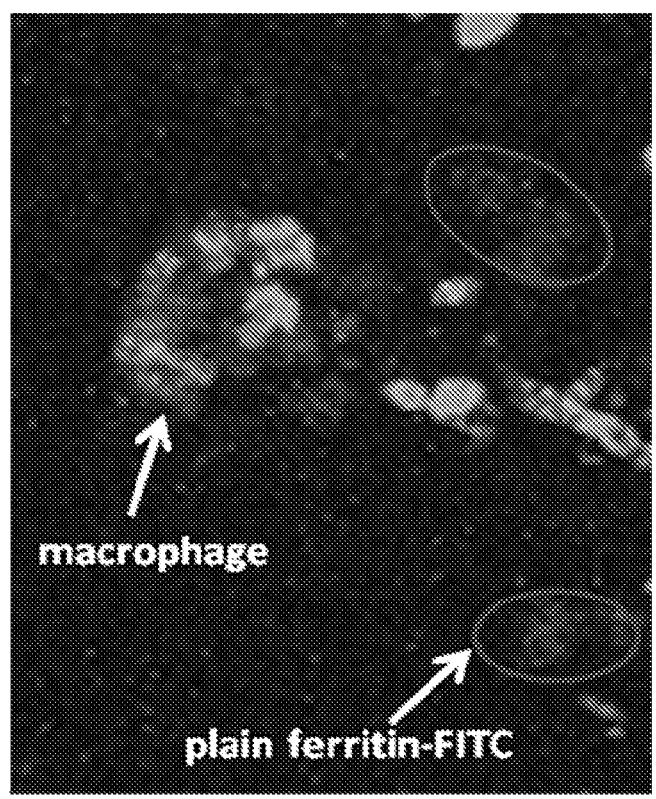
FIG. 17: Shows the picture from two-photon microscopy showing tumour from a mouse that received pre-labeled (before administration) macrophages containing Ferritin-FITC.
Figure 18:
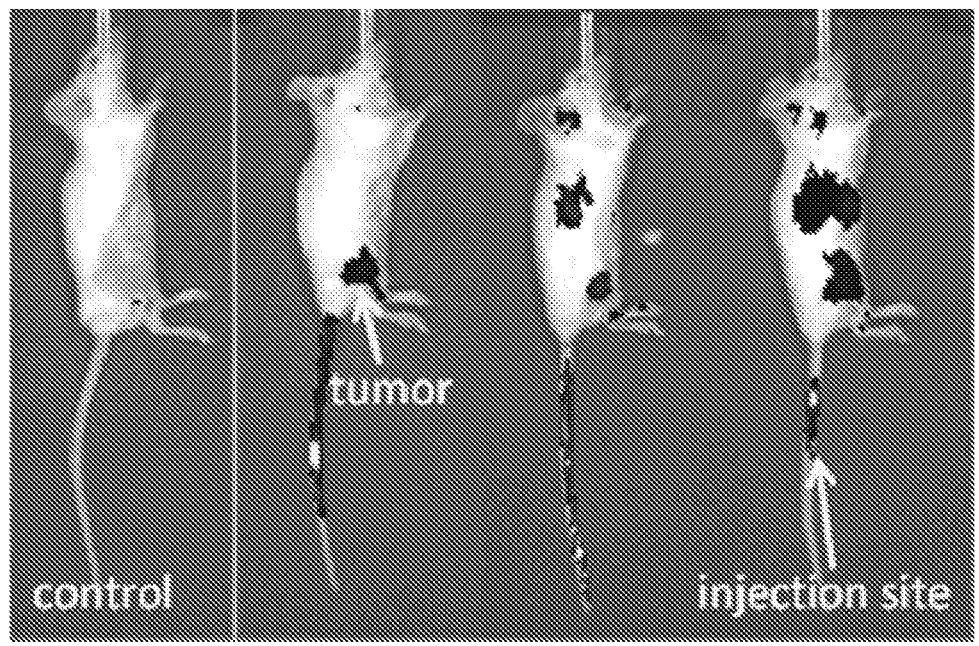
FIG. 18: Shows the whole body imaging of mice that intravenously received labeled macrophages, showing their accumulation in the tumour site and their distribution in other organs.
Figure 19:
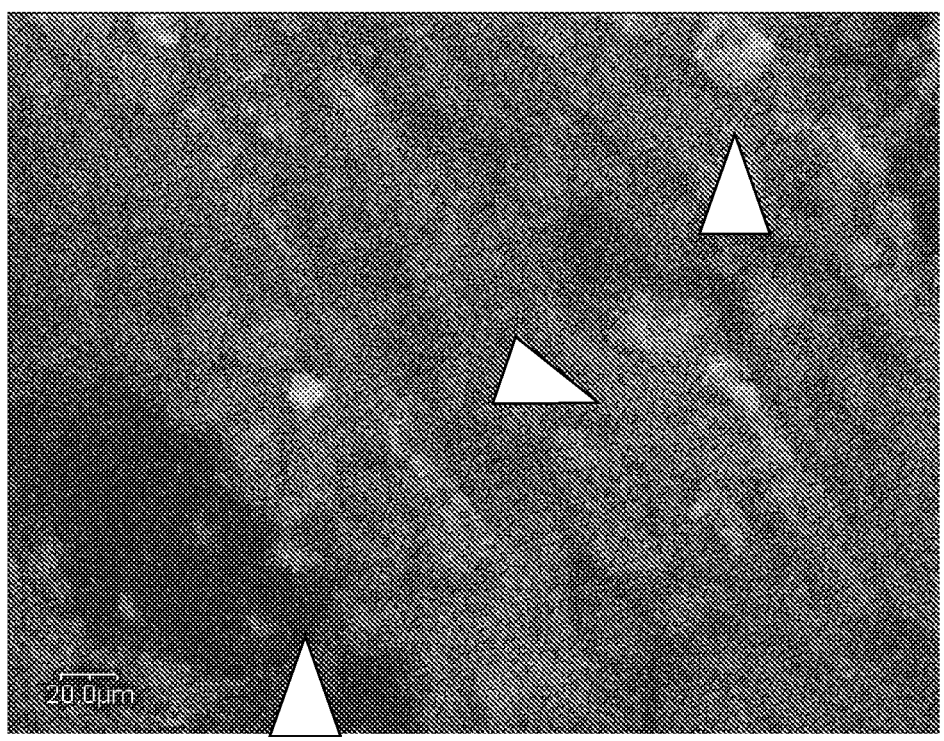
FIG. 19: Shows the migration of macrophages to hypoxic tissue, a cross-section of the tumour from a mouse that was administered intravenously with pre-labeled macrophages, tumour hypoxic areas are visualized with a hypoxia marker—pimonidazolone.
Figure 20:
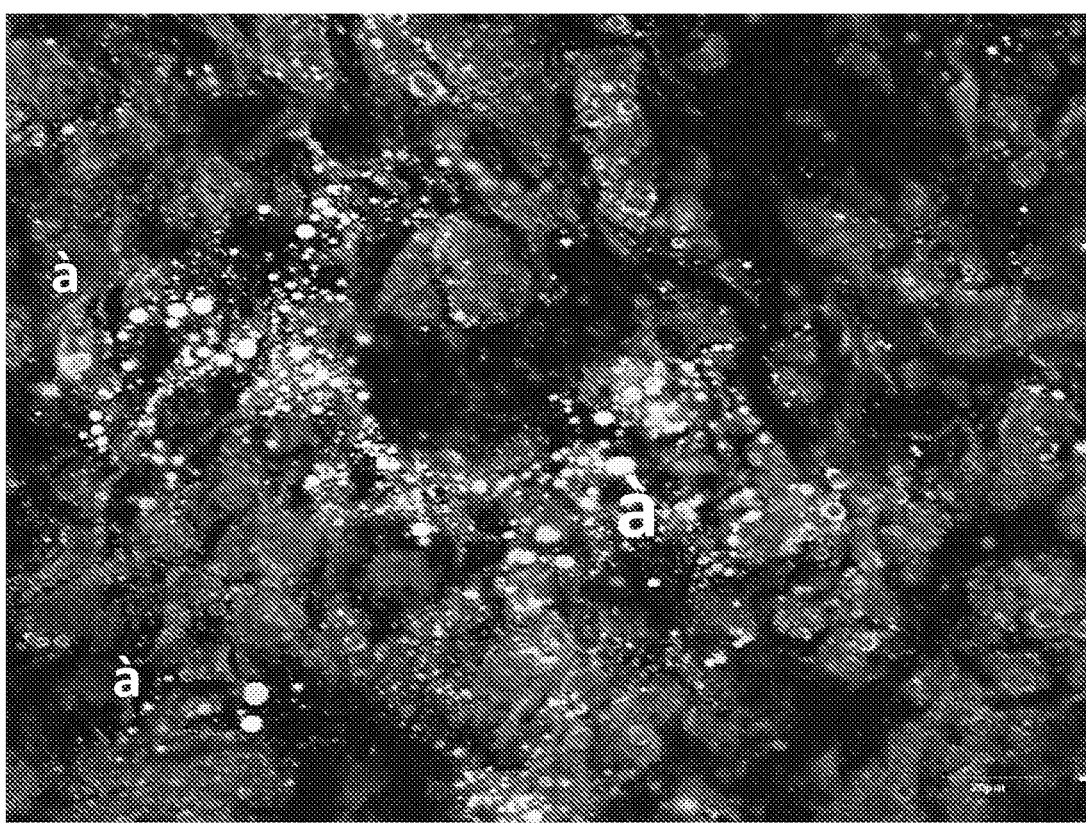
FIG. 20: Shows the presents localization of vesicles containing FITC-laded ferritin (round objects) in the microenvironment inside the tumour mass. Macrophages containing FITC-laded ferritin were administered intravenously to the mouse.

Example 15—Leukocyte-Protein Carrier Complex as Useful Targeted Drug Delivery Agent to Hypoxic Regions Macrophages prepared as above are injected into the tail vein of animal with the tumour (appropriate number of macrophages should be adjusted to the tumour size, stage of development and presence of metastases). As it is shown on FIGS. 2, and 17 they specifically reach the tumour (after a few hrs) and also disperse in other organs of the whole animal (FIG. 18). Moreover, as it is shown on FIG. 19, in hypoxic model they are also able to migrate to the avascular and hypoxic sites and to transfer carrier proteins to cancer cells (FIGS. 3, and 20).

For the imaging purposes, 1-50 millions of macrophages were injected into the tail vein of mammary or colon cancer tumour-bearing animal. Before, macrophages were pre-labeled with Cell Tracker and loaded with ferritin-FITC (as shown in Example 8). Using two-photon of the tumour mass 8 hrs after administration of macrophages the presence of macrophages carrying Ferritin-FITC was detected (FIG. 17). Their specific targeting of tumour but also their migration to other organs was shown using whole animal body imaging (IVIS) after macrophage pre-labeling using DIR cytoplasmic dye (FIG. 18).

Figure 5:
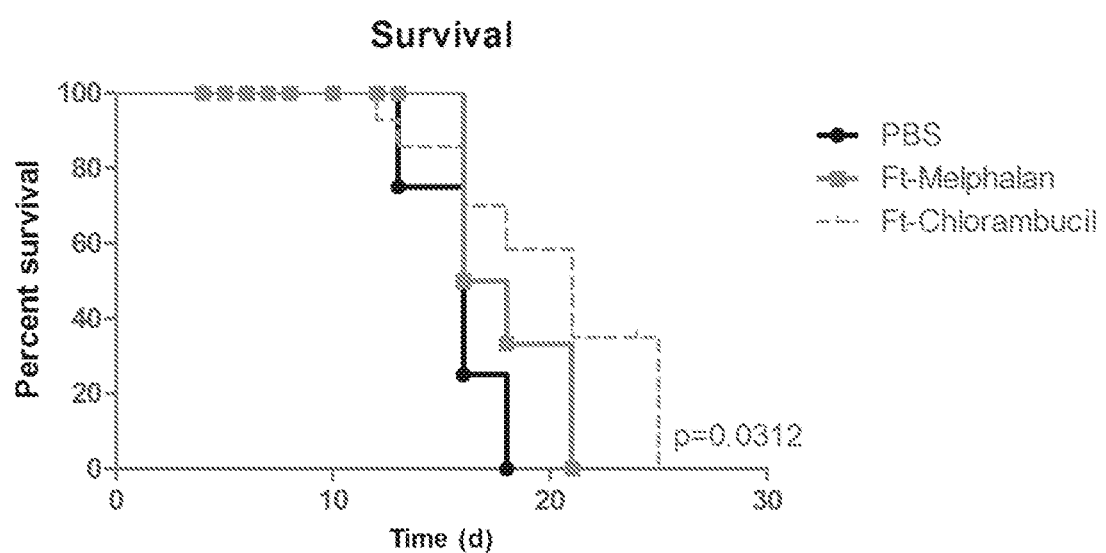
FIG. 5: Shows survival of mice receiving placebo and macrophages loaded with ferritin-coupled melphalan and ferritin-coupled chlorambucil.

The 1-10 millions of macrophages loaded with ferritin encapsulated cyclophosphamide, melphalan and ferritin encapsulated chlorambucil were injected i.v. into the tumour-bearing mice (300 000-500 000 of EMT6 cells injected into the skin flank). We made 3 injections of macrophages every third day (on the day 5, 8 and 11 after cancer cells injection or on the day 7, 10 and 13 after cancer cells injection) or five consecutive injections every day and we observed increased mouse survival (FIG. 5).

Figure 7:
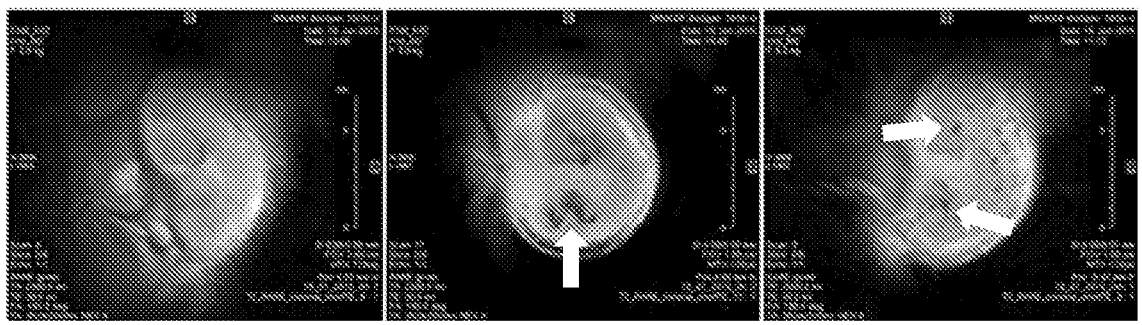
FIG. 7: Shows MRI images of mouse mammary tumour. The mouse was treated (at time point 0 h) with macrophages (i.v. injection) loaded with ferritin Fh. Then we observed increased diameter of blood vessels (arrow) filled with injected macrophages (giving significant T2-signal reduction) and afterword macrophages spread to the tissue (spot-like pattern; arrows). These changes (in the same time points) were observed in all examined mice.
Figure 21:
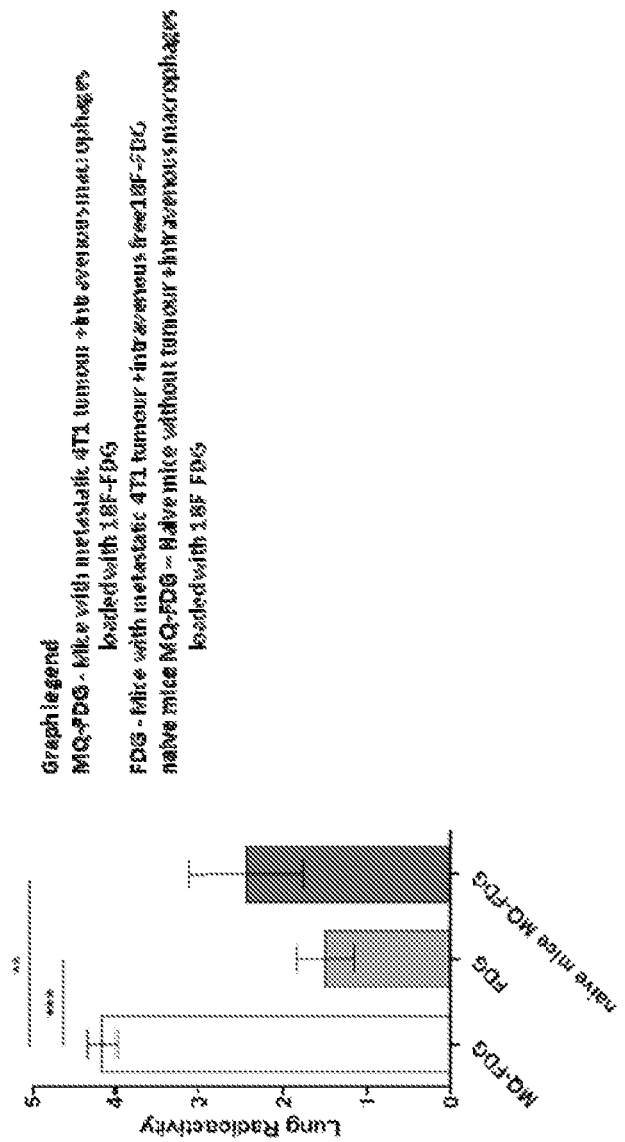
FIG. 21: Shows the signal recorded by PET from a whole-body analysis of mice with the metastatic 4T1 cancer. Mice received intravenously macrophages loaded with 18F-FDG. Signal accumulation is increased in the lungs of mice with micrometastases (confirmed by pathology examination). Mice receiving plain 18F-FDG, or mice without 4T1 cancer had lower PET signal.

Example 16—Leukocyte-Protein Carrier Complex or Labeled Leukocyte as Useful Imaging Tool The targeting of the targeted delivery system described in present invention can be followed by coupling the ferritin to a contrast agent. As it is presented on FIG. 21, after injection of 1-50 ml of macrophages loaded with ferritin coupled as described in Example 8 with a contrast agent (in this case: ferrihydrite, however the same results are obtained with isotope, e.g. $^{123}$I) or labeled with isotope (in this case $^{18}$F-FDG) (FIG. 21) they can be easily detected by MRI, PET or SPECT. In this example (FIG. 7), mammary-tumour bearing mice were imaged using MRI at 3, 22 and 24 hours after i.v. injection of macrophages loaded with ferritin Fh.

The mouse was treated (at time point 0 h) with macrophages. Then increased diameter of blood vessels (arrow) filled with injected macrophages (giving significant T2-signal reduction) has been observed and afterword macrophages spread to the tissue (spot-like pattern; arrows). These changes (in the same time points) were observed in all examined mice.

Macrophages were also labeled with $^{18}$F-FDG (5-50 mln) and imaged using PET at 1 h after i.v. administration to the tumour-bearing mice. These mice were inoculated with 4T1 metastatic cell line 3 weeks before the experiment and metastases in the lungs, liver and spleen were histopatologically confirmed. At FIG. 21 it is seen that macrophages migrated to the regions with metastatic tumours allowing their visualization at PET.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The present invention also relates to the following aspects and preferred embodiments of these aspects. The definitions provided above similarly apply to below aspects and embodiments.

1. Targeted delivery system comprising an activated macrophage loaded with ferritin carrying an active ingredient.
2. The targeted delivery system according to embodiment 1, wherein the active ingredient carried by ferritin is an anticancer drug.
3. The targeted delivery system according to embodiment 2, wherein the anticancer drug is an apoptosis-inducing drug.
4. The targeted delivery system according to embodiment 2, wherein the anticancer drug is selected from the group comprising cyclophosphamide, chlorambucil, melphalan, bendamustine and banoxantrone.
5. The targeted delivery system according to embodiment 1, wherein the active ingredient is a hypoxia-activated prodrug.
6. The targeted delivery system according to embodiment 5, wherein the hypoxia-activated prodrug is TH-302.
7. Method of preparation of the targeted delivery system comprising an activated macrophage loaded with ferritin carrying an active ingredient comprising steps of
a) ferritin purification;
b) obtaining ferritin carrying an active ingredient by linking of ferritin with said active ingredient;
c) activation of isolated macrophages;
d) incubation of macrophages in solution of ferritin carrying an active ingredient as obtained in step b) for a time and at the ferritin concentration sufficient to ensure full load of ferritin carrying an active ingredient into macrophages.
8. The method of embodiment 7, wherein activated macrophages are bone marrow originated macrophages.
9. The method of embodiment 7, wherein activated macrophages are blood originated macrophages.
10. The method of embodiment 7, wherein activated macrophages are derived from macrophage cell lines.
11. The method of any one of embodiments 7-10, wherein activated macrophages are macrophages polarized towards M1 or M2.
12. The method of embodiment 11 wherein activated macrophages have been polarized towards M2.

13. The method of embodiment 11 wherein activated macrophages have been manipulated with respect to iron metabolism.
14. The method of any one of embodiments 7-13, wherein the active ingredient carried by ferritin is an anticancer drug.
15. The method of embodiment 14, wherein the anticancer drug is an apoptosis/autophagy or necrosis-inducing drug.
16. The method of embodiment 14, wherein the anticancer drug is selected from the group comprising cyclophosphamide, chlorambucil, melphalan, bendamustine and banoxantrone.
17. The method of any one of embodiments 7-13, wherein the active ingredient is a hypoxia-activated prodrug.
18. The method of embodiment 17, wherein the hypoxia-activated prodrug is TH-302.
19. Targeted delivery system as defined in any of embodiments 1-7 for use as anticancer drug targeted delivery system.
20. Targeted delivery system as defined in any of embodiments 1-7 for use in preventing/treatment of solid tumour growth.
21. Use of a targeted delivery system as defined in any of embodiments 1-7 in treatment of inflammatory disease.
22. Use of a targeted delivery system as defined in any of embodiments 1-7 in treatment or imagining of ischemic areas.

In a preferred embodiment the present invention does not comprise the subject-matter of items 1 to 22 above.

The invention claimed is:

1. An isolated targeted delivery system comprising a macrophage comprising within said macrophage a complex of ferritin and an anti-cancer drug, wherein the anti-cancer drug is encapsulated within a ferritin multimer, and wherein there is no covalent or non-covalent bond between the ferritin and the anti-cancer drug.

2. The isolated targeted delivery system according to claim 1, wherein macrophage is an activated macrophage.

3. The isolated targeted delivery system of claim 2, wherein the activated macrophage:
   (i) is producible by in vitro incubation of a monocyte or macrophage with a factor capable of altering expression markers on macrophages;
   (ii) is characterized by expression of at least one of following antigens: CD64, CD86, CD16, CD32, high expression of MHCII, and/or production of iNOS and/or IL-12;
   (iii) is producible by in vitro incubation of a monocyte or macrophage with at least one inducer, wherein the at least one inducer is a factor capable of inducing the ability of the macrophage to phagocytose;
   (iv) is characterized by expression of at least one of following antigens: CD204, CD206, CD200R; CCR2, transferrin receptor (TfR), CXC-motive chemokine receptor 4 (CXCR4), CD163, and/or T cell immunoglobulin-domain and mucin-domain 2 (TIM-2), and/or show low expression of MHCII;
   (v) has the ability to phagocytose; and/or
   (vi) is capable of cytokine secretion, or production of inducible nitric oxide synthetase (iNOS) (or other pro-inflammatory compounds), arginase or other immunosuppressive/anti-inflammatory compounds.

4. The targeted delivery system according to claim 3, wherein the activated macrophage is producible by the in vitro incubation of a monocyte or macrophage with at least one inducer, wherein the at least one inducer is:
   (i) a M1 inducer selected from the group consisting of LPS, INF-γ, GM-CSF and viral and bacterial infection; or
   (ii) a M2 inducer selected from the group consisting of IL-4, IL-10, IL-13, immune complex of an antigen and antibody, IgG, heat activated gamma-globulin, glucocorticosteroid, TGF-β, IL-1R, CCL-2, IL-6, M-CSF, PPARγ agonist, Leukocyte inhibitory factor, adenosine, helminth and fungal infection.

5. The isolated targeted delivery system according to claim 1, wherein the macrophage is an activated M2 macrophage:
   (i) producible by in vitro incubation of a monocyte or macrophage with at least one M2 inducer selected from the group consisting of IL-4, IL-10, IL-13, immune complex of an antigen and antibody, IgG, heat activated gamma-globulin, glucocorticosteroid, TGF-β IL-1R, CCL-2, IL-6, M-CSF, PPARγ agonist, Leukocyte inhibitory factor, adenosine, helminth and fungal infection; and/or
   (ii) selected from the group consisting of a $CD11b^+$ $CCR2^+$ M2 macrophage, a $CD11b^+$ $CD204^+$ M2 macrophage, a $CD11b^+$ $CD206^+$ M2 macrophage, a $CD11b^+$ $CD204^+$ $CD206^+$ M2 macrophage, a $CD11b^+$ Mayor Histocompatibility Complex 11 ($MHCII^+$) (low or hi expression) M2 macrophage, a CD11b⁺ CD200R⁺ M2 macrophage and a CD11b⁺ CD163⁺ M2 macrophage.

6. The isolated targeted delivery system according to claim 1, wherein the anticancer drug is selected from the group consisting of an apoptosis-inducing drug, an alkylating substance, anti-metabolites, antibiotics, epothilones, nuclear receptor agonists and antagonists, an anti-androgene, an anti-estrogen, a platinum compound, a hormone, a antihormone, an interferon, an inhibitor of cell cycle-dependent protein kinases (CDKs), an inhibitor of cyclooxygenases and/or lipoxygenases, a biogeneic fatty acid, a biogenic fatty acid derivative, including prostanoids and leukotrienes, an inhibitor of protein kinases, an inhibitor of protein phosphatases, an inhibitor of lipid kinases, a platinum coordination complex, an ethyleneimine, a methylmelamine, a triazine, a *vinca* alkaloid, a pyrimidine analog, a purine analog, an alkylsulfonate, a folic acid analog, an anthracendione, a substituted urea, and a methylhydrazin derivative, an ene-diyne antibiotic, a maytansinoid an auristatine derivate, immune check-point inhibitor, and an inhibitor of tumour-specific protein or marker.

7. The isolated targeted delivery system according to claim 1 wherein the anticancer drug is selected from the group consisting of acediasulfone, aclarubicine, ambazone, aminoglutethimide, L-asparaginase, azathioprine, banoxantrone, bendamustine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethyl stilbestrole, docetaxel, doxorubicin, enediynes, epirubicin, epothilone B, epothilone D, estramucin phosphate, estrogen, ethinylestradiole, etoposide, flavopiridol, floxuridine, fludarabine, fluorouracil, fluoxymesterone, flutamide fosfestrol, furazolidone, gemcitabine, gonadotropin releasing hormone analog, hexamethylmelamine, hydroxycarbamide, hydroxymethylnitrofurantoin, hydroxyprogesteronecaproat, hydroxyurea, idarubicin, idoxuridine, ifosfamide, interferon α, irinotecan, leuprolide, lomustine, lurtotecan, mafenide sulfate olamide, mechlorethamine, medroxyprogesterone acetate, megastrolacetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, scriflavinium chloride, semustine streptozocine, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxazole, co-trimoxazole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosteronpropionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin.

8. The isolated targeted delivery system according to claim 1 wherein the anticancer drug is a proliferation inhibiting protein, a siRNA or a DNAzyme.

9. A pharmaceutical composition comprising the isolated targeted delivery system of claim 1 and a pharmaceutically acceptable carrier and/or suitable excipient(s).

\* \* \* \* \*

```
                        SEQUENCE LISTING

<160> NUMBER OF SEQ ID NOS: 28

<210> SEQ ID NO 1
<211> LENGTH: 132
<212> TYPE: PRT
<213> ORGANISM: Artificial Sequence
<220> FEATURE:
<223> OTHER INFORMATION: Minimal consensus sequence of mammalian
      ferritin H chain
<220> FEATURE:
<221> NAME/KEY: MISC_FEATURE
<222> LOCATION: (5)..(5)
<223> OTHER INFORMATION: Xaa at position 5 may be present or absent, if
      present it means any naturally occurring amino acid, preferably
      Ile
<220> FEATURE:
<221> NAME/KEY: MISC_FEATURE
<222> LOCATION: (6)..(6)
<223> OTHER INFORMATION: Xaa at position 6 means any naturally occurring
      amino acid, preferably Asn
<220> FEATURE:
<221> NAME/KEY: MISC_FEATURE
<222> LOCATION: (14)..(14)
<223> OTHER INFORMATION: Xaa at position 14 means any naturally
      occurring amino acid, preferably Tyr
<220> FEATURE:
<221> NAME/KEY: MISC_FEATURE
<222> LOCATION: (24)..(24)
<223> OTHER INFORMATION: Xaa at position 24 means any naturally
      occurring amino acid, preferably Tyr or Cys, more preferably Tyr
<220> FEATURE:
<221> NAME/KEY: MISC_FEATURE
<222> LOCATION: (66)..(66)
<223> OTHER INFORMATION: Xaa at position 66 means any naturally
      occurring amino acid, preferably Phe
<220> FEATURE:
<221> NAME/KEY: MISC_FEATURE
<222> LOCATION: (68)..(68)
<223> OTHER INFORMATION: Xaa at position 68 means any naturally
      occurring amino acid, preferably Gln
<220> FEATURE:
<221> NAME/KEY: MISC_FEATURE
<222> LOCATION: (75)..(75)
<223> OTHER INFORMATION: Xaa at position 75 means any naturally
      occurring amino acid, preferably Arg or Cys, more preferably Cys
<220> FEATURE:
<221> NAME/KEY: MISC_FEATURE
<222> LOCATION: (90)..(90)
<223> OTHER INFORMATION: Xaa at position 90 means any naturally
      occurring amino acid, preferably His
<220> FEATURE:
<221> NAME/KEY: MISC_FEATURE
<222> LOCATION: (94)..(94)
<223> OTHER INFORMATION: Xaa at position 94 means any naturally
      occurring amino acid, preferably Ser or Asn, more preferably Asn
<220> FEATURE:
<221> NAME/KEY: MISC_FEATURE
<222> LOCATION: (120)..(120)
<223> OTHER INFORMATION: Xaa at position 120 may be present or absent,
```

```
        if present it means any naturally occurring amino acid, preferably
        His or Tyr, more preferably His
<220> FEATURE:
<221> NAME/KEY: MISC_FEATURE
<222> LOCATION: (123)..(123)
<223> OTHER INFORMATION: Xaa at position 123 means any naturally
        occurring amino acid, preferably Asn or Ser, more preferably Asn
<220> FEATURE:
<221> NAME/KEY: MISC_FEATURE
<222> LOCATION: (128)..(128)
<223> OTHER INFORMATION: Xaa at position 128 means any naturally
        occurring amino acid, preferably Ala or Ser, more preferably Ala

<400> SEQUENCE: 1

Ser Glu Ala Ala Xaa Xaa Arg Gln Ile Asn Leu Glu Leu Xaa Ala Ser
1               5                   10                  15

Tyr Val Tyr Leu Ser Met Ser Xaa Tyr Phe Asp Arg Asp Asp Val Ala
            20                  25                  30

Leu Lys Asn Phe Ala Lys Tyr Phe Leu His Gln Ser His Glu Glu Arg
        35                  40                  45

Glu His Ala Glu Lys Leu Met Lys Leu Gln Asn Gln Arg Gly Gly Arg
    50                  55                  60

Ile Xaa Leu Xaa Asp Ile Lys Lys Pro Asp Xaa Asp Asp Trp Glu Ser
65                  70                  75                  80

Gly Leu Asn Ala Met Glu Cys Ala Leu Xaa Leu Glu Lys Xaa Asn Gln
                85                  90                  95

Ser Leu Leu Glu Leu His Lys Leu Ala Thr Asp Lys Asn Asp Pro His
            100                 105                 110

Leu Cys Asp Phe Ile Glu Thr Xaa Tyr Leu Xaa Glu Gln Val Lys Xaa
        115                 120                 125

Ile Lys Glu Leu
    130

<210> SEQ ID NO 2
<211> LENGTH: 183
<212> TYPE: PRT
<213> ORGANISM: Artificial Sequence
<220> FEATURE:
<223> OTHER INFORMATION: Consensus sequence of mammalian ferritin H
        chain
<220> FEATURE:
<221> NAME/KEY: MISC_FEATURE
<222> LOCATION: (6)..(6)
<223> OTHER INFORMATION: Xaa at position 6 can be any naturally
        occurring amino acid, preferably Pro
<220> FEATURE:
<221> NAME/KEY: MISC_FEATURE
<222> LOCATION: (14)..(14)
<223> OTHER INFORMATION: Xaa at position 14 can be any naturally
        occurring amino acid, preferably His
<220> FEATURE:
<221> NAME/KEY: MISC_FEATURE
<222> LOCATION: (16)..(16)
<223> OTHER INFORMATION: Xaa at position 16 can be any naturally
        occurring amino acid, preferably Asp
<220> FEATURE:
<221> NAME/KEY: MISC_FEATURE
<222> LOCATION: (21)..(21)
<223> OTHER INFORMATION: Xaa at position 21 may be present or absent, if
        present it means any naturally occurring amino acid, preferably
        Ile
<220> FEATURE:
<221> NAME/KEY: MISC_FEATURE
<222> LOCATION: (22)..(22)
<223> OTHER INFORMATION: Xaa at position 22  means any naturally
        occurring amino acid, preferably Asn
<220> FEATURE:
<221> NAME/KEY: MISC_FEATURE
<222> LOCATION: (30)..(30)
```

```
<223> OTHER INFORMATION: Xaa at position 30 can be any naturally
      occurring amino acid, preferably Tyr
<220> FEATURE:
<221> NAME/KEY: MISC_FEATURE
<222> LOCATION: (40)..(40)
<223> OTHER INFORMATION: Xaa at position 40 can be any naturally
      occurring amino acid, preferably Tyr or Cys, more preferably Tyr
<220> FEATURE:
<221> NAME/KEY: MISC_FEATURE
<222> LOCATION: (82)..(82)
<223> OTHER INFORMATION: Xaa at position 82 can be any naturally
      occurring amino acid, preferably Phe
<220> FEATURE:
<221> NAME/KEY: MISC_FEATURE
<222> LOCATION: (84)..(84)
<223> OTHER INFORMATION: Xaa at position 84 can be any naturally
      occurring amino acid, preferably Gln
<220> FEATURE:
<221> NAME/KEY: MISC_FEATURE
<222> LOCATION: (91)..(91)
<223> OTHER INFORMATION: Xaa at position 91 can be any naturally
      occurring amino acid, preferably Arg or Cys, more preferably Cys
<220> FEATURE:
<221> NAME/KEY: MISC_FEATURE
<222> LOCATION: (106)..(106)
<223> OTHER INFORMATION: Xaa at position 106 can be any naturally
      occurring amino acid, preferably His
<220> FEATURE:
<221> NAME/KEY: MISC_FEATURE
<222> LOCATION: (110)..(110)
<223> OTHER INFORMATION: Xaa at position 110 can be any naturally
      occurring amino acid, preferably Asn or Ser, more preferably Asn
<220> FEATURE:
<221> NAME/KEY: MISC_FEATURE
<222> LOCATION: (137)..(137)
<223> OTHER INFORMATION: Xaa at position 137 can be any naturally
      occurring amino acid, preferably His or Tyr, more preferably His
<220> FEATURE:
<221> NAME/KEY: MISC_FEATURE
<222> LOCATION: (140)..(140)
<223> OTHER INFORMATION: Xaa at position 140 can be any naturally
      occurring amino acid, preferably Asn or Ser, more preferably Asn
<220> FEATURE:
<221> NAME/KEY: MISC_FEATURE
<222> LOCATION: (145)..(145)
<223> OTHER INFORMATION: Xaa at position 145 can be any naturally
      occurring amino acid, preferably Ala or Ser, more preferably Ala
<220> FEATURE:
<221> NAME/KEY: MISC_FEATURE
<222> LOCATION: (164)..(164)
<223> OTHER INFORMATION: Xaa at position 164 can be any naturally
      occurring amino acid, preferably Ala or Ser, more preferably Ser
<220> FEATURE:
<221> NAME/KEY: MISC_FEATURE
<222> LOCATION: (166)..(166)
<223> OTHER INFORMATION: Xaa at position 166 can be any naturally
      occurring amino acid, preferably Met or Leu, prerferably Leu
<220> FEATURE:
<221> NAME/KEY: MISC_FEATURE
<222> LOCATION: (178)..(178)
<223> OTHER INFORMATION: Xaa at position 178 can be any naturally
      occurring amino acid, preferably Asp or His, more preferably Asp
<220> FEATURE:
<221> NAME/KEY: MISC_FEATURE
<222> LOCATION: (181)..(181)
<223> OTHER INFORMATION: Xaa at position 181 is absent or any naturally
      occurring amino acid, preferably Asn
<220> FEATURE:
<221> NAME/KEY: MISC_FEATURE
<222> LOCATION: (182)..(182)
<223> OTHER INFORMATION: Xaa at position 182 is absent or any naturally
      occurring amino acid, preferably Glu
<220> FEATURE:
<221> NAME/KEY: MISC_FEATURE
<222> LOCATION: (183)..(183)
<223> OTHER INFORMATION: Xaa at position 183 is absent or any naturally
      occurring amino acid, preferably Ser

<400> SEQUENCE: 2
```

```
Met Thr Thr Ala Ser Xaa Ser Gln Val Arg Gln Asn Tyr Xaa Gln Xaa
1               5                   10                  15

Ser Glu Ala Ala Xaa Xaa Arg Gln Ile Asn Leu Glu Leu Xaa Ala Ser
            20                  25                  30

Tyr Val Tyr Leu Ser Met Ser Xaa Tyr Phe Asp Arg Asp Asp Val Ala
            35                  40                  45

Leu Lys Asn Phe Ala Lys Tyr Phe Leu His Gln Ser His Glu Glu Arg
50                  55                  60

Glu His Ala Glu Lys Leu Met Lys Leu Gln Asn Gln Arg Gly Gly Arg
65                  70                  75                  80

Ile Xaa Leu Xaa Asp Ile Lys Lys Pro Asp Xaa Asp Asp Trp Glu Ser
            85                  90                  95

Gly Leu Asn Ala Met Glu Cys Ala Leu Xaa Leu Glu Lys Xaa Val Asn
            100                 105                 110

Gln Ser Leu Leu Glu Leu His Lys Leu Ala Thr Asp Lys Asn Asp Pro
            115                 120                 125

His Leu Cys Asp Phe Ile Glu Thr Xaa Tyr Leu Xaa Glu Gln Val Lys
            130                 135                 140

Xaa Ile Lys Glu Leu Gly Asp His Val Thr Asn Leu Arg Lys Met Gly
145                 150                 155                 160

Ala Pro Glu Xaa Gly Xaa Ala Glu Tyr Leu Phe Asp Lys His Thr Leu
            165                 170                 175

Gly Xaa Ser Asp Xaa Xaa Xaa
            180

<210> SEQ ID NO 3
<211> LENGTH: 133
<212> TYPE: PRT
<213> ORGANISM: Mus musculus

<400> SEQUENCE: 3

Ala Glu Ala Ala Ile Asn Arg Gln Ile Asn Leu Glu Leu Tyr Ala Ser
1               5                   10                  15

Tyr Val Tyr Leu Ser Met Ser Cys Tyr Phe Asp Arg Asp Asp Val Ala
            20                  25                  30

Leu Lys Asn Phe Ala Lys Tyr Phe Leu His Gln Ser His Glu Glu Arg
            35                  40                  45

Glu His Ala Glu Lys Leu Met Lys Leu Gln Asn Gln Arg Gly Gly Arg
50                  55                  60

Ile Phe Leu Gln Asp Ile Lys Lys Pro Asp Arg Asp Asp Trp Glu Ser
65                  70                  75                  80

Gly Leu Asn Ala Met Glu Cys Ala Leu His Leu Glu Lys Ser Val Asn
            85                  90                  95

Gln Ser Leu Leu Glu Leu His Lys Leu Ala Thr Asp Lys Asn Asp Pro
            100                 105                 110

His Leu Cys Asp Phe Ile Glu Thr Tyr Tyr Leu Ser Glu Gln Val Lys
            115                 120                 125

Ser Ile Lys Glu Leu
    130

<210> SEQ ID NO 4
<211> LENGTH: 180
<212> TYPE: PRT
<213> ORGANISM: Mus musculus

<400> SEQUENCE: 4
```

Met Thr Thr Ala Ser Pro Ser Gln Val Arg Gln Asn Tyr His Gln Asp
1               5                   10                  15

Ala Glu Ala Ala Ile Asn Arg Gln Ile Asn Leu Glu Leu Tyr Ala Ser
            20                  25                  30

Tyr Val Tyr Leu Ser Met Ser Cys Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Arg Asp Asp Trp Glu Ser
                85                  90                  95

Gly Leu Asn Ala Met Glu Cys Ala Leu His Leu Glu Lys Ser Val Asn
                100                 105                 110

Gln Ser Leu Leu Glu Leu His Lys Leu Ala Thr Asp Lys Asn Asp Pro
            115                 120                 125

His Leu Cys Asp Phe Ile Glu Thr Tyr Tyr Leu Ser Glu Gln Val Lys
        130                 135                 140

Ser Ile Lys Glu Leu Gly Asp His Val Thr Asn Leu Arg Lys Met Gly
145                 150                 155                 160

Ala Pro Glu Ala Gly Met Ala Glu Tyr Leu Phe Asp Lys His Thr Leu
                165                 170                 175

Gly His Gly Asp
            180

<210> SEQ ID NO 5
<211> LENGTH: 132
<212> TYPE: PRT
<213> ORGANISM: Homo sapiens

<400> SEQUENCE: 5

Ser Glu Ala Ala Asn Arg Gln Ile Asn Leu Glu Leu Tyr Ala Ser Tyr
1               5                   10                  15

Val Tyr Leu Ser Met Ser Tyr Tyr Phe Asp Arg Asp Asp Val Ala Leu
            20                  25                  30

Lys Asn Phe Ala Lys Tyr Phe Leu His Gln Ser His Glu Glu Arg Glu
        35                  40                  45

His Ala Glu Lys Leu Met Lys Leu Gln Asn Gln Arg Gly Gly Arg Ile
    50                  55                  60

Phe Leu Gln Asp Ile Lys Lys Pro Asp Cys Asp Asp Trp Glu Ser Gly
65                  70                  75                  80

Leu Asn Ala Met Glu Cys Ala Leu His Leu Glu Lys Asn Val Asn Gln
                85                  90                  95

Ser Leu Leu Glu Leu His Lys Leu Ala Thr Asp Lys Asn Asp Pro His
            100                 105                 110

Leu Cys Asp Phe Ile Glu Thr His Tyr Leu Asn Glu Gln Val Lys Ala
        115                 120                 125

Ile Lys Glu Leu
    130

<210> SEQ ID NO 6
<211> LENGTH: 179
<212> TYPE: PRT
<213> ORGANISM: Homo sapiens

<400> SEQUENCE: 6

```
Met Thr Thr Ala Ser Thr Ser Gln Val Arg Gln Asn Tyr His Gln Asp
1               5                   10                  15

Ser Glu Ala Ala Asn Arg Gln Ile Asn Leu Glu Leu Tyr Ala Ser Tyr
                20                  25                  30

Val Tyr Leu Ser Met Ser Tyr Tyr Phe Asp Arg Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Lys Leu Gln Asn Gln Arg Gly Gly Arg Ile
65                  70                  75                  80

Phe Leu Gln Asp Ile Lys Lys Pro Asp Cys Asp Asp Trp Glu Ser Gly
                85                  90                  95

Leu Asn Ala Met Glu Cys Ala Leu His Leu Glu Lys Asn Val Asn Gln
                100                 105                 110

Ser Leu Leu Glu Leu His Lys Leu Ala Thr Asp Lys Asn Asp Pro His
            115                 120                 125

Leu Cys Asp Phe Ile Glu Thr His Tyr Leu Asn Glu Gln Val Lys Ala
    130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp
```

<210> SEQ ID NO 7
<211> LENGTH: 182
<212> TYPE: PRT
<213> ORGANISM: Artificial Sequence
<220> FEATURE:
<223> OTHER INFORMATION: Consensus sequence of mammalian ferritin H
      chains 2nd version
<220> FEATURE:
<221> NAME/KEY: MISC_FEATURE
<222> LOCATION: (6)..(6)
<223> OTHER INFORMATION: Xaa at position 6 can be any naturally
      occurring amino acid, preferably Pro
<220> FEATURE:
<221> NAME/KEY: MISC_FEATURE
<222> LOCATION: (14)..(14)
<223> OTHER INFORMATION: Xaa at position 14 can be any naturally
      occurring amino acid, preferably His
<220> FEATURE:
<221> NAME/KEY: MISC_FEATURE
<222> LOCATION: (16)..(16)
<223> OTHER INFORMATION: Xaa at position 16 can be any naturally
      occurring amino acid, preferably Asp
<220> FEATURE:
<221> NAME/KEY: MISC_FEATURE
<222> LOCATION: (21)..(21)
<223> OTHER INFORMATION: Xaa at position 21 may be present or absent, if
      present it means any naturally occurring amino acid, preferably
      Ile
<220> FEATURE:
<221> NAME/KEY: MISC_FEATURE
<222> LOCATION: (29)..(29)
<223> OTHER INFORMATION: Xaa at position 29 can be any naturally
      occurring amino acid, preferably Tyr
<220> FEATURE:
<221> NAME/KEY: MISC_FEATURE
<222> LOCATION: (81)..(81)
<223> OTHER INFORMATION: Xaa at position 81 can be any naturally
      occurring amino acid, preferably Phe
<220> FEATURE:
<221> NAME/KEY: MISC_FEATURE
<222> LOCATION: (83)..(83)
<223> OTHER INFORMATION: Xaa at position 83 can be any naturally

```
      occurring amino acid, preferably Gln
<220> FEATURE:
<221> NAME/KEY: MISC_FEATURE
<222> LOCATION: (105)..(105)
<223> OTHER INFORMATION: Xaa at position 105 can be any naturally
      occurring amino acid, preferably His
<220> FEATURE:
<221> NAME/KEY: MISC_FEATURE
<222> LOCATION: (144)..(144)
<223> OTHER INFORMATION: Xaa at position 144 can be any naturally
      occurring amino acid, preferably Ala or Ser, more preferably Ala
<220> FEATURE:
<221> NAME/KEY: MISC_FEATURE
<222> LOCATION: (180)..(180)
<223> OTHER INFORMATION: Xaa at position 180 is absent or any naturally
      occuring amino acid, preferably Asn
<220> FEATURE:
<221> NAME/KEY: MISC_FEATURE
<222> LOCATION: (181)..(181)
<223> OTHER INFORMATION: Xaa at position 181 is absent or any naturally
      occuring amino acid, preferably Glu
<220> FEATURE:
<221> NAME/KEY: MISC_FEATURE
<222> LOCATION: (182)..(182)
<223> OTHER INFORMATION: Xaa at position 182 is absent or any naturally
      occuring amino acid, preferably Ser

<400> SEQUENCE: 7

Met Thr Thr Ala Ser Xaa Ser Gln Val Arg Gln Asn Tyr Xaa Gln Xaa
1               5                   10                  15

Ser Glu Ala Ala Xaa Arg Gln Ile Asn Leu Glu Leu Xaa Ala Ser Tyr
            20                  25                  30

Val Tyr Leu Ser Met Ser Tyr Tyr Phe Asp Arg Asp Asp Val Ala Leu
        35                  40                  45

Lys Asn Phe Ala Lys Tyr Phe Leu His Gln Ser His Glu Glu Arg Glu
    50                  55                  60

His Ala Glu Lys Leu Met Lys Leu Gln Asn Gln Arg Gly Gly Arg Ile
65                  70                  75                  80

Xaa Leu Xaa Asp Ile Lys Lys Pro Asp Cys Asp Asp Trp Glu Ser Gly
                85                  90                  95

Leu Asn Ala Met Glu Cys Ala Leu Xaa Leu Glu Lys Asn Val Asn Gln
            100                 105                 110

Ser Leu Leu Glu Leu His Lys Leu Ala Thr Asp Lys Asn Asp Pro His
        115                 120                 125

Leu Cys Asp Phe Ile Glu Thr His Tyr Leu Asn Glu Gln Val Lys Xaa
    130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Xaa Xaa Xaa
            180

<210> SEQ ID NO 8
<211> LENGTH: 150
<212> TYPE: PRT
<213> ORGANISM: Artificial Sequence
<220> FEATURE:
<223> OTHER INFORMATION: Minimal consensus sequence of mammalian
      ferritin L chain
<220> FEATURE:
<221> NAME/KEY: MISC_FEATURE
<222> LOCATION: (5)..(5)
<223> OTHER INFORMATION: Xaa at position 5 can be any naturally
      occurring amino acid, preferably Asp or Glu, more preferably Asp
<220> FEATURE:
```

```
<221> NAME/KEY: MISC_FEATURE
<222> LOCATION: (12)..(12)
<223> OTHER INFORMATION: Xaa at position 12 can be any nnaturally
      occurring amino acid, preferably Arg or Ser, more preferably Ser
<220> FEATURE:
<221> NAME/KEY: MISC_FEATURE
<222> LOCATION: (17)..(17)
<223> OTHER INFORMATION: Xaa at position 17 can be any naturally
      occurring amino acid, preferably Ser or Arg, more preferably Ser
<220> FEATURE:
<221> NAME/KEY: MISC_FEATURE
<222> LOCATION: (19)..(19)
<223> OTHER INFORMATION: Xaa at position 19 can be any naturally
      occurring amino acid, preferably Arg or Gln, more preferably Gln
<220> FEATURE:
<221> NAME/KEY: MISC_FEATURE
<222> LOCATION: (29)..(29)
<223> OTHER INFORMATION: Xaa at position 29 can be any naturally
      occurring amino acid, preferably Phe
<220> FEATURE:
<221> NAME/KEY: MISC_FEATURE
<222> LOCATION: (30)..(30)
<223> OTHER INFORMATION: Xaa at position 30 can be any naturally
      occurring amino acid, preferably Tyr or Phe, more preferably Tyr
<220> FEATURE:
<221> NAME/KEY: MISC_FEATURE
<222> LOCATION: (42)..(42)
<223> OTHER INFORMATION: Xaa at position 42 can be any naturally
      occurring amino acid, preferably Ser or Gly, more preferably Ser
<220> FEATURE:
<221> NAME/KEY: MISC_FEATURE
<222> LOCATION: (56)..(56)
<223> OTHER INFORMATION: Xaa at position 56 can be any naturally
      occurirng amino acid, preferably Ala or Tyr, more preferably Tyr
<220> FEATURE:
<221> NAME/KEY: MISC_FEATURE
<222> LOCATION: (61)..(61)
<223> OTHER INFORMATION: Xaa at position 61 can be any naturally
      occurring amino acid, preferably Glu or Lys, more preferably Lys
<220> FEATURE:
<221> NAME/KEY: MISC_FEATURE
<222> LOCATION: (62)..(62)
<223> OTHER INFORMATION: Xaa at position 62 can be any naturally
      occurring amino acid, preferably Met or Phe, more preferably Met
<220> FEATURE:
<221> NAME/KEY: MISC_FEATURE
<222> LOCATION: (65)..(65)
<223> OTHER INFORMATION: Xaa at position 65 can be any naturally
      occurring amino acid, preferably Asp or Gln, more preferably Gln
<220> FEATURE:
<221> NAME/KEY: MISC_FEATURE
<222> LOCATION: (75)..(75)
<223> OTHER INFORMATION: Xaa at position 75 can be any naturally
      occurring amino acid, preferably Ile or Val, more preferably Ile
<220> FEATURE:
<221> NAME/KEY: MISC_FEATURE
<222> LOCATION: (76)..(76)
<223> OTHER INFORMATION: Xaa at position 76 can be any naturally
      occurring amino acid, preferably Lys or Gln, more preferably Lys
<220> FEATURE:
<221> NAME/KEY: MISC_FEATURE
<222> LOCATION: (79)..(79)
<223> OTHER INFORMATION: Xaa at position 79 can be any naturally
      occurring amino acid, preferably Ala or Ser, more preferably Ala
<220> FEATURE:
<221> NAME/KEY: MISC_FEATURE
<222> LOCATION: (80)..(80)
<223> OTHER INFORMATION: Xaa at position 80 can be any naturally
      occurring amino acid, preferably Glu or Gln, more preferably Gln
<220> FEATURE:
<221> NAME/KEY: MISC_FEATURE
<222> LOCATION: (87)..(87)
<223> OTHER INFORMATION: Xaa at position 87 can be any naturally
      occurring amino acid, preferably Pro or Gln, more preferably Pro
<220> FEATURE:
<221> NAME/KEY: MISC_FEATURE
<222> LOCATION: (88)..(88)
<223> OTHER INFORMATION: Xaa at position 88 can be any naturally
      occurring amino acid, preferably Glu or Asp, more preferably Asp
```

```
<220> FEATURE:
<221> NAME/KEY: MISC_FEATURE
<222> LOCATION: (91)..(91)
<223> OTHER INFORMATION: Xaa at position 91 can be any naturally
      occurring amino acid, preferably Glu or Lys, more preferably Lys
<220> FEATURE:
<221> NAME/KEY: MISC_FEATURE
<222> LOCATION: (94)..(94)
<223> OTHER INFORMATION: Xaa at position 94 can be any naturally
      occurring amino acid, preferably Met or Leu, more preferably Leu
<220> FEATURE:
<221> NAME/KEY: MISC_FEATURE
<222> LOCATION: (96)..(96)
<223> OTHER INFORMATION: Xaa at position 96 can be any naturally
      occurring amino acid, preferably Met or Leu, more preferably Met
<220> FEATURE:
<221> NAME/KEY: MISC_FEATURE
<222> LOCATION: (99)..(99)
<223> OTHER INFORMATION: Xaa at position 99 can be any naturally
      occurring amino acid, preferably Lys or Asn, preferably Lys
<220> FEATURE:
<221> NAME/KEY: MISC_FEATURE
<222> LOCATION: (115)..(115)
<223> OTHER INFORMATION: Xaa at position 115 can be any naturally
      occurring amino acid, preferably Thr or Ala, more preferably Thr
<220> FEATURE:
<221> NAME/KEY: MISC_FEATURE
<222> LOCATION: (119)..(119)
<223> OTHER INFORMATION: Xaa at position 119 can be any naturally
      occurring amino acid, preferably Leu
<220> FEATURE:
<221> NAME/KEY: MISC_FEATURE
<222> LOCATION: (125)..(125)
<223> OTHER INFORMATION: Xaa at position 125 can be any naturally
      occurring amino acid, preferably Ser or Thr, more preferably Thr
<220> FEATURE:
<221> NAME/KEY: MISC_FEATURE
<222> LOCATION: (127)..(127)
<223> OTHER INFORMATION: Xaa at position 127 can be any naturally
      occurring amino acid, preferably Tyr or Phe, more preferably Phe
<220> FEATURE:
<221> NAME/KEY: MISC_FEATURE
<222> LOCATION: (130)..(130)
<223> OTHER INFORMATION: Xaa at position 130 can be any naturally
      occurring amino acid, preferably Lys or Glu, more preferably Glu
<220> FEATURE:
<221> NAME/KEY: MISC_FEATURE
<222> LOCATION: (140)..(140)
<223> OTHER INFORMATION: Xaa at position 140 can be any naturally
      occurring amino acid, preferably Asp or Asn, more preferably Asp
<220> FEATURE:
<221> NAME/KEY: MISC_FEATURE
<222> LOCATION: (146)..(146)
<223> OTHER INFORMATION: Xaa at position 146 can be any naturally
      occurring amino acid, preferably Arg or His, more preferably His
<220> FEATURE:
<221> NAME/KEY: MISC_FEATURE
<222> LOCATION: (148)..(148)
<223> OTHER INFORMATION: Xaa at position 148 can be any naturally
      occurring amino acid, preferably Leu or Val, more preferably Leu

<400> SEQUENCE: 8

Asn Tyr Ser Thr Xaa Val Glu Ala Ala Val Asn Xaa Leu Val Asn Leu
1               5                   10                  15

Xaa Leu Xaa Ala Ser Tyr Thr Tyr Leu Ser Leu Gly Xaa Xaa Phe Asp
            20                  25                  30

Arg Asp Asp Val Ala Leu Glu Gly Val Xaa His Phe Phe Arg Glu Leu
        35                  40                  45

Ala Glu Glu Lys Arg Glu Gly Xaa Glu Arg Leu Leu Xaa Xaa Gln Asn
    50                  55                  60

Xaa Arg Gly Gly Arg Ala Leu Phe Gln Asp Xaa Xaa Lys Pro Xaa Xaa
65                  70                  75                  80

Asp Glu Trp Gly Lys Thr Xaa Xaa Ala Met Xaa Ala Ala Xaa Ala Xaa
```

85                  90                  95

Glu Lys Xaa Leu Asn Gln Ala Leu Leu Asp Leu His Ala Leu Gly Ser
            100                 105                 110

Ala Arg Xaa Asp Pro His Xaa Cys Asp Phe Leu Glu Xaa His Xaa Leu
        115                 120                 125

Asp Xaa Glu Val Lys Leu Ile Lys Lys Met Gly Xaa His Leu Thr Asn
    130                 135                 140

Leu Xaa Arg Xaa Ala Gly
145                 150

<210> SEQ ID NO 9
<211> LENGTH: 183
<212> TYPE: PRT
<213> ORGANISM: Artificial Sequence
<220> FEATURE:
<223> OTHER INFORMATION: Consensus sequence of mammalian ferritin L
      chain
<220> FEATURE:
<221> NAME/KEY: MISC_FEATURE
<222> LOCATION: (12)..(12)
<223> OTHER INFORMATION: Xaa at position 12 can be any naturally
      occurring amino acid, preferably Asp or Glu, more preferably Asp
<220> FEATURE:
<221> NAME/KEY: MISC_FEATURE
<222> LOCATION: (19)..(19)
<223> OTHER INFORMATION: Xaa at position 19 can be any naturally
      occurring amino acid, preferably Ser or Arg, more preferably Ser
<220> FEATURE:
<221> NAME/KEY: MISC_FEATURE
<222> LOCATION: (24)..(24)
<223> OTHER INFORMATION: Xaa at position 24 can be any naturally
      occurring amino acid, preferably Ser or Arg, more preferably Ser
<220> FEATURE:
<221> NAME/KEY: MISC_FEATURE
<222> LOCATION: (26)..(26)
<223> OTHER INFORMATION: Xaa at position 26 can be any naturally
      occurring amino acid, preferably Arg or Gln, more preferably Gln
<220> FEATURE:
<221> NAME/KEY: MISC_FEATURE
<222> LOCATION: (36)..(36)
<223> OTHER INFORMATION: Xaa at position 36 can be any naturally
      occurring amino acid, preferably Phe
<220> FEATURE:
<221> NAME/KEY: MISC_FEATURE
<222> LOCATION: (37)..(37)
<223> OTHER INFORMATION: Xaa at position 37 can be any naturally
      occurring amino acid, preferably Tyr or Phe, more preferably Tyr
<220> FEATURE:
<221> NAME/KEY: MISC_FEATURE
<222> LOCATION: (49)..(49)
<223> OTHER INFORMATION: Xaa at position 47 can be any naturally
      occurring amino acid, preferably Ser or Gly, more preferably Ser
<220> FEATURE:
<221> NAME/KEY: MISC_FEATURE
<222> LOCATION: (63)..(63)
<223> OTHER INFORMATION: Xaa at position 63 can be any naturally
      occurring amino acid, preferably Ala or Tyr, more preferably Tyr
<220> FEATURE:
<221> NAME/KEY: MISC_FEATURE
<222> LOCATION: (68)..(68)
<223> OTHER INFORMATION: Xaa at position 68 can be any naturally
      occurring amino acid, preferably Glu or Lys, more preferably Lys
<220> FEATURE:
<221> NAME/KEY: MISC_FEATURE
<222> LOCATION: (69)..(69)
<223> OTHER INFORMATION: Xaa at position 69 can be any naturally
      occurring amino acid, preferably Met or Phe, more preferably Met
<220> FEATURE:
<221> NAME/KEY: MISC_FEATURE
<222> LOCATION: (72)..(72)
<223> OTHER INFORMATION: Xaa at position 72 can be any naturally
      occurring amino acid, preferably Asp or Gln, more preferably Gln
<220> FEATURE:
<221> NAME/KEY: MISC_FEATURE

```
<222> LOCATION: (82)..(82)
<223> OTHER INFORMATION: Xaa at position 82 can be any naturally
      occurring amino acid, preferably Ile or Val, more preferably Ile
<220> FEATURE:
<221> NAME/KEY: MISC_FEATURE
<222> LOCATION: (83)..(83)
<223> OTHER INFORMATION: Xaa at position 83 can be any naturally
      occurring amino acid, preferably Lys or Gln, more preferably Lys
<220> FEATURE:
<221> NAME/KEY: MISC_FEATURE
<222> LOCATION: (86)..(86)
<223> OTHER INFORMATION: Xaa at position 86 can be any naturally
      occurring amino acid, preferably Ala or Ser, more preferably Ala
<220> FEATURE:
<221> NAME/KEY: MISC_FEATURE
<222> LOCATION: (87)..(87)
<223> OTHER INFORMATION: Xaa at position 87 can be any naturally
      occurring amino acid, preferably Glu or Gln, more preferably Gln
<220> FEATURE:
<221> NAME/KEY: MISC_FEATURE
<222> LOCATION: (94)..(94)
<223> OTHER INFORMATION: Xaa at position 94 can be any naturally
      occurring amino acid, preferably Pro or Gln, more preferably Pro
<220> FEATURE:
<221> NAME/KEY: MISC_FEATURE
<222> LOCATION: (95)..(95)
<223> OTHER INFORMATION: Xaa at position 95 can be any naturally
      occurring amino acid, preferably Glu or Asp, more preferably Asp
<220> FEATURE:
<221> NAME/KEY: MISC_FEATURE
<222> LOCATION: (98)..(98)
<223> OTHER INFORMATION: Xaa at position 98 can be any naturally
      occurring amino acid, preferably Glu or Lys, more preferably Lys
<220> FEATURE:
<221> NAME/KEY: MISC_FEATURE
<222> LOCATION: (101)..(101)
<223> OTHER INFORMATION: Xaa at position 101 can be any naturally
      occurring amino acid, preferably Met or Leu, more preferably Leu
<220> FEATURE:
<221> NAME/KEY: MISC_FEATURE
<222> LOCATION: (103)..(103)
<223> OTHER INFORMATION: Xaa at position 103 can be any naturally
      occurring amino acid, preferably Met or Leu, more preferably Met
<220> FEATURE:
<221> NAME/KEY: MISC_FEATURE
<222> LOCATION: (106)..(106)
<223> OTHER INFORMATION: Xaa at position 106 can be any naturally
      occurring amino acid, preferably Lys or Asn, preferably Lys
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: MISC_FEATURE
<222> LOCATION: (126)..(126)
<223> OTHER INFORMATION: Xaa at position 126 can be any naturally
      occurring  amino acid, preferably Leu
<220> FEATURE:
<221> NAME/KEY: MISC_FEATURE
<222> LOCATION: (132)..(132)
<223> OTHER INFORMATION: Xaa at position 132 can be any naturally
      occurring amino acid, preferably Ser or Thr, more preferably Thr
<220> FEATURE:
<221> NAME/KEY: MISC_FEATURE
<222> LOCATION: (134)..(134)
<223> OTHER INFORMATION: Xaa at position 134 can be any naturally
      occurring amino acid, preferably Tyr or Phe, more preferably Phe
<220> FEATURE:
<221> NAME/KEY: MISC_FEATURE
<222> LOCATION: (137)..(137)
<223> OTHER INFORMATION: Xaa at position 137 can be any naturally
      occurring amino acid, preferably Lys or Glu, more preferably Glu
<220> FEATURE:
<221> NAME/KEY: MISC_FEATURE
<222> LOCATION: (147)..(147)
<223> OTHER INFORMATION: Xaa at position 147 can be any naturally
      occurring amino acid, preferably Asp or Asn, more preferably Asp
<220> FEATURE:
<221> NAME/KEY: MISC_FEATURE
```

```
<222> LOCATION: (153)..(153)
<223> OTHER INFORMATION: Xaa at position 153 can be any naturally
      occurring amino acid, preferably Arg or His, more preferably His
<220> FEATURE:
<221> NAME/KEY: MISC_FEATURE
<222> LOCATION: (155)..(155)
<223> OTHER INFORMATION: Xaa at position 155 can be any naturally
      occurring  amino acid, preferably Leu or Val, more preferably Leu
<220> FEATURE:
<221> NAME/KEY: MISC_FEATURE
<222> LOCATION: (161)..(161)
<223> OTHER INFORMATION: Xaa at position 161 can be absent or any
      naturally occurring amino acid, preferably Ala
<220> FEATURE:
<221> NAME/KEY: MISC_FEATURE
<222> LOCATION: (163)..(163)
<223> OTHER INFORMATION: Xaa at position 163 can be absent or any
      naturally occurring amino acid, preferably Thr
<220> FEATURE:
<221> NAME/KEY: MISC_FEATURE
<222> LOCATION: (166)..(166)
<223> OTHER INFORMATION: Xaa at position 166 can be absent or any
      naturally occurring amino acid, preferably Pro
<220> FEATURE:
<221> NAME/KEY: MISC_FEATURE
<222> LOCATION: (168)..(168)
<223> OTHER INFORMATION: Xaa at position 168 can be any naturally
      occurring amino acid, preferably Gly or Ala, more preferably Ala

<400> SEQUENCE: 9

Met Thr Ser Gln Ile Arg Gln Asn Tyr Ser Thr Xaa Val Glu Ala Ala
1               5                   10                  15

Val Asn Xaa Leu Val Asn Leu Xaa Leu Xaa Ala Ser Tyr Thr Tyr Leu
            20                  25                  30

Ser Leu Gly Xaa Xaa Phe Asp Arg Asp Asp Val Ala Leu Glu Gly Val
        35                  40                  45

Xaa His Phe Phe Arg Glu Leu Ala Glu Glu Lys Arg Glu Gly Xaa Glu
    50                  55                  60

Arg Leu Leu Xaa Xaa Gln Asn Xaa Arg Gly Gly Arg Ala Leu Phe Gln
65                  70                  75                  80

Asp Xaa Xaa Lys Pro Xaa Asp Glu Trp Gly Lys Thr Xaa Xaa Ala
                85                  90                  95

Met Xaa Ala Ala Xaa Ala Xaa Glu Lys Xaa Leu Asn Gln Ala Leu Leu
            100                 105                 110

Asp Leu His Ala Leu Gly Ser Ala Arg Xaa Asp Pro His Xaa Cys Asp
            115                 120                 125

Phe Leu Glu Xaa His Xaa Leu Asp Xaa Glu Val Lys Leu Ile Lys Lys
        130                 135                 140

Met Gly Xaa His Leu Thr Asn Leu Xaa Arg Xaa Ala Gly Pro Gln Pro
145                 150                 155                 160

Xaa Gln Xaa Gly Val Xaa Gln Xaa Ser Leu Gly Glu Tyr Leu Phe Glu
                165                 170                 175

Arg Leu Thr Leu Lys His Asp
            180

<210> SEQ ID NO 10
<211> LENGTH: 150
<212> TYPE: PRT
<213> ORGANISM: Mus musculus
<220> FEATURE:
<221> NAME/KEY: MISC_FEATURE
<222> LOCATION: (12)..(12)
<223> OTHER INFORMATION: Xaa at position 5 can be any naturally occuring
      amino acid, preferably Asp or Glu, more preferably Asp

<400> SEQUENCE: 10
```

-continued

```
Asn Tyr Ser Thr Glu Val Ala Ala Val Asn Arg Leu Val Asn Leu
1               5                   10                  15

His Leu Arg Ala Ser Tyr Thr Tyr Leu Ser Leu Gly Phe Phe Phe Asp
                20                  25                  30

Arg Asp Asp Val Ala Leu Glu Gly Val Gly His Phe Phe Arg Glu Leu
                35                  40                  45

Ala Glu Glu Lys Arg Glu Gly Ala Glu Arg Leu Leu Glu Phe Gln Asn
            50                  55                  60

Asp Arg Gly Gly Arg Ala Leu Phe Gln Asp Val Gln Lys Pro Ser Gln
65                      70                  75                  80

Asp Glu Trp Gly Lys Thr Gln Glu Ala Met Glu Ala Ala Leu Ala Met
                    85                  90                  95

Glu Lys Asn Leu Asn Gln Ala Leu Leu Asp Leu His Ala Leu Gly Ser
                100                 105                 110

Ala Arg Ala Asp Pro His Leu Cys Asp Phe Leu Glu Ser His Tyr Leu
                115                 120                 125

Asp Lys Glu Val Lys Leu Ile Lys Lys Met Gly Asn His Leu Thr Asn
            130                 135                 140

Leu Arg Arg Val Ala Gly
145                 150
```

<210> SEQ ID NO 11

<400> SEQUENCE: 11

000

<210> SEQ ID NO 12
<211> LENGTH: 149
<212> TYPE: PRT
<213> ORGANISM: Homo sapiens

<400> SEQUENCE: 12

```
Asn Tyr Ser Thr Asp Val Glu Ala Ala Val Asn Ser Leu Val Asn Leu
1               5                   10                  15

Tyr Leu Gln Ala Ser Tyr Thr Tyr Leu Ser Leu Gly Phe Tyr Phe Asp
                20                  25                  30

Arg Asp Asp Val Ala Leu Glu Gly Val Ser His Phe Phe Arg Glu Leu
                35                  40                  45

Ala Glu Glu Lys Arg Glu Gly Tyr Glu Arg Leu Leu Lys Met Gln Asn
            50                  55                  60

Gln Arg Gly Gly Arg Ala Leu Phe Gln Asp Ile Lys Lys Pro Ala Glu
65                      70                  75                  80

Asp Glu Trp Gly Lys Thr Pro Asp Ala Met Lys Ala Ala Met Ala Leu
                    85                  90                  95

Glu Lys Lys Leu Asn Gln Ala Leu Leu Asp Leu His Ala Leu Gly Ser
                100                 105                 110

Ala Arg Thr Asp Pro His Leu Cys Asp Phe Leu Glu Thr His Phe Leu
                115                 120                 125

Asp Glu Glu Val Lys Leu Ile Lys Lys Met Gly Asp His Leu Thr Asn
            130                 135                 140

Leu His Arg Leu Gly
145
```

<210> SEQ ID NO 13
<211> LENGTH: 175

<212> TYPE: PRT
<213> ORGANISM: Homo sapiens

<400> SEQUENCE: 13

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 14
<211> LENGTH: 183
<212> TYPE: PRT
<213> ORGANISM: Artificial Sequence
<220> FEATURE:
<223> OTHER INFORMATION: Consensus seqeuence of mammaliam ferritin L
      chain 2nd version
<220> FEATURE:
<221> NAME/KEY: MISC_FEATURE
<222> LOCATION: (36)..(36)
<223> OTHER INFORMATION: Xaa at position 36 can be any naturally
      occuring amino acid, preferably Phe
<220> FEATURE:
<221> NAME/KEY: MISC_FEATURE
<222> LOCATION: (37)..(37)
<223> OTHER INFORMATION: Xaa at position 37 can be any naturally
      occuring amino acid, preferably Tyr or Phe, more preferably Tyr
<220> FEATURE:
<221> NAME/KEY: MISC_FEATURE
<222> LOCATION: (94)..(94)
<223> OTHER INFORMATION: Xaa at position 94 can be any naturally
      occurring  amino acid, preferably Pro or Gln, more preferably Pro
<220> FEATURE:
<221> NAME/KEY: MISC_FEATURE
<222> LOCATION: (126)..(126)
<223> OTHER INFORMATION: Xaa at position 126 can be any naturally
      occurring  amino acid, preferably Leu
<220> FEATURE:
<221> NAME/KEY: MISC_FEATURE
<222> LOCATION: (137)..(137)
<223> OTHER INFORMATION: Xaa at position 137 can be any naturally
      occurring  amino acid, preferably Lys or Glu, more preferably Glu
<220> FEATURE:
<221> NAME/KEY: MISC_FEATURE
<222> LOCATION: (147)..(147)
<223> OTHER INFORMATION: Xaa at position 147 can be any naturally
      occurring  amino acid, preferably Asp or Asn, more preferably Asp
<220> FEATURE:
<221> NAME/KEY: misc_feature
<222> LOCATION: (161)..(161)

```
<223> OTHER INFORMATION: Xaa can be any naturally occurring amino acid
<220> FEATURE:
<221> NAME/KEY: MISC_FEATURE
<222> LOCATION: (163)..(163)
<223> OTHER INFORMATION: Xaa at position 163 can be absent or any
      naturally occurring amino acid, preferably Thr
<220> FEATURE:
<221> NAME/KEY: MISC_FEATURE
<222> LOCATION: (166)..(166)
<223> OTHER INFORMATION: Xaa at position 166 can be absent or any
      naturally occurring amino acid, preferably Pro
<220> FEATURE:
<221> NAME/KEY: MISC_FEATURE
<222> LOCATION: (168)..(168)
<223> OTHER INFORMATION: Xaa at position 168 can be any naturally
      occurring  amino acid, preferably Gly or Ala, more preferably Ala

<400> SEQUENCE: 14

Met Thr Ser Gln Ile Arg Gln Asn Tyr Ser Thr Glu Val Glu Ala Ala
1               5                   10                  15

Val Asn Arg Leu Val Asn Leu His Leu Arg Ala Ser Tyr Thr Tyr Leu
            20                  25                  30

Ser Leu Gly Xaa Xaa Phe Asp Arg Asp Asp Val Ala Leu Glu Gly Val
        35                  40                  45

Gly His Phe Phe Arg Glu Leu Ala Glu Glu Lys Arg Glu Gly Ala Glu
    50                  55                  60

Arg Leu Leu Lys Leu Gln Asn Gln Arg Gly Gly Arg Ala Leu Phe Gln
65                  70                  75                  80

Asp Val Gln Lys Pro Ala Gln Asp Glu Trp Gly Lys Thr Xaa Glu Ala
                85                  90                  95

Met Glu Ala Ala Leu Ala Leu Glu Lys Asn Leu Asn Gln Ala Leu Leu
            100                 105                 110

Asp Leu His Ala Leu Gly Ser Ala Arg Thr Asp Pro His Xaa Cys Asp
        115                 120                 125

Phe Leu Glu Asn His Phe Leu Asp Xaa Glu Val Lys Leu Ile Lys Lys
    130                 135                 140

Met Gly Xaa His Leu Thr Asn Leu Arg Arg Leu Ala Gly Pro Gln Pro
145                 150                 155                 160

Xaa Gln Xaa Gly Val Xaa Gln Xaa Ser Leu Gly Glu Tyr Leu Phe Glu
                165                 170                 175

Arg Leu Thr Leu Lys His Asp
            180

<210> SEQ ID NO 15
<211> LENGTH: 117
<212> TYPE: PRT
<213> ORGANISM: Artificial Sequence
<220> FEATURE:
<223> OTHER INFORMATION: Minimal consensus sequence of mammalian
      haemoglobin alpha chain
<220> FEATURE:
<221> NAME/KEY: MISC_FEATURE
<222> LOCATION: (5)..(5)
<223> OTHER INFORMATION: Xaa can be any naturally occurring amino acid,
      preferably Ala
<220> FEATURE:
<221> NAME/KEY: MISC_FEATURE
<222> LOCATION: (9)..(9)
<223> OTHER INFORMATION: Xaa can be any naturally occurring amino acid,
      preferably Gly
<220> FEATURE:
<221> NAME/KEY: MISC_FEATURE
<222> LOCATION: (15)..(15)
<223> OTHER INFORMATION: Xaa can be any naturally occurring amino acid,
      preferably Arg
<220> FEATURE:
```

```
<221> NAME/KEY: MISC_FEATURE
<222> LOCATION: (21)..(21)
<223> OTHER INFORMATION: Xaa can be any naturally occurring amino acid,
      preferably Pro
<220> FEATURE:
<221> NAME/KEY: MISC_FEATURE
<222> LOCATION: (22)..(22)
<223> OTHER INFORMATION: Xaa can be any naturally occurring amino acid,
      preferably Thr
<220> FEATURE:
<221> NAME/KEY: MISC_FEATURE
<222> LOCATION: (38)..(38)
<223> OTHER INFORMATION: Xaa can be any naturally occurring amino acid,
      preferably Gln
<220> FEATURE:
<221> NAME/KEY: MISC_FEATURE
<222> LOCATION: (41)..(41)
<223> OTHER INFORMATION: Xaa can be any naturally occurring amino acid,
      preferably Gly
<220> FEATURE:
<221> NAME/KEY: MISC_FEATURE
<222> LOCATION: (48)..(48)
<223> OTHER INFORMATION: Xaa can be any naturally occurring amino acid,
      preferably Asp
<220> FEATURE:
<221> NAME/KEY: MISC_FEATURE
<222> LOCATION: (49)..(49)
<223> OTHER INFORMATION: Xaa can be any naturally occurring amino acid,
      preferably Ala
<220> FEATURE:
<221> NAME/KEY: MISC_FEATURE
<222> LOCATION: (55)..(55)
<223> OTHER INFORMATION: Xaa can be any naturally occurring amino acid,
      preferably Ala
<220> FEATURE:
<221> NAME/KEY: MISC_FEATURE
<222> LOCATION: (59)..(59)
<223> OTHER INFORMATION: Xaa can be any naturally occurring amino acid,
      preferably Aap
<220> FEATURE:
<221> NAME/KEY: MISC_FEATURE
<222> LOCATION: (60)..(60)
<223> OTHER INFORMATION: Xaa can be any naturally occurring amino acid,
      preferably Met
<220> FEATURE:
<221> NAME/KEY: MISC_FEATURE
<222> LOCATION: (68)..(68)
<223> OTHER INFORMATION: Xaa can be any naturally occurring amino acid,
      preferably Ser
<220> FEATURE:
<221> NAME/KEY: MISC_FEATURE
<222> LOCATION: (76)..(76)
<223> OTHER INFORMATION: Xaa can be any naturally occurring amino acid,
      preferably Arg
<220> FEATURE:
<221> NAME/KEY: MISC_FEATURE
<222> LOCATION: (79)..(79)
<223> OTHER INFORMATION: Xaa can be any naturally occurring amino acid,
      preferably Pro
<220> FEATURE:
<221> NAME/KEY: MISC_FEATURE
<222> LOCATION: (90)..(90)
<223> OTHER INFORMATION: Xaa can be any naturally occurring amino acid,
      preferably Leu
<220> FEATURE:
<221> NAME/KEY: MISC_FEATURE
<222> LOCATION: (91)..(91)
<223> OTHER INFORMATION: Xaa can be any naturally occurring amino acid,
      preferably Val
<220> FEATURE:
<221> NAME/KEY: MISC_FEATURE
<222> LOCATION: (94)..(94)
<223> OTHER INFORMATION: Xaa can be any naturally occurring amino acid,
      preferably Ala
<220> FEATURE:
<221> NAME/KEY: MISC_FEATURE
<222> LOCATION: (102)..(102)
<223> OTHER INFORMATION: Xaa can be any naturally occurring amino acid,
      preferably Thr
```

```
<220> FEATURE:
<221> NAME/KEY: MISC_FEATURE
<222> LOCATION: (108)..(108)
<223> OTHER INFORMATION: Xaa can be any naturally occurring amino acid,
      preferably Ser
<220> FEATURE:
<221> NAME/KEY: MISC_FEATURE
<222> LOCATION: (117)..(117)
<223> OTHER INFORMATION: Xaa can be any naturally occurring amino acid,
      preferably Ser

<400> SEQUENCE: 15

Val Gly Ala His Xaa Gly Glu Tyr Xaa Ala Glu Ala Leu Glu Xaa Met
1               5                   10                  15

Phe Leu Ser Phe Xaa Xaa Thr Lys Thr Tyr Phe Pro His Phe Asp Leu
            20                  25                  30

Ser His Gly Ser Ala Xaa Val Lys Xaa His Gly Lys Lys Val Ala Xaa
        35                  40                  45

Xaa Leu Thr Asn Ala Val Xaa His Val Asp Xaa Xaa Pro Asn Ala Leu
50                  55                  60

Ser Ala Leu Xaa Asp Leu His Ala His Lys Leu Xaa Val Asp Xaa Val
65                  70                  75                  80

Asn Phe Lys Leu Leu Ser His Cys Leu Xaa Xaa Thr Leu Xaa Ala His
                85                  90                  95

Leu Pro Ala Glu Phe Xaa Pro Ala Val His Ala Xaa Leu Asp Lys Phe
            100                 105                 110

Leu Ala Ser Val Xaa
            115

<210> SEQ ID NO 16
<211> LENGTH: 142
<212> TYPE: PRT
<213> ORGANISM: Artificial Sequence
<220> FEATURE:
<223> OTHER INFORMATION: Consensus sequence of mammalian alpha chain
      haemoglobins
<220> FEATURE:
<221> NAME/KEY: MISC_FEATURE
<222> LOCATION: (1)..(1)
<223> OTHER INFORMATION: Xaa can be any naturally occurring amino acid,
      preferably Met
<220> FEATURE:
<221> NAME/KEY: MISC_FEATURE
<222> LOCATION: (2)..(2)
<223> OTHER INFORMATION: Xaa can be any naturally occurring amino acid,
      preferably Val
<220> FEATURE:
<221> NAME/KEY: MISC_FEATURE
<222> LOCATION: (14)..(14)
<223> OTHER INFORMATION: Xaa can be any naturally occurring amino acid,
      preferably Ala
<220> FEATURE:
<221> NAME/KEY: MISC_FEATURE
<222> LOCATION: (17)..(17)
<223> OTHER INFORMATION: Xaa can be any naturally occurring amino acid,
      preferably Lys
<220> FEATURE:
<221> NAME/KEY: MISC_FEATURE
<222> LOCATION: (22)..(22)
<223> OTHER INFORMATION: Xaa can be any naturally occurring amino acid,
      preferably Ala
<220> FEATURE:
<221> NAME/KEY: MISC_FEATURE
<222> LOCATION: (26)..(26)
<223> OTHER INFORMATION: Xaa can be any naturally occurring amino acid,
      preferably Gly
<220> FEATURE:
<221> NAME/KEY: MISC_FEATURE
<222> LOCATION: (32)..(32)
<223> OTHER INFORMATION: Xaa can be any naturally occurring amino acid,
``` preferably Arg
<220> FEATURE:
<221> NAME/KEY: MISC_FEATURE
<222> LOCATION: (38)..(38)
<223> OTHER INFORMATION: Xaa can be any naturally occurring amino acid,
      preferably Pro
<220> FEATURE:
<221> NAME/KEY: MISC_FEATURE
<222> LOCATION: (39)..(39)
<223> OTHER INFORMATION: Xaa can be any naturally occurring amino acid,
      preferably Thr
<220> FEATURE:
<221> NAME/KEY: MISC_FEATURE
<222> LOCATION: (55)..(55)
<223> OTHER INFORMATION: Xaa can be any naturally occurring amino acid,
      preferably Gln
<220> FEATURE:
<221> NAME/KEY: MISC_FEATURE
<222> LOCATION: (58)..(58)
<223> OTHER INFORMATION: Xaa can be any naturally occurring amino acid,
      preferably Gly
<220> FEATURE:
<221> NAME/KEY: MISC_FEATURE
<222> LOCATION: (65)..(65)
<223> OTHER INFORMATION: Xaa can be any naturally occurring amino acid,
      preferably Asp
<220> FEATURE:
<221> NAME/KEY: MISC_FEATURE
<222> LOCATION: (66)..(66)
<223> OTHER INFORMATION: Xaa can be any naturally occurring amino acid,
      preferably Ala
<220> FEATURE:
<221> NAME/KEY: MISC_FEATURE
<222> LOCATION: (72)..(72)
<223> OTHER INFORMATION: Xaa can be any naturally occurring amino acid,
      preferably Ala
<220> FEATURE:
<221> NAME/KEY: MISC_FEATURE
<222> LOCATION: (76)..(76)
<223> OTHER INFORMATION: Xaa can be any naturally occurring amino acid,
      preferably Asp
<220> FEATURE:
<221> NAME/KEY: MISC_FEATURE
<222> LOCATION: (77)..(77)
<223> OTHER INFORMATION: Xaa can be any naturally occurring amino acid,
      preferably Met
<220> FEATURE:
<221> NAME/KEY: MISC_FEATURE
<222> LOCATION: (85)..(85)
<223> OTHER INFORMATION: Xaa can be any naturally occurring amino acid,
      preferably Ser
<220> FEATURE:
<221> NAME/KEY: MISC_FEATURE
<222> LOCATION: (93)..(93)
<223> OTHER INFORMATION: Xaa can be any naturally occurring amino acid,
      preferably Arg
<220> FEATURE:
<221> NAME/KEY: MISC_FEATURE
<222> LOCATION: (96)..(96)
<223> OTHER INFORMATION: Xaa can be any naturally occurring amino acid,
      preferably Pro
<220> FEATURE:
<221> NAME/KEY: MISC_FEATURE
<222> LOCATION: (107)..(107)
<223> OTHER INFORMATION: Xaa can be any naturally occurring amino acid,
      preferably Leu
<220> FEATURE:
<221> NAME/KEY: MISC_FEATURE
<222> LOCATION: (108)..(108)
<223> OTHER INFORMATION: Xaa can be any naturally occurring amino acid,
      preferably Val
<220> FEATURE:
<221> NAME/KEY: MISC_FEATURE
<222> LOCATION: (111)..(111)
<223> OTHER INFORMATION: Xaa can be any naturally occurring amino acid,
      preferably Ala
<220> FEATURE:
<221> NAME/KEY: MISC_FEATURE
<222> LOCATION: (119)..(119)

<223> OTHER INFORMATION: Xaa can be any naturally occurring amino acid,
      preferably Thr
<220> FEATURE:
<221> NAME/KEY: MISC_FEATURE
<222> LOCATION: (125)..(125)
<223> OTHER INFORMATION: Xaa can be any naturally occurring amino acid,
      preferably Ser
<220> FEATURE:
<221> NAME/KEY: MISC_FEATURE
<222> LOCATION: (134)..(134)
<223> OTHER INFORMATION: Xaa can be any naturally occurring amino acid,
      preferably Ser
<220> FEATURE:
<221> NAME/KEY: MISC_FEATURE
<222> LOCATION: (142)..(142)
<223> OTHER INFORMATION: Xaa can be any naturally occurring amino acid,
      preferably Arg

<400> SEQUENCE: 16

Xaa Xaa Leu Ser Pro Ala Asp Lys Thr Asn Val Lys Ala Xaa Trp Gly
 1               5                  10                  15

Xaa Val Gly Ala His Xaa Gly Glu Tyr Xaa Ala Glu Ala Leu Glu Xaa
                20                  25                  30

Met Phe Leu Ser Phe Xaa Xaa Thr Lys Thr Tyr Phe Pro His Phe Asp
            35                  40                  45

Leu Ser His Gly Ser Ala Xaa Val Lys Xaa His Gly Lys Lys Val Ala
    50                  55                  60

Xaa Xaa Leu Thr Asn Ala Val Xaa His Val Asp Xaa Xaa Pro Asn Ala
65                  70                  75                  80

Leu Ser Ala Leu Xaa Asp Leu His Ala His Lys Leu Xaa Val Asp Xaa
                85                  90                  95

Val Asn Phe Lys Leu Leu Ser His Cys Leu Xaa Xaa Thr Leu Xaa Ala
            100                 105                 110

His Leu Pro Ala Glu Phe Xaa Pro Ala Val His Ala Xaa Leu Asp Lys
        115                 120                 125

Phe Leu Ala Ser Val Xaa Thr Val Leu Thr Ser Lys Tyr Xaa
    130                 135                 140

<210> SEQ ID NO 17
<211> LENGTH: 117
<212> TYPE: PRT
<213> ORGANISM: Homo sapiens

<400> SEQUENCE: 17

Val Gly Ala His Ala Gly Glu Tyr Gly Ala Glu Ala Leu Glu Arg Met
 1               5                  10                  15

Phe Leu Ser Phe Pro Thr Thr Lys Thr Tyr Phe Pro His Phe Asp Leu
                20                  25                  30

Ser His Gly Ser Ala Gln Val Lys Gly His Gly Lys Lys Val Ala Asp
            35                  40                  45

Ala Leu Thr Asn Ala Val Ala His Val Asp Asp Met Pro Asn Ala Leu
    50                  55                  60

Ser Ala Leu Ser Asp Leu His Ala His Lys Leu Arg Val Asp Pro Val
65                  70                  75                  80

Asn Phe Lys Leu Leu Ser His Cys Leu Leu Val Thr Leu Ala Ala His
                85                  90                  95

Leu Pro Ala Glu Phe Thr Pro Ala Val His Ala Ser Leu Asp Lys Phe
            100                 105                 110

Leu Ala Ser Val Ser
        115

<210> SEQ ID NO 18
<211> LENGTH: 142
<212> TYPE: PRT
<213> ORGANISM: Homo sapiens

<400> SEQUENCE: 18

```
Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Lys Lys Val Ala
    50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140
```

<210> SEQ ID NO 19
<211> LENGTH: 124
<212> TYPE: PRT
<213> ORGANISM: Artificial Sequence
<220> FEATURE:
<223> OTHER INFORMATION: Minimal consensus sequence of mammalian
      haemoglobin beta chain
<220> FEATURE:
<221> NAME/KEY: MISC_FEATURE
<222> LOCATION: (4)..(4)
<223> OTHER INFORMATION: Xaa can be any naturally occurring amino acid,
      preferably Asn
<220> FEATURE:
<221> NAME/KEY: MISC_FEATURE
<222> LOCATION: (9)..(9)
<223> OTHER INFORMATION: Xaa can be any naturally occurring amino acid,
      preferably Gly
<220> FEATURE:
<221> NAME/KEY: MISC_FEATURE
<222> LOCATION: (10)..(10)
<223> OTHER INFORMATION: Xaa can be any naturally occurring amino acid,
      preferably Gly
<220> FEATURE:
<221> NAME/KEY: MISC_FEATURE
<222> LOCATION: (12)..(12)
<223> OTHER INFORMATION: Xaa can be absent or any naturally occurring
      amino acid, preferably Ala
<220> FEATURE:
<221> NAME/KEY: MISC_FEATURE
<222> LOCATION: (13)..(13)
<223> OTHER INFORMATION: Xaa can be absent or any naturally occurring
      amino acid, preferably Leu
<220> FEATURE:
<221> NAME/KEY: MISC_FEATURE
<222> LOCATION: (14)..(14)
<223> OTHER INFORMATION: Xaa can be absent or any naturally occurring
      amino acid, preferably Gly
<220> FEATURE:
<221> NAME/KEY: MISC_FEATURE
<222> LOCATION: (15)..(15)
<223> OTHER INFORMATION: Xaa can be absent or any naturally occurring
      amino acid, preferably Arg
<220> FEATURE:

```
<221> NAME/KEY: MISC_FEATURE
<222> LOCATION: (27)..(27)
<223> OTHER INFORMATION: Xaa can be absent or any naturally occurring
      amino acid, preferably Leu
<220> FEATURE:
<221> NAME/KEY: MISC_FEATURE
<222> LOCATION: (35)..(35)
<223> OTHER INFORMATION: Xaa can be absent or any naturally occurring
      amino acid, preferably Thr
<220> FEATURE:
<221> NAME/KEY: MISC_FEATURE
<222> LOCATION: (36)..(36)
<223> OTHER INFORMATION: Xaa can be absent or any naturally occurring
      amino acid, preferably Pro
<220> FEATURE:
<221> NAME/KEY: MISC_FEATURE
<222> LOCATION: (49)..(49)
<223> OTHER INFORMATION: Xaa can be absent or any naturally occurring
      amino acid, preferably Gly
<220> FEATURE:
<221> NAME/KEY: MISC_FEATURE
<222> LOCATION: (52)..(52)
<223> OTHER INFORMATION: Xaa can be absent or any naturally occurring
      amino acid, preferably Val
<220> FEATURE:
<221> NAME/KEY: MISC_FEATURE
<222> LOCATION: (66)..(66)
<223> OTHER INFORMATION: Xaa can be absent or any naturally occurring
      amino acid, preferably Leu
<220> FEATURE:
<221> NAME/KEY: MISC_FEATURE
<222> LOCATION: (68)..(68)
<223> OTHER INFORMATION: Xaa can be absent or any naturally occurring
      amino acid, preferably Gly
<220> FEATURE:
<221> NAME/KEY: MISC_FEATURE
<222> LOCATION: (69)..(69)
<223> OTHER INFORMATION: Xaa can be absent or any naturally occurring
      amino acid, preferably Thr
<220> FEATURE:
<221> NAME/KEY: MISC_FEATURE
<222> LOCATION: (86)..(86)
<223> OTHER INFORMATION: Xaa can be absent or any naturally occurring
      amino acid, preferably Glu
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: MISC_FEATURE
<222> LOCATION: (122)..(122)
<223> OTHER INFORMATION: Xaa can be absent or any naturally occurring
      amino acid, preferably Val

<400> SEQUENCE: 19

Gly Lys Val Xaa Val Asp Glu Val Xaa Xaa Glu Xaa Xaa Xaa Xaa Leu
1               5                   10                  15

Leu Val Val Tyr Pro Trp Thr Gln Arg Phe Xaa Glu Ser Phe Gly Asp
                20                  25                  30

Leu Ser Xaa Xaa Asp Ala Val Met Gly Asn Pro Lys Val Lys Ala His
            35                  40                  45

Xaa Lys Lys Xaa Leu Gly Ala Phe Ser Asp Gly Leu Ala His Leu Asp
        50                  55                  60

Asn Xaa Lys Xaa Xaa Phe Ala Thr Leu Ser Glu Leu His Cys Asp Lys
65              70                  75                  80

Leu His Val Asp Pro Xaa Asn Phe Arg Leu Leu Gly Asn Val Leu Val
                85                  90                  95

Cys Val Leu Ala His His Phe Gly Lys Glu Phe Thr Pro Pro Val Gln
            100                 105                 110

Ala Ala Tyr Gln Lys Val Val Ala Xaa Xaa Ala Asn
            115                 120
```

```
<210> SEQ ID NO 20
<211> LENGTH: 147
<212> TYPE: PRT
<213> ORGANISM: Artificial Sequence
<220> FEATURE:
<223> OTHER INFORMATION: Consensus sequence of mammalian haemoglobin
      beta chain
<220> FEATURE:
<221> NAME/KEY: MISC_FEATURE
<222> LOCATION: (10)..(10)
<223> OTHER INFORMATION: Xaa can be any naturally occurring amino acid,
      preferably Ser
<220> FEATURE:
<221> NAME/KEY: MISC_FEATURE
<222> LOCATION: (11)..(11)
<223> OTHER INFORMATION: Xaa can be any naturally occurring amino acid,
      preferably Ala
<220> FEATURE:
<221> NAME/KEY: MISC_FEATURE
<222> LOCATION: (15)..(15)
<223> OTHER INFORMATION: Xaa can be any naturally occurring amino acid,
      preferably Leu
<220> FEATURE:
<221> NAME/KEY: MISC_FEATURE
<222> LOCATION: (20)..(20)
<223> OTHER INFORMATION: Xaa can be any naturally occurring amino acid,
      preferably Asn
<220> FEATURE:
<221> NAME/KEY: MISC_FEATURE
<222> LOCATION: (25)..(25)
<223> OTHER INFORMATION: Xaa can be any naturally occurring amino acid,
      preferably Gly
<220> FEATURE:
<221> NAME/KEY: MISC_FEATURE
<222> LOCATION: (26)..(26)
<223> OTHER INFORMATION: Xaa can be any naturally occurring amino acid,
      preferably Gly
<220> FEATURE:
<221> NAME/KEY: MISC_FEATURE
<222> LOCATION: (28)..(28)
<223> OTHER INFORMATION: Xaa can be any naturally occurring amino acid,
      preferably Ala
<220> FEATURE:
<221> NAME/KEY: MISC_FEATURE
<222> LOCATION: (29)..(29)
<223> OTHER INFORMATION: Xaa can be any naturally occurring amino acid,
      preferably Leu
<220> FEATURE:
<221> NAME/KEY: MISC_FEATURE
<222> LOCATION: (30)..(30)
<223> OTHER INFORMATION: Xaa can be any naturally occurring amino acid,
      preferably Gly
<220> FEATURE:
<221> NAME/KEY: MISC_FEATURE
<222> LOCATION: (31)..(31)
<223> OTHER INFORMATION: Xaa can be any naturally occurring amino acid,
      preferably Arg
<220> FEATURE:
<221> NAME/KEY: MISC_FEATURE
<222> LOCATION: (43)..(43)
<223> OTHER INFORMATION: Xaa can be absent or any naturally occurring
      amino acid, preferably Leu
<220> FEATURE:
<221> NAME/KEY: MISC_FEATURE
<222> LOCATION: (51)..(51)
<223> OTHER INFORMATION: Xaa can be any naturally occurring amino acid,
      preferably Thr
<220> FEATURE:
<221> NAME/KEY: MISC_FEATURE
<222> LOCATION: (52)..(52)
<223> OTHER INFORMATION: Xaa can be any naturally occurring amino acid,
      preferably Pro
<220> FEATURE:
<221> NAME/KEY: MISC_FEATURE
<222> LOCATION: (65)..(65)
<223> OTHER INFORMATION: Xaa can be any naturally occurring amino acid,
      preferably Gly
```

```
<220> FEATURE:
<221> NAME/KEY: MISC_FEATURE
<222> LOCATION: (68)..(68)
<223> OTHER INFORMATION: Xaa can be any naturally occurring amino acid,
      preferably Val
<220> FEATURE:
<221> NAME/KEY: MISC_FEATURE
<222> LOCATION: (82)..(82)
<223> OTHER INFORMATION: Xaa can be any naturally occurring amino acid,
      preferably Leu
<220> FEATURE:
<221> NAME/KEY: MISC_FEATURE
<222> LOCATION: (84)..(84)
<223> OTHER INFORMATION: Xaa can be any naturally occurring amino acid,
      preferably Gly
<220> FEATURE:
<221> NAME/KEY: MISC_FEATURE
<222> LOCATION: (85)..(85)
<223> OTHER INFORMATION: Xaa can be any naturally occurring amino acid,
      preferably Thr
<220> FEATURE:
<221> NAME/KEY: MISC_FEATURE
<222> LOCATION: (102)..(102)
<223> OTHER INFORMATION: Xaa can be any naturally occurring amino acid,
      preferably Glu
<220> FEATURE:
<221> NAME/KEY: MISC_FEATURE
<222> LOCATION: (137)..(137)
<223> OTHER INFORMATION: Xaa can be any naturally occurring amino acid,
      preferably Gly
<220> FEATURE:
<221> NAME/KEY: MISC_FEATURE
<222> LOCATION: (138)..(138)
<223> OTHER INFORMATION: Xaa can be any naturally occurring amino acid,
      preferably Val
<220> FEATURE:
<221> NAME/KEY: MISC_FEATURE
<222> LOCATION: (147)..(147)
<223> OTHER INFORMATION: Xaa can be any naturally occurring amino acid,
      preferably His

<400> SEQUENCE: 20

Met Val His Leu Thr Pro Glu Glu Lys Xaa Xaa Val Thr Ala Xaa Trp
1               5                   10                  15

Gly Lys Val Xaa Val Asp Glu Val Xaa Xaa Glu Xaa Xaa Xaa Xaa Leu
                20                  25                  30

Leu Val Val Tyr Pro Trp Thr Gln Arg Phe Xaa Glu Ser Phe Gly Asp
            35                  40                  45

Leu Ser Xaa Xaa Asp Ala Val Met Gly Asn Pro Lys Val Lys Ala His
        50                  55                  60

Xaa Lys Lys Xaa Leu Gly Ala Phe Ser Asp Gly Leu Ala His Leu Asp
65                  70                  75                  80

Asn Xaa Lys Xaa Xaa Phe Ala Thr Leu Ser Glu Leu His Cys Asp Lys
                85                  90                  95

Leu His Val Asp Pro Xaa Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Xaa Xaa Ala Asn Ala Leu Ala His
130                 135                 140

Lys Tyr Xaa
145

<210> SEQ ID NO 21
<211> LENGTH: 124
<212> TYPE: PRT
<213> ORGANISM: Homo sapiens
```

```
<400> SEQUENCE: 21

Gly Lys Val Asn Val Asp Glu Val Gly Glu Ala Leu Gly Arg Leu
1               5                   10                  15

Leu Val Val Tyr Pro Trp Thr Gln Arg Phe Leu Glu Ser Phe Gly Asp
            20                  25                  30

Leu Ser Thr Pro Asp Ala Val Met Gly Asn Pro Lys Val Lys Ala His
        35                  40                  45

Gly Lys Lys Val Leu Gly Ala Phe Ser Asp Gly Leu Ala His Leu Asp
    50                  55                  60

Asn Leu Lys Gly Thr Phe Ala Thr Leu Ser Glu Leu His Cys Asp Lys
65                  70                  75                  80

Leu His Val Asp Pro Glu Asn Phe Arg Leu Leu Gly Asn Val Leu Val
                85                  90                  95

Cys Val Leu Ala His His Phe Gly Lys Glu Phe Thr Pro Pro Val Gln
            100                 105                 110

Ala Ala Tyr Gln Lys Val Val Ala Gly Val Ala Asn
            115                 120

<210> SEQ ID NO 22
<211> LENGTH: 147
<212> TYPE: PRT
<213> ORGANISM: Homo sapiens

<400> SEQUENCE: 22

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Leu Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 23
<211> LENGTH: 80
<212> TYPE: PRT
<213> ORGANISM: Artificial Sequence
<220> FEATURE:
<223> OTHER INFORMATION: N-terminal region of a consensus sequence of
      mammalian transferrins
<220> FEATURE:
<221> NAME/KEY: MISC_FEATURE
<222> LOCATION: (2)..(2)
<223> OTHER INFORMATION: Xaa can be any naturally occurring amino acid,
      preferably Arg
<220> FEATURE:
<221> NAME/KEY: MISC_FEATURE
```

```
<222> LOCATION: (9)..(9)
<223> OTHER INFORMATION: Xaa can be any naturally occurring amino acid,
      preferably Leu
<220> FEATURE:
<221> NAME/KEY: MISC_FEATURE
<222> LOCATION: (10)..(10)
<223> OTHER INFORMATION: Xaa can be any naturally occurring amino acid,
      preferably Val
<220> FEATURE:
<221> NAME/KEY: MISC_FEATURE
<222> LOCATION: (15)..(15)
<223> OTHER INFORMATION: Xaa can be any naturally occurring amino acid,
      preferably Gly
<220> FEATURE:
<221> NAME/KEY: MISC_FEATURE
<222> LOCATION: (24)..(24)
<223> OTHER INFORMATION: Xaa can be any naturally occurring amino acid,
      preferably Thr
<220> FEATURE:
<221> NAME/KEY: MISC_FEATURE
<222> LOCATION: (25)..(25)
<223> OTHER INFORMATION: Xaa can be any naturally occurring amino acid,
      preferably Val
<220> FEATURE:
<221> NAME/KEY: MISC_FEATURE
<222> LOCATION: (31)..(31)
<223> OTHER INFORMATION: Xaa can be any naturally occurring amino acid,
      preferably Ser
<220> FEATURE:
<221> NAME/KEY: MISC_FEATURE
<222> LOCATION: (32)..(32)
<223> OTHER INFORMATION: Xaa can be any naturally occurring amino acid,
      preferably Glu
<220> FEATURE:
<221> NAME/KEY: MISC_FEATURE
<222> LOCATION: (42)..(42)
<223> OTHER INFORMATION: Xaa can be any naturally occurring amino acid,
      preferably Arg
<220> FEATURE:
<221> NAME/KEY: MISC_FEATURE
<222> LOCATION: (47)..(47)
<223> OTHER INFORMATION: Xaa can be any naturally occurring amino acid,
      preferably Ser
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: MISC_FEATURE
<222> LOCATION: (64)..(64)
<223> OTHER INFORMATION: Xaa can be any naturally occurring amino acid,
      preferably Tyr
<220> FEATURE:
<221> NAME/KEY: MISC_FEATURE
<222> LOCATION: (65)..(65)
<223> OTHER INFORMATION: Xaa can be any naturally occurring amino acid,
      preferably Leu
<220> FEATURE:
<221> NAME/KEY: MISC_FEATURE
<222> LOCATION: (71)..(71)
<223> OTHER INFORMATION: Xaa can be any naturally occurring amino acid,
      preferably Ile
<220> FEATURE:
<221> NAME/KEY: MISC_FEATURE
<222> LOCATION: (73)..(73)
<223> OTHER INFORMATION: Xaa can be any naturally occurring amino acid,
      preferably Ala
<220> FEATURE:
<221> NAME/KEY: MISC_FEATURE
<222> LOCATION: (77)..(77)
<223> OTHER INFORMATION: Xaa can be any naturally occurring amino acid,
      preferably Asp
<220> FEATURE:
<221> NAME/KEY: MISC_FEATURE
<222> LOCATION: (78)..(78)
<223> OTHER INFORMATION: Xaa can be any naturally occurring amino acid,
      preferably Ala

<400> SEQUENCE: 23
```

```
Met Xaa Leu Ala Val Gly Ala Leu Xaa Xaa Cys Ala Val Leu Xaa Leu
1               5                   10                  15

Cys Leu Ala Val Pro Asp Lys Xaa Xaa Arg Trp Cys Ala Val Xaa Xaa
                20                  25                  30

His Glu Ala Thr Lys Cys Gln Ser Phe Xaa Asp His Met Lys Xaa Val
                35                  40                  45

Ile Pro Ser Asp Gly Pro Ser Val Ala Cys Xaa Lys Lys Ala Ser Xaa
            50                  55                  60

Xaa Asp Cys Ile Arg Ala Xaa Ala Xaa Asn Glu Ala Xaa Xaa Val Thr
65                  70                  75                  80
```

<210> SEQ ID NO 24
<211> LENGTH: 114
<212> TYPE: PRT
<213> ORGANISM: Artificial Sequence
<220> FEATURE:
<223> OTHER INFORMATION: C-terminal region of a consensus sequence of
      mammalian transferrins
<220> FEATURE:
<221> NAME/KEY: MISC_FEATURE
<222> LOCATION: (3)..(3)
<223> OTHER INFORMATION: Xaa can be any naturally occurring amino acid,
      preferably Thr
<220> FEATURE:
<221> NAME/KEY: MISC_FEATURE
<222> LOCATION: (16)..(16)
<223> OTHER INFORMATION: Xaa can be any naturally occurring amino acid,
      preferably Asp
<220> FEATURE:
<221> NAME/KEY: MISC_FEATURE
<222> LOCATION: (18)..(18)
<223> OTHER INFORMATION: Xaa can be any naturally occurring amino acid,
      preferably Met
<220> FEATURE:
<221> NAME/KEY: MISC_FEATURE
<222> LOCATION: (19)..(19)
<223> OTHER INFORMATION: Xaa can be any naturally occurring amino acid,
      preferably Ser
<220> FEATURE:
<221> NAME/KEY: MISC_FEATURE
<222> LOCATION: (23)..(23)
<223> OTHER INFORMATION: Xaa can be any naturally occurring amino acid,
      preferably Gly
<220> FEATURE:
<221> NAME/KEY: MISC_FEATURE
<222> LOCATION: (25)..(25)
<223> OTHER INFORMATION: Xaa can be any naturally occurring amino acid,
      preferably Val
<220> FEATURE:
<221> NAME/KEY: MISC_FEATURE
<222> LOCATION: (28)..(28)
<223> OTHER INFORMATION: Xaa can be any naturally occurring amino acid,
      preferably Ala
<220> FEATURE:
<221> NAME/KEY: MISC_FEATURE
<222> LOCATION: (30)..(30)
<223> OTHER INFORMATION: Xaa can be any naturally occurring amino acid,
      preferably Lys
<220> FEATURE:
<221> NAME/KEY: MISC_FEATURE
<222> LOCATION: (61)..(61)
<223> OTHER INFORMATION: Xaa can be any naturally occurring amino acid,
      preferably Val
<220> FEATURE:
<221> NAME/KEY: MISC_FEATURE
<222> LOCATION: (62)..(62)
<223> OTHER INFORMATION: Xaa can be any naturally occurring amino acid,
      preferably Lys
<220> FEATURE:
<221> NAME/KEY: MISC_FEATURE
<222> LOCATION: (75)..(75)
<223> OTHER INFORMATION: Xaa can be any naturally occurring amino acid,
      preferably Gly

```
<220> FEATURE:
<221> NAME/KEY: MISC_FEATURE
<222> LOCATION: (78)..(78)
<223> OTHER INFORMATION: Xaa can be any naturally occurring amino acid,
      preferably Ser
<220> FEATURE:
<221> NAME/KEY: MISC_FEATURE
<222> LOCATION: (96)..(96)
<223> OTHER INFORMATION: Xaa can be any naturally occurring amino acid,
      preferably Leu
<220> FEATURE:
<221> NAME/KEY: MISC_FEATURE
<222> LOCATION: (97)..(97)
<223> OTHER INFORMATION: Xaa can be any naturally occurring amino acid,
      preferably Tyr
<220> FEATURE:
<221> NAME/KEY: MISC_FEATURE
<222> LOCATION: (105)..(105)
<223> OTHER INFORMATION: Xaa can be any naturally occurring amino acid,
      preferably Phe
<220> FEATURE:
<221> NAME/KEY: MISC_FEATURE
<222> LOCATION: (107)..(107)
<223> OTHER INFORMATION: Xaa can be any naturally occurring amino acid,
      preferably Glu
<220> FEATURE:
<221> NAME/KEY: MISC_FEATURE
<222> LOCATION: (110)..(110)
<223> OTHER INFORMATION: Xaa can be any naturally occurring amino acid,
      preferably Ser

<400> SEQUENCE: 24

Glu Thr Xaa Glu Asp Cys Ile Ala Lys Ile Met Asn Gly Glu Ala Xaa
1               5                   10                  15

Ala Xaa Xaa Leu Asp Gly Xaa Phe Xaa Tyr Ile Xaa Gly Xaa Cys Gly
            20                  25                  30

Leu Val Pro Val Leu Ala Glu Asn Tyr Asn Lys Ser Asp Asn Cys Glu
        35                  40                  45

Asp Thr Pro Glu Ala Gly Tyr Phe Ala Val Ala Val Xaa Xaa Lys Ser
    50                  55                  60

Ala Ser Asp Leu Thr Trp Asp Asn Leu Lys Xaa Lys Lys Xaa Cys His
65                  70                  75                  80

Thr Ala Val Gly Arg Thr Ala Gly Trp Asn Ile Pro Met Gly Leu Xaa
                85                  90                  95

Xaa Asn Lys Ile Asn His Cys Arg Xaa Asp Xaa Phe Phe Xaa Glu Gly
            100                 105                 110

Cys Ala

<210> SEQ ID NO 25
<211> LENGTH: 698
<212> TYPE: PRT
<213> ORGANISM: Artificial Sequence
<220> FEATURE:
<223> OTHER INFORMATION: Consensus sequence of mammalian transferrins
<220> FEATURE:
<221> NAME/KEY: MISC_FEATURE
<222> LOCATION: (2)..(2)
<223> OTHER INFORMATION: Xaa can be any naturally occurring amino acid,
      preferably Arg
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid,
      preferably Val
<220> FEATURE:
<221> NAME/KEY: MISC_FEATURE
```

```
<222> LOCATION: (15)..(15)
<223> OTHER INFORMATION: Xaa can be any naturally occurring amino acid,
      preferably Gly
<220> FEATURE:
<221> NAME/KEY: MISC_FEATURE
<222> LOCATION: (24)..(24)
<223> OTHER INFORMATION: Xaa can be any naturally occurring amino acid,
      preferably Thr
<220> FEATURE:
<221> NAME/KEY: MISC_FEATURE
<222> LOCATION: (25)..(25)
<223> OTHER INFORMATION: Xaa can be any naturally occurring amino acid,
      preferably Val
<220> FEATURE:
<221> NAME/KEY: MISC_FEATURE
<222> LOCATION: (31)..(31)
<223> OTHER INFORMATION: Xaa can be any naturally occurring amino acid,
      preferably Ser
<220> FEATURE:
<221> NAME/KEY: MISC_FEATURE
<222> LOCATION: (32)..(32)
<223> OTHER INFORMATION: Xaa can be any naturally occurring amino acid,
      preferably Glu
<220> FEATURE:
<221> NAME/KEY: MISC_FEATURE
<222> LOCATION: (42)..(42)
<223> OTHER INFORMATION: Xaa can be any naturally occurring amino acid,
      preferably Arg
<220> FEATURE:
<221> NAME/KEY: MISC_FEATURE
<222> LOCATION: (47)..(47)
<223> OTHER INFORMATION: Xaa can be any naturally occurring amino acid,
      preferably Ser
<220> FEATURE:
<221> NAME/KEY: MISC_FEATURE
<222> LOCATION: (59)..(59)
<223> OTHER INFORMATION: Xaa can be any naturally occurring amino acid,
      preferably Val
<220> FEATURE:
<221> NAME/KEY: MISC_FEATURE
<222> LOCATION: (64)..(64)
<223> OTHER INFORMATION: Xaa can be any naturally occurring amino acid,
      preferably Tyr
<220> FEATURE:
<221> NAME/KEY: MISC_FEATURE
<222> LOCATION: (65)..(65)
<223> OTHER INFORMATION: Xaa can be any naturally occurring amino acid,
      preferably Leu
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: MISC_FEATURE
<222> LOCATION: (73)..(73)
<223> OTHER INFORMATION: Xaa can be any naturally occurring amino acid,
      preferably Ile
<220> FEATURE:
<221> NAME/KEY: MISC_FEATURE
<222> LOCATION: (77)..(77)
<223> OTHER INFORMATION: Xaa can be any naturally occurring amino acid,
      preferably Asp
<220> FEATURE:
<221> NAME/KEY: MISC_FEATURE
<222> LOCATION: (78)..(78)
<223> OTHER INFORMATION: Xaa can be any naturally occurring amino acid,
      preferably Ala
<220> FEATURE:
<221> NAME/KEY: MISC_FEATURE
<222> LOCATION: (84)..(84)
<223> OTHER INFORMATION: Xaa can be any naturally occurring amino acid,
      preferably Gly
<220> FEATURE:
<221> NAME/KEY: MISC_FEATURE
<222> LOCATION: (87)..(87)
<223> OTHER INFORMATION: Xaa can be any naturally occurring amino acid,
      preferably Tyr
<220> FEATURE:
<221> NAME/KEY: MISC_FEATURE
```

```
<222> LOCATION: (88)..(88)
<223> OTHER INFORMATION: Xaa can be any naturally occurring amino acid,
      preferably Asp
<220> FEATURE:
<221> NAME/KEY: MISC_FEATURE
<222> LOCATION: (94)..(94)
<223> OTHER INFORMATION: Xaa can be any naturally occurring amino acid,
      preferably Asn
<220> FEATURE:
<221> NAME/KEY: MISC_FEATURE
<222> LOCATION: (98)..(98)
<223> OTHER INFORMATION: Xaa can be any naturally occurring amino acid,
      preferably Pro
<220> FEATURE:
<221> NAME/KEY: MISC_FEATURE
<222> LOCATION: (104)..(104)
<223> OTHER INFORMATION: Xaa can be any naturally occurring amino acid,
      preferably Tyr
<220> FEATURE:
<221> NAME/KEY: MISC_FEATURE
<222> LOCATION: (107)..(107)
<223> OTHER INFORMATION: Xaa can be any naturally occurring amino acid,
      preferably Lys
<220> FEATURE:
<221> NAME/KEY: MISC_FEATURE
<222> LOCATION: (108)..(108)
<223> OTHER INFORMATION: Xaa can be any naturally occurring amino acid,
      preferably Glu
<220> FEATURE:
<221> NAME/KEY: MISC_FEATURE
<222> LOCATION: (115)..(115)
<223> OTHER INFORMATION: Xaa can be any naturally occurring amino acid,
      preferably Tyr
<220> FEATURE:
<221> NAME/KEY: MISC_FEATURE
<222> LOCATION: (116)..(116)
<223> OTHER INFORMATION: Xaa can be any naturally occurring amino acid,
      preferably Ala
<220> FEATURE:
<221> NAME/KEY: MISC_FEATURE
<222> LOCATION: (121)..(121)
<223> OTHER INFORMATION: Xaa can be any naturally occurring amino acid,
      preferably Lys
<220> FEATURE:
<221> NAME/KEY: MISC_FEATURE
<222> LOCATION: (124)..(124)
<223> OTHER INFORMATION: Xaa can be any naturally occurring amino acid,
      preferably Ser
<220> FEATURE:
<221> NAME/KEY: MISC_FEATURE
<222> LOCATION: (129)..(129)
<223> OTHER INFORMATION: Xaa can be any naturally occurring amino acid,
      preferably Asn
<220> FEATURE:
<221> NAME/KEY: MISC_FEATURE
<222> LOCATION: (146)..(146)
<223> OTHER INFORMATION: Xaa can be any naturally occurring amino acid,
      preferably Gly
<220> FEATURE:
<221> NAME/KEY: MISC_FEATURE
<222> LOCATION: (152)..(152)
<223> OTHER INFORMATION: Xaa can be any naturally occurring amino acid,
      preferably Gly
<220> FEATURE:
<221> NAME/KEY: MISC_FEATURE
<222> LOCATION: (153)..(153)
<223> OTHER INFORMATION: Xaa can be any naturally occurring amino acid,
      preferably Leu
<220> FEATURE:
<221> NAME/KEY: MISC_FEATURE
<222> LOCATION: (161)..(161)
<223> OTHER INFORMATION: Xaa can be any naturally occurring amino acid,
      preferably Pro
<220> FEATURE:
<221> NAME/KEY: MISC_FEATURE
<222> LOCATION: (179)..(179)
<223> OTHER INFORMATION: Xaa can be any naturally occurring amino acid,
      preferably Pro
<220> FEATURE:
```

```
<221> NAME/KEY: MISC_FEATURE
<222> LOCATION: (188)..(188)
<223> OTHER INFORMATION: Xaa can be any naturally occurring amino acid,
      preferably Gln
<220> FEATURE:
<221> NAME/KEY: MISC_FEATURE
<222> LOCATION: (204)..(204)
<223> OTHER INFORMATION: Xaa can be any naturally occurring amino acid,
      preferably Tyr
<220> FEATURE:
<221> NAME/KEY: MISC_FEATURE
<222> LOCATION: (224)..(224)
<223> OTHER INFORMATION: Xaa can be any naturally occurring amino acid,
      preferably Val
<220> FEATURE:
<221> NAME/KEY: MISC_FEATURE
<222> LOCATION: (238)..(238)
<223> OTHER INFORMATION: Xaa can be any naturally occurring amino acid,
      preferably Asp
<220> FEATURE:
<221> NAME/KEY: MISC_FEATURE
<222> LOCATION: (245)..(245)
<223> OTHER INFORMATION: Xaa can be any naturally occurring amino acid,
      preferably Leu
<220> FEATURE:
<221> NAME/KEY: MISC_FEATURE
<222> LOCATION: (255)..(255)
<223> OTHER INFORMATION: Xaa can be any naturally occurring amino acid,
      preferably Asp
<220> FEATURE:
<221> NAME/KEY: MISC_FEATURE
<222> LOCATION: (268)..(268)
<223> OTHER INFORMATION: Xaa can be any naturally occurring amino acid,
      preferably His
<220> FEATURE:
<221> NAME/KEY: MISC_FEATURE
<222> LOCATION: (275)..(275)
<223> OTHER INFORMATION: Xaa can be any naturally occurring amino acid,
      preferably Met
<220> FEATURE:
<221> NAME/KEY: MISC_FEATURE
<222> LOCATION: (276)..(276)
<223> OTHER INFORMATION: Xaa can be any naturally occurring amino acid,
      preferably Gly
<220> FEATURE:
<221> NAME/KEY: MISC_FEATURE
<222> LOCATION: (286)..(286)
<223> OTHER INFORMATION: Xaa can be any naturally occurring amino acid,
      preferably Leu
<220> FEATURE:
<221> NAME/KEY: MISC_FEATURE
<222> LOCATION: (293)..(293)
<223> OTHER INFORMATION: Xaa can be any naturally occurring amino acid,
      preferably Phe
<220> FEATURE:
<221> NAME/KEY: MISC_FEATURE
<222> LOCATION: (309)..(309)
<223> OTHER INFORMATION: Xaa can be any naturally occurring amino acid,
      preferably Gly
<220> FEATURE:
<221> NAME/KEY: MISC_FEATURE
<222> LOCATION: (310)..(310)
<223> OTHER INFORMATION: Xaa can be any naturally occurring amino acid,
      preferably Lys
<220> FEATURE:
<221> NAME/KEY: MISC_FEATURE
<222> LOCATION: (326)..(326)
<223> OTHER INFORMATION: Xaa can be any naturally occurring amino acid,
      preferably Pro
<220> FEATURE:
<221> NAME/KEY: MISC_FEATURE
<222> LOCATION: (327)..(327)
<223> OTHER INFORMATION: Xaa can be any naturally occurring amino acid,
      preferably Arg
<220> FEATURE:
<221> NAME/KEY: MISC_FEATURE
<222> LOCATION: (357)..(357)
<223> OTHER INFORMATION: Xaa can be any naturally occurring amino acid,
      preferably Glu
```

-continued

```
<220> FEATURE:
<221> NAME/KEY: MISC_FEATURE
<222> LOCATION: (381)..(381)
<223> OTHER INFORMATION: Xaa can be any naturally occurring amino acid,
      preferably Ser
<220> FEATURE:
<221> NAME/KEY: MISC_FEATURE
<222> LOCATION: (393)..(393)
<223> OTHER INFORMATION: Xaa can be any naturally occurring amino acid,
      preferably Thr
<220> FEATURE:
<221> NAME/KEY: MISC_FEATURE
<222> LOCATION: (406)..(406)
<223> OTHER INFORMATION: Xaa can be any naturally occurring amino acid,
      preferably Asp
<220> FEATURE:
<221> NAME/KEY: MISC_FEATURE
<222> LOCATION: (408)..(408)
<223> OTHER INFORMATION: Xaa can be any naturally occurring amino acid,
      preferably Met
<220> FEATURE:
<221> NAME/KEY: MISC_FEATURE
<222> LOCATION: (409)..(409)
<223> OTHER INFORMATION: Xaa can be any naturally occurring amino acid,
      preferably Ser
<220> FEATURE:
<221> NAME/KEY: MISC_FEATURE
<222> LOCATION: (413)..(413)
<223> OTHER INFORMATION: Xaa can be any naturally occurring amino acid,
      preferably Gly
<220> FEATURE:
<221> NAME/KEY: MISC_FEATURE
<222> LOCATION: (415)..(415)
<223> OTHER INFORMATION: Xaa can be any naturally occurring amino acid,
      preferably Val
<220> FEATURE:
<221> NAME/KEY: MISC_FEATURE
<222> LOCATION: (418)..(418)
<223> OTHER INFORMATION: Xaa can be any naturally occurring amino acid,
      preferably Ala
<220> FEATURE:
<221> NAME/KEY: MISC_FEATURE
<222> LOCATION: (420)..(420)
<223> OTHER INFORMATION: Xaa can be any naturally occurring amino acid,
      preferably Lys
<220> FEATURE:
<221> NAME/KEY: MISC_FEATURE
<222> LOCATION: (451)..(451)
<223> OTHER INFORMATION: Xaa can be any naturally occurring amino acid,
      preferably Val
<220> FEATURE:
<221> NAME/KEY: MISC_FEATURE
<222> LOCATION: (452)..(452)
<223> OTHER INFORMATION: Xaa can be any naturally occurring amino acid,
      preferably Lys
<220> FEATURE:
<221> NAME/KEY: MISC_FEATURE
<222> LOCATION: (465)..(465)
<223> OTHER INFORMATION: Xaa can be any naturally occurring amino acid,
      preferably Gly
<220> FEATURE:
<221> NAME/KEY: MISC_FEATURE
<222> LOCATION: (468)..(468)
<223> OTHER INFORMATION: Xaa can be any naturally occurring amino acid,
      preferably Ser
<220> FEATURE:
<221> NAME/KEY: MISC_FEATURE
<222> LOCATION: (486)..(486)
<223> OTHER INFORMATION: Xaa can be any naturally occurring amino acid,
      preferably Leu
<220> FEATURE:
<221> NAME/KEY: MISC_FEATURE
<222> LOCATION: (487)..(487)
<223> OTHER INFORMATION: Xaa can be any naturally occurring amino acid,
      preferably Tyr
<220> FEATURE:
<221> NAME/KEY: MISC_FEATURE
<222> LOCATION: (495)..(495)
<223> OTHER INFORMATION: Xaa can be any naturally occurring amino acid,
```

```
       preferably Phe
<220> FEATURE:
<221> NAME/KEY: MISC_FEATURE
<222> LOCATION: (497)..(497)
<223> OTHER INFORMATION: Xaa can be any naturally occurring amino acid,
       preferably Glu
<220> FEATURE:
<221> NAME/KEY: MISC_FEATURE
<222> LOCATION: (500)..(500)
<223> OTHER INFORMATION: Xaa can be any naturally occurring amino acid,
       preferably Ser
<220> FEATURE:
<221> NAME/KEY: MISC_FEATURE
<222> LOCATION: (505)..(505)
<223> OTHER INFORMATION: Xaa can be any naturally occurring amino acid,
       preferably Pro
<220> FEATURE:
<221> NAME/KEY: MISC_FEATURE
<222> LOCATION: (509)..(509)
<223> OTHER INFORMATION: Xaa can be any naturally occurring amino acid,
       preferably Lys
<220> FEATURE:
<221> NAME/KEY: MISC_FEATURE
<222> LOCATION: (529)..(529)
<223> OTHER INFORMATION: Xaa can be any naturally occurring amino acid,
       preferably Asn
<220> FEATURE:
<221> NAME/KEY: MISC_FEATURE
<222> LOCATION: (536)..(536)
<223> OTHER INFORMATION: Xaa can be any naturally occurring amino acid,
       preferably Tyr
<220> FEATURE:
<221> NAME/KEY: MISC_FEATURE
<222> LOCATION: (558)..(558)
<223> OTHER INFORMATION: Xaa can be any naturally occurring amino acid,
       preferably Pro
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: MISC_FEATURE
<222> LOCATION: (563)..(563)
<223> OTHER INFORMATION: Xaa can be any naturally occurring amino acid,
       preferably Gly
<220> FEATURE:
<221> NAME/KEY: MISC_FEATURE
<222> LOCATION: (586)..(586)
<223> OTHER INFORMATION: Xaa can be any naturally occurring amino acid,
       preferably Thr
<220> FEATURE:
<221> NAME/KEY: MISC_FEATURE
<222> LOCATION: (592)..(592)
<223> OTHER INFORMATION: Xaa can be any naturally occurring amino acid,
       preferably Glu
<220> FEATURE:
<221> NAME/KEY: MISC_FEATURE
<222> LOCATION: (603)..(603)
<223> OTHER INFORMATION: Xaa can be any naturally occurring amino acid,
       preferably Asn
<220> FEATURE:
<221> NAME/KEY: MISC_FEATURE
<222> LOCATION: (607)..(607)
<223> OTHER INFORMATION: Xaa can be any naturally occurring amino acid,
       preferably Val
<220> FEATURE:
<221> NAME/KEY: MISC_FEATURE
<222> LOCATION: (622)..(622)
<223> OTHER INFORMATION: Xaa can be any naturally occurring amino acid,
       preferably Gln
<220> FEATURE:
<221> NAME/KEY: MISC_FEATURE
<222> LOCATION: (635)..(635)
<223> OTHER INFORMATION: Xaa can be any naturally occurring amino acid,
       preferably Ser
<220> FEATURE:
<221> NAME/KEY: MISC_FEATURE
<222> LOCATION: (648)..(648)
<223> OTHER INFORMATION: Xaa can be any naturally occurring amino acid,
```

```
            preferably Leu
<220> FEATURE:
<221> NAME/KEY: MISC_FEATURE
<222> LOCATION: (652)..(652)
<223> OTHER INFORMATION: Xaa can be any naturally occurring amino acid,
      preferably Asp
<220> FEATURE:
<221> NAME/KEY: MISC_FEATURE
<222> LOCATION: (678)..(678)
<223> OTHER INFORMATION: Xaa can be any naturally occurring amino acid,
      preferably Val
<220> FEATURE:
<221> NAME/KEY: MISC_FEATURE
<222> LOCATION: (692)..(692)
<223> OTHER INFORMATION: Xaa can be any naturally occurring amino acid,
      preferably Ala
<220> FEATURE:
<221> NAME/KEY: MISC_FEATURE
<222> LOCATION: (696)..(696)
<223> OTHER INFORMATION: Xaa can be any naturally occurring amino acid,
      preferably Arg
<220> FEATURE:
<221> NAME/KEY: MISC_FEATURE
<222> LOCATION: (698)..(698)
<223> OTHER INFORMATION: Xaa can be any naturally occurring amino acid,
      preferably Pro

<400> SEQUENCE: 25

Met Xaa Leu Ala Val Gly Ala Leu Xaa Xaa Cys Ala Val Leu Xaa Leu
1               5                   10                  15

Cys Leu Ala Val Pro Asp Lys Xaa Xaa Arg Trp Cys Ala Val Xaa Xaa
            20                  25                  30

His Glu Ala Thr Lys Cys Gln Ser Phe Xaa Asp His Met Lys Xaa Val
        35                  40                  45

Ile Pro Ser Asp Gly Pro Ser Val Ala Cys Xaa Lys Lys Ala Ser Xaa
    50                  55                  60

Xaa Asp Cys Ile Arg Ala Xaa Ala Xaa Asn Glu Ala Xaa Xaa Val Thr
65                  70                  75                  80

Leu Asp Ala Xaa Leu Val Xaa Xaa Ala Tyr Leu Ala Pro Xaa Asn Leu
                85                  90                  95

Lys Xaa Val Val Ala Glu Phe Xaa Gly Ser Xaa Xaa Asp Pro Gln Thr
            100                 105                 110

Phe Tyr Xaa Xaa Val Ala Val Val Xaa Lys Asp Xaa Gly Phe Gln Met
            115                 120                 125

Xaa Gln Leu Arg Gly Lys Lys Ser Cys His Thr Gly Leu Gly Arg Ser
        130                 135                 140

Ala Xaa Trp Asn Ile Pro Ile Xaa Xaa Leu Tyr Cys Asp Leu Pro Glu
145                 150                 155                 160

Xaa Arg Lys Pro Leu Glu Lys Ala Val Ala Asn Phe Phe Ser Gly Ser
                165                 170                 175

Cys Ala Xaa Cys Ala Asp Gly Thr Asp Phe Pro Xaa Leu Cys Gln Leu
            180                 185                 190

Cys Pro Gly Cys Gly Cys Ser Thr Leu Asn Gln Xaa Phe Gly Tyr Ser
            195                 200                 205

Gly Ala Phe Lys Cys Leu Lys Asp Gly Ala Gly Asp Val Ala Phe Xaa
            210                 215                 220

Lys His Ser Thr Ile Phe Glu Asn Leu Ala Asn Lys Ala Xaa Arg Asp
225                 230                 235                 240

Gln Tyr Glu Leu Xaa Cys Leu Asp Asn Thr Arg Lys Pro Val Xaa Glu
                245                 250                 255

Tyr Lys Asp Cys His Leu Ala Gln Val Pro Ser Xaa Thr Val Val Ala
            260                 265                 270
```

-continued

```
Arg Ser Xaa Xaa Gly Lys Glu Asp Leu Ile Trp Glu Leu Xaa Asn Gln
        275                 280                 285

Ala Gln Glu His Xaa Gly Lys Asp Lys Ser Lys Glu Phe Gln Leu Phe
    290                 295                 300

Ser Ser Pro His Xaa Xaa Asp Leu Leu Phe Lys Asp Ser Ala His Gly
305                 310                 315                 320

Phe Leu Lys Val Pro Xaa Xaa Met Asp Ala Lys Met Tyr Leu Gly Tyr
                325                 330                 335

Glu Tyr Val Thr Ala Ile Arg Asn Leu Arg Glu Gly Thr Cys Pro Glu
                340                 345                 350

Ala Pro Thr Asp Xaa Cys Lys Pro Val Lys Trp Cys Ala Leu Ser His
                355                 360                 365

His Glu Arg Leu Lys Cys Asp Glu Trp Ser Val Asn Xaa Val Gly Lys
    370                 375                 380

Ile Glu Cys Val Ser Ala Glu Thr Xaa Glu Asp Cys Ile Ala Lys Ile
385                 390                 395                 400

Met Asn Gly Glu Ala Xaa Ala Xaa Xaa Leu Asp Gly Xaa Phe Xaa Tyr
                    405                 410                 415

Ile Xaa Gly Xaa Cys Gly Leu Val Pro Val Leu Ala Glu Asn Tyr Asn
        420                 425                 430

Lys Ser Asp Asn Cys Glu Asp Thr Pro Glu Ala Gly Tyr Phe Ala Val
            435                 440                 445

Ala Val Xaa Xaa Lys Ser Ala Ser Asp Leu Thr Trp Asp Asn Leu Lys
450                 455                 460

Xaa Lys Lys Xaa Cys His Thr Ala Val Gly Arg Thr Ala Gly Trp Asn
465                 470                 475                 480

Ile Pro Met Gly Leu Xaa Xaa Asn Lys Ile Asn His Cys Arg Xaa Asp
                485                 490                 495

Xaa Phe Phe Xaa Glu Gly Cys Ala Xaa Gly Ser Lys Xaa Asp Ser Ser
        500                 505                 510

Leu Cys Lys Leu Cys Met Gly Ser Gly Leu Asn Leu Cys Glu Pro Asn
        515                 520                 525

Xaa Lys Glu Gly Tyr Tyr Gly Xaa Thr Gly Ala Phe Arg Cys Leu Val
530                 535                 540

Glu Lys Gly Asp Val Ala Phe Val Lys His Gln Thr Val Xaa Xaa Asn
545                 550                 555                 560

Thr Gly Xaa Lys Asn Pro Asp Pro Trp Ala Lys Asn Leu Asn Glu Lys
            565                 570                 575

Asp Tyr Glu Leu Leu Cys Leu Asp Gly Xaa Arg Lys Pro Val Glu Xaa
        580                 585                 590

Tyr Ala Asn Cys His Leu Ala Arg Ala Pro Xaa His Ala Val Xaa Thr
        595                 600                 605

Arg Lys Asp Lys Glu Ala Cys Val His Lys Ile Leu Arg Xaa Gln Gln
    610                 615                 620

His Leu Phe Gly Ser Asn Val Thr Asp Cys Xaa Gly Asn Phe Cys Leu
625                 630                 635                 640

Phe Arg Ser Glu Thr Lys Asp Xaa Leu Phe Arg Xaa Asp Thr Val Cys
                645                 650                 655

Leu Ala Lys Leu His Asp Arg Asn Thr Tyr Glu Lys Tyr Leu Gly Glu
                660                 665                 670

Glu Tyr Val Lys Ala Xaa Gly Asn Leu Arg Lys Cys Ser Thr Ser Ser
                675                 680                 685
```

```
Leu Leu Glu Xaa Cys Thr Phe Xaa Arg Xaa
    690                 695
```

```
<210> SEQ ID NO 26
<211> LENGTH: 80
<212> TYPE: PRT
<213> ORGANISM: Homo sapiens

<400> SEQUENCE: 26
```

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80
```

```
<210> SEQ ID NO 27
<211> LENGTH: 114
<212> TYPE: PRT
<213> ORGANISM: Homo sapiens

<400> SEQUENCE: 27
```

```
Glu Thr Thr Glu Asp Cys Ile Ala Lys Ile Met Asn Gly Glu Ala Asp
1               5                   10                  15

Ala Met Ser Leu Asp Gly Gly Phe Val Tyr Ile Ala Gly Lys Cys Gly
            20                  25                  30

Leu Val Pro Val Leu Ala Glu Asn Tyr Asn Lys Ser Asp Asn Cys Glu
        35                  40                  45

Asp Thr Pro Glu Ala Gly Tyr Phe Ala Val Ala Val Val Lys Lys Ser
    50                  55                  60

Ala Ser Asp Leu Thr Trp Asp Asn Leu Lys Gly Lys Lys Ser Cys His
65                  70                  75                  80

Thr Ala Val Gly Arg Thr Ala Gly Trp Asn Ile Pro Met Gly Leu Leu
                85                  90                  95

Tyr Asn Lys Ile Asn His Cys Arg Phe Asp Glu Phe Phe Ser Glu Gly
            100                 105                 110

Cys Ala
```

```
<210> SEQ ID NO 28
<211> LENGTH: 698
<212> TYPE: PRT
<213> ORGANISM: Homo sapiens

<400> SEQUENCE: 28
```

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80
```

```
Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
        130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
        210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
            275                 280                 285

Ala Gln Glu His Phe Gly Lys Asp Lys Ser Lys Glu Phe Gln Leu Phe
        290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
        370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
            435                 440                 445

Ala Val Val Lys Lys Ser Ala Ser Asp Leu Thr Trp Asp Asn Leu Lys
450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495
```

-continued

```
Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
            530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
            610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
                660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
690                 695
```